(12) United States Patent
Dzekunov et al.

(10) Patent No.: US 7,141,425 B2
(45) Date of Patent: Nov. 28, 2006

(54) APPARATUS AND METHOD FOR ELECTROPORATION OF BIOLOGICAL SAMPLES

(75) Inventors: Sergey M. Dzekunov, Germantown, MD (US); Hyung J. Lee, West Chester, PA (US); Linhong Li, North Potomac, MD (US); Vininder Singh, Boyds, MD (US); Linda Liu, Clarksville, MD (US); John W. Holaday, Bethesda, MD (US)

(73) Assignee: Maxcyte, Inc., Gaithersburg, MD (US)

( * ) Notice: Subject to any disclaimer, the term of this patent is extended or adjusted under 35 U.S.C. 154(b) by 342 days.

(21) Appl. No.: 10/225,446

(22) Filed: Aug. 21, 2002

(65) Prior Publication Data

US 2003/0073238 A1    Apr. 17, 2003

Related U.S. Application Data

(60) Provisional application No. 60/354,571, filed on Feb. 5, 2002, provisional application No. 60/314,241, filed on Aug. 22, 2001.

(51) Int. Cl.
*C12N 15/87* (2006.01)
(52) U.S. Cl. ............. 435/461; 435/285.2; 514/44
(58) Field of Classification Search ......... 435/461, 435/285.2; 514/44
See application file for complete search history.

(56) References Cited

U.S. PATENT DOCUMENTS

| | | | |
|---|---|---|---|
| 2,955,076 A | 10/1960 | Gossling | |
| 3,676,325 A | 7/1972 | Smith et al. | 204/288 |
| 4,075,076 A | 2/1978 | Xylander | 204/206 |
| 4,081,340 A | 3/1978 | Zimmermann et al. | 204/180 |
| 4,192,869 A | 3/1980 | Nicolau et al. | 424/199 |
| 4,252,657 A | 2/1981 | Boulton et al. | 204/257 |
| 4,321,259 A | 3/1982 | Nicolau et al. | 424/101 |
| 4,440,386 A | 4/1984 | Achelpohl | 271/70 |
| 4,473,563 A | 9/1984 | Nicolau et al. | 424/224 |
| 4,476,004 A | 10/1984 | Pohl | 204/299 |
| 4,478,824 A | 10/1984 | Franco et al. | 424/101 |
| 4,622,302 A | 11/1986 | Sowers | 435/172.2 |
| 4,652,449 A | 3/1987 | Ropars et al. | 424/101 |
| 4,663,292 A | 5/1987 | Wong et al. | 435/287 |
| 4,695,547 A | 9/1987 | Hilliard et al. | 435/173 |
| 4,699,881 A | 10/1987 | Matschke | 435/173 |
| 4,752,586 A | 6/1988 | Ropars et al. | 435/287 |
| 4,764,473 A | 8/1988 | Matschke et al. | 435/287 |
| 4,784,737 A | 11/1988 | Ray et al. | 204/180.1 |
| 4,800,163 A | 1/1989 | Hibi et al. | 435/287 |
| 4,804,450 A | 2/1989 | Mochizuki et al. | 204/299 |
| 4,822,470 A | 4/1989 | Chang | 204/299 |
| 4,840,714 A | 6/1989 | Littlehales | 204/180.1 |
| 4,849,089 A | 7/1989 | Marshall, III | 204/299 |
| 4,849,355 A | 7/1989 | Wong | 435/172.3 |
| 4,874,690 A | 10/1989 | Goodrich, Jr. et al. | 435/2 |
| 4,882,281 A | 11/1989 | Hilliard et al. | 435/287 |
| 4,906,576 A | 3/1990 | Marshall, III | 435/287 |
| 4,910,140 A | 3/1990 | Dower | 435/172.3 |
| 4,923,814 A | 5/1990 | Marshall, III | 435/173 |
| 4,931,276 A | 6/1990 | Franco et al. | 424/533 |
| 4,945,050 A | 7/1990 | Sanford et al. | 435/172.1 |
| 4,946,793 A | 8/1990 | Marshall, III | 435/291 |
| 4,956,288 A | 9/1990 | Barsoum | 435/172.3 |
| 4,970,154 A | 11/1990 | Chang | 435/172.2 |
| 4,995,957 A | 2/1991 | Ziegler et al. | 204/182.8 |
| 5,007,995 A | 4/1991 | Takahashi et al. | 204/299 |
| 5,036,006 A | 7/1991 | Sanford et al. | 435/170.1 |
| 5,043,261 A | 8/1991 | Goodrich et al. | 435/2 |
| 5,098,843 A | 3/1992 | Calvin | 435/287 |
| 5,100,627 A | 3/1992 | Buican et al. | 422/108 |
| 5,100,792 A | 3/1992 | Sanford et al. | 435/172.1 |
| 5,114,681 A | 5/1992 | Bertoncini et al. | 422/111 |
| 5,124,259 A | 6/1992 | Tada | 435/172.1 |
| 5,128,257 A | 7/1992 | Baer | 435/173 |
| 5,134,070 A | 7/1992 | Casnig | 435/173 |
| 5,135,667 A | 8/1992 | Schoendorfer | 210/782 |
| 5,137,817 A | 8/1992 | Busta et al. | 435/173 |
| 5,139,684 A | 8/1992 | Kaali et al. | 210/748 |
| 5,232,856 A | 8/1993 | Firth | 435/287 |
| 5,424,209 A | 6/1995 | Kearney | 435/284 |
| 5,501,662 A | 3/1996 | Hofmann | 604/20 |
| 5,545,130 A | 8/1996 | Hofmann et al. | 604/4 |
| 5,612,207 A | 3/1997 | Nicolau et al. | 435/173.6 |
| 5,676,646 A | 10/1997 | Hofmann et al. | 604/4 |
| 5,720,921 A | 2/1998 | Meserol | 424/44 |
| 5,728,281 A | 3/1998 | Holmström et al. | 204/403 |
| 6,074,605 A | 6/2000 | Meserol et al. | 422/33 |
| 6,090,617 A | 7/2000 | Meserol | 435/285.2 |
| 6,485,961 B1 | 11/2002 | Meserol | 435/285.2 |
| 2001/0001064 A1 | 5/2001 | Holaday | 435/173.6 |

FOREIGN PATENT DOCUMENTS

AT    AU 680890    10/1994

(Continued)

OTHER PUBLICATIONS

Verma et al., Nature, vol. 389, 1997, pp. 239-242.*

(Continued)

*Primary Examiner*—James Ketter
(74) *Attorney, Agent, or Firm*—Fulbright Jaworski LLP

(57) ABSTRACT

The present invention relates to methods and apparatus for the encapsulation of biologically-active substances in various cell populations. More particularly, the present invention relates to a method and apparatus for the encapsulation of biologically-active substances in various cell populations in blood by electroporation to achieve therapeutically desirable changes in the physical characteristics of the various cell populations in blood.

116 Claims, 48 Drawing Sheets

FOREIGN PATENT DOCUMENTS

| | | |
|---|---|---|
| CA | 2214800 | 2/2002 |
| CN | 1195997 | 10/1998 |
| DE | 2405119 | 9/1975 |
| DE | 3603029 | 8/1987 |
| DE | 4440386 | 5/1996 |
| EP | 0137504 | 4/1985 |
| EP | 0343783 | 11/1989 |
| EP | 0362758 | 4/1990 |
| EP | 0472772 | 3/1992 |
| EP | 0798309 | 10/1997 |
| JP | 62151174 | 7/1987 |
| JP | 62171687 | 7/1987 |
| JP | 62228277 | 10/1987 |
| JP | 62265975 | 11/1987 |
| JP | 63141587 | 6/1988 |
| JP | 1141582 | 6/1989 |
| JP | 2131584 | 5/1990 |
| JP | 2131585 | 5/1990 |
| JP | 2186993 | 7/1990 |
| JP | 3195485 | 8/1991 |
| JP | 4027393 | 1/1992 |
| JP | 6349068 | 12/1994 |
| JP | 7180029 | 7/1995 |
| JP | 7320720 | 12/1995 |
| WO | WO 88/04322 | 6/1988 |
| WO | WO 89/02464 | 3/1989 |
| WO | WO 89/03426 | 4/1989 |
| WO | WO 91/18103 | 11/1991 |
| WO | WO 94/21117 | 9/1994 |
| WO | WO 96/28199 | 3/1996 |
| WO | WO 98/24490 | 6/1998 |
| WO | WO 01/24830 | 4/2001 |

OTHER PUBLICATIONS

Anderson, Nature, vol. 392 supplement, 1998, pp. 25-30.*

Juengst, BMJ, vol. 326, 2003, pp. 1410-1411.*

"Advanced Coatings for the Medical Industry," Multi-Arc Scientific Coatings, Copyright © Andal Corp.

"Biological Buffers," In: *The Biological Engineering Handbook*, Bronzino (ed.), CRC Press, pp. 1650, c1995.

"Ion Bond® 16 Zirconium Nitride Coating," Multi-Arc, Inc., 1996.

"Ion Bond® 17 Titanium Aluminum Nitride Coating," Multi-Arc, Inc., 1995.

"Ion Bond® 19 Chromium Nitride Coating," Multi-Arc, Inc., 1995.

"Ion Bond® Coatings for Instruments, Design Considerations," Multi-Arc, Inc., 1995.

"Ion Bond® Coatings for Instruments, Most Commonly Asked Questions," Multi-Arc, Inc., 1995.

"Preparation of certain reagents, anticoagulants and preservative solutions," In: *Practical Haematology*, 5$^{th}$ Edition, Dacie and Lewis (eds.), Appendicies, pp. 598, 1975.

"The Ion Bond Network," Multi-Arc, Inc., 1995.

Abatti et al., "Development of a new geometrical form of micropipette: electrical characteristics and an application as a potassium ion selective electrode," *IEEE Trans. Biomed. Eng.* ,39:43-48, 1992.

Asakami et al., "Materials for electrode of alkali metal thermoelectric converter (AMTEC) (II)," *J. Mater. Sci. Lett.*, 9(8):892-894, 1990.

Behrndt and Lunk, "Biocompatibility of TiN preclinical and clinical investigations," *Materials Sciences & Engineering*, A139:58-60, 1991.

Capizzi et al., "Amifostine mediated protection of normal bone marrow from cytotoxic chemotherapy," *Cancer*, 72:3495-3501, 1993.

Chassy et al., "Transformation of bacteria by electroporation," *Trends in Biotechnology*, 6(12):303-309, 1988.

Coll et al., "Metallurgical and Tribological modification of titanium and titanium alloys by plasma assisted techniques," *Workshop H Society for Biomaterials Implat Retrieval Symposium*, Sep. 17, 1992.

Dunican and Shivnan, "High frequency transformation of whole cells of amino acid producing coryneform bacteria using high voltage electroporation," *Bio/Technology*, 7:1067-1070, 1998.

Egorov and Noikova, "Effect of phase composition of TiN-Ni sintered electrode materials of characteristics of the ESA process," *Sov. Powder Metall Met Ceram.*, 29(9):705-710, 1991.

Einck and Holaday, "Enhancement of tissue oygenation by intracellular introduction of inositol hexaphosphate by flow electroporation of red blood cells," In: *Tissue Oxygenation in Acute Medicine* (*Update in Intensive Care and Emergency Medicine*, 33), Sibbald et al., (eds.), pp. 357-374, c1998.

Gersonde and Nicolau, "Enhancement of the $O_2$ release capacity and of the Bohr-effect of human red blood cells after incorporation of inositol hexaphosphate by fusion with effector-containing lipid vesicles," In: *Origins of Cooperative Binding by Hemoglobin*, 277-282, 1982.

Gersonde and Nicolau, "Improvement of the red blood cell $O_2$ release capacity by lipid vesicle-mediated incorporation of inositol hexaphosphate," *Blut*, 39:1-7, 1979.

Gersonde and Nicolau, "Modification of the oxygen affinity of intracellular haemoglobin by incorporation of polyphosphates into intact red blood cells and enhanced $O_2$ release in the capillary system," *Biblthca Haemat.*, 46:81-92, 1980.

Gersonde and Weiner, "The influence of infusion rate on the acute intravenous toxicity of phytic acid, a calcium-binding agent," *Toxicology*, 22:279-286, 1982.

Hirai et al., "A new antitumor antibiotic, FR-900482" *J. of Antibiotics*, 40/5:607-611, 1987.

Hofmann and Evans, "Eletronic genetic—physical and biological aspects of cellular electromanipulation," *IEEE Engineering in Medicine and Biology Magazine*, 6-11, 19-22, 1986.

Kinosita and Tsong, "Voltage-induced conductance in human erythrocyte membranes," *Biochimical et Biophysica Acta*, 554:479-497, 1979.

Kobayashi et al., "Fabrication of zirconium nitride sintered bodies and the application for electrode materials," *J. Ceram. Soc. Jpn.*, 97(10):1189-1194, (with English summary), 1989.

Kullman et al., "In vitro effects of pentoxifylline on smooth muscle cell migration and blood monocyte production of chemotactic activity for smooth muscle cells: potential therapeutic benefit in the adult respiratory distress syndrome," *Am J. Respir. Cell*, 8:83-88, 1993.

Kurtz and Gordon, "Transparent conducting electrodes on silicon," *Sol. Energy Mater.*, 15(4):229-236, 1987.

Lehninger (ed.), In: *Principles of Biochemistry*, Chapter 8: 181-194, 1982.

Maurer et al., "Reduction of fretting corrosion of Ti-6A1-4V by various surface treatments," *J. Orthop Res.*, 11:865-873, 1993.

Merz et al., "Determination of HIV infection in human bone," *Unfallchirurg*, 941:47-49, (with English summary), 1991.

Mouneimne et al., "Stable rightward shifts of the oxyhemoglobin dissocation curve induced by encapsulation of inositol hexaphosphate in red blood cells using electroporation," *FEBS Letters*, 275:117-120, 1990.

Narayan et al., "Diamond, diamond-like and titanium nitride biocompatible coatings for human body parts," *Materials Sciences & Engineering*, B25:5-10, 1994.

Nicolau et al., "Incorporation of allosteric effectors of hemoglobin in red blood cells. Physiological effects," *Biblthca haemat.*, 51:92-107, 1985.

Nicolau et al., "Short- and long-term physiological effects of improved oxygen transport by red blood cells containing inositol hexaphosphate," In: *Phytic Acid: Chemistry and Applications*, Graf (ed.), Chapter 16:265-290, 1986.

Pietra et al., "Titanium nitride as a coating for surgical instruments used to collect human tissue for trace metal analysis," *Analyst*, 115:1025-1028, 1990.

Ropars et al., "Improved oxygen delivery to tissues and iron chelator transport through the use of lysed and resealed red blood cells: a new perspective on cooley's anemia therapy," *Annals New York Academy of Sciences,* 445:304-315, 1985.

Satomi et al., "Tissue response to implanted ceramic-coated titanium alloys in rats," *J. Oral Rehab.,* 15:339-345, 1988.

Schaldach et al., "Pacemaker electrodes made of titanium nitride," *Biomed. Technik.,* 34:185-190, 1989, with English abstract.

Shoji et al., "New fabrication process for Josephson tunnel junctions with (niobium nitride niobium) double-layered electrodes," *Appl. Phys. Lett.,* 41(11):1097-1099, 1982.

Susuki, "Biomedical electrode with silicon nitride film," *Jpn. J. Med. Electron. Biol.,* 19(2):114-119, (with English summary), 1981.

Taheri et al., "A dry electrode for EEG recording," *Electroencephalography and Clinical Neurophysiology,* 90(5):376-383, 1994.

Tait and Aita, "Aluminum nitride as a corrosion protection coating for steel: self-sealing porous electode model," *Surf. Eng.,* 7(4):327-330, 1991.

Teisseire et al., "Physiological effects of high-$P_{50}$ erythrocyte transfusion on piglets," *J. Appl. Phys.,* 58:1810-1817, 1985.

Teisseire et al., "Significance of low hemoglobin oxygen affinity," 153-159, ??.

Teissere et al., "Long-term physiological effects of enhanced $O_2$ release by inositol hexaphosphate-loaded erythrocytes," *Proc. Natl. Acad. Sci., USA,* 84:6894-6898, 1987.

Therin et al., "A histomorphometric comparison of the muscular tissue reaction to stainless steel, pure titanium and titanium alloy implant materials," *J. Materials Science: Materials in Medicine,* 2:1-8, 1991.

Vasilenko et al., "Preparation of porous electrodes from titanium nitrides," *Poroshkovaia Metallurgiia,* 13:39-42, 1973, article in Russian, (with English summary).

Weiner, "Right shifting of Hb-$O_2$ dissociation in viable red cells by liposomal technique," *Biol. of the Cell,* 47:65-70, 1983.

Weisel et al., "Adverse effects of transfusion therapy during abdominal aortic aneurysectomy," *Surgery,* 83:682-690,1978.

Wisbey et al., "Application of PVD TiN coating to Co-Cr-Mo based surgical implants," *Biomaterials,* 8:477-480, 1987.

Wisbey et al., "Titanium release from TiN coated implant materials," *ImechE,* C384/042:9-14, 1989.

Zhao et al., "Direct current (dc)-plasma CVD equipment with auxiliary heating electrodes," *Vacuum,* 42(17):1109-1111, 1991.

Zhu et al., "Fabrication and characterization of glucose sensors based on a microarray hydrogen peroxide electrode," *Biosensors and Bioelectronics,* 9(4-5):295-300, 1994.

\* cited by examiner

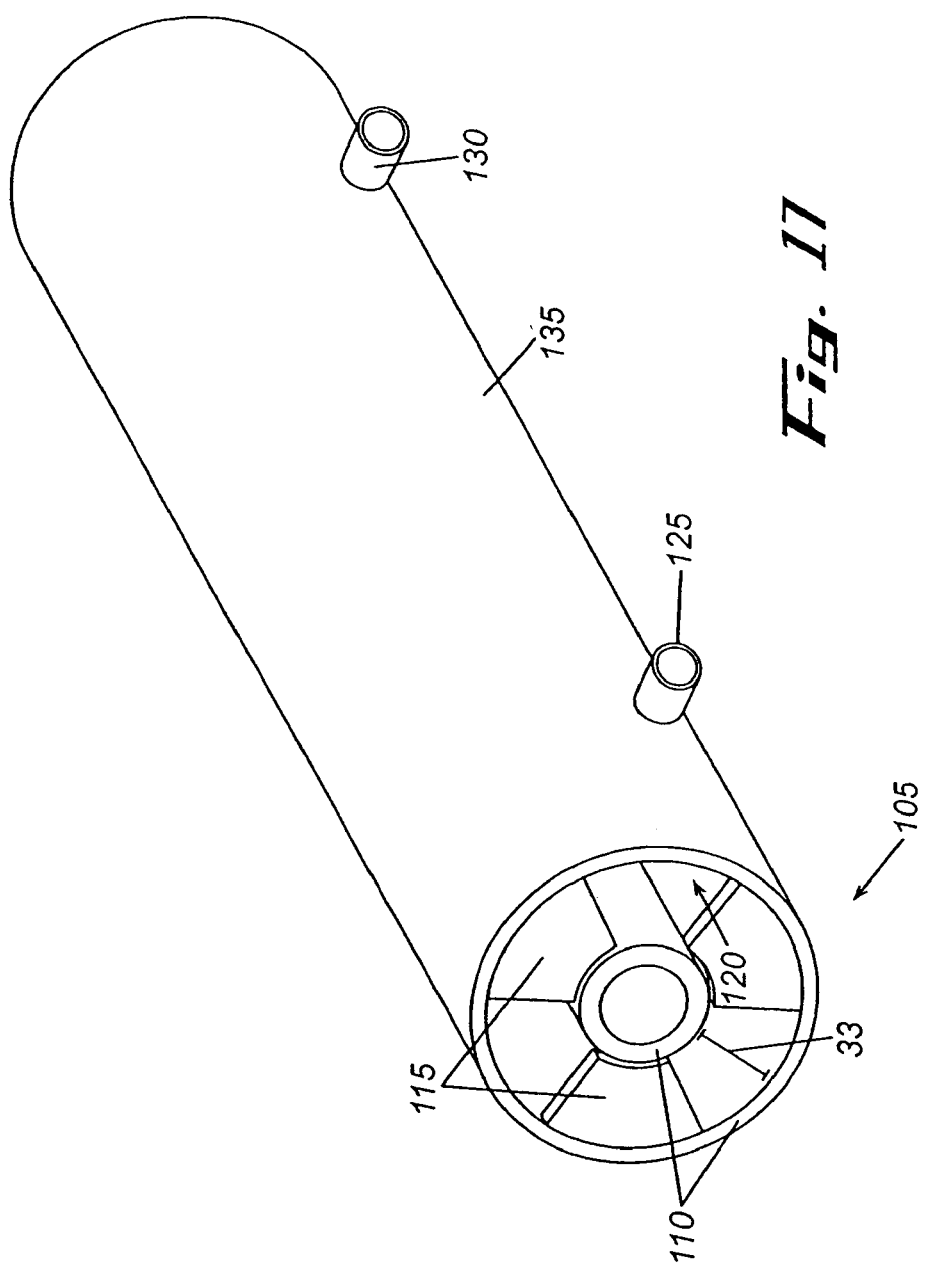

APPARATUS AND METHOD FOR ELECTROPORATION OF BIOLOGICAL SAMPLES

CROSS REFERENCE TO RELATED APPLICATIONS

This application claims benefit of provisional patent application Ser. No. 60/354,571, filed Feb. 5, 2002 and provisional patent application Ser. No. 60/314,241, filed Aug. 22, 2001.

FIELD OF THE INVENTION

The present invention relates to methods and apparatus for the introduction of biologically active substances into various types of living cells or cell particles. More particularly, the present invention relates to a method and apparatus for the introduction of biologically active substances into various cell or cell particle populations suspended in a fluid by electroporation to achieve therapeutic results or to modify cells being used in research to increase their experimental utility. Blood represents one example of cells suspended in a fluid. Other examples include cells being grown in culture outside the body, commonly known as "cell culture" or "tissue culture."

BACKGROUND OF THE INVENTION

Red Blood Cells

In the vascular system of an adult human being, blood has a volume of about 5 to 6 liters. Approximately one half of this volume is occupied by cells, including red blood cells (erythrocytes), white blood cells (leukocytes), and blood platelets. Red blood cells comprise the majority of the cellular components of blood. Plasma, the liquid portion of blood, is approximately 90 percent water and 10 percent various solutes. These solutes include plasma proteins, organic metabolites and waste products, and inorganic compounds.

The major function of red blood cells is to transport oxygen from the lungs to the tissues of the body, and transport carbon dioxide from the tissues to the lungs for removal. Very little oxygen is transported by the blood plasma because oxygen is only sparingly soluble in aqueous solutions. Most of the oxygen carried by the blood is transported by the hemoglobin of the erythrocytes. Erythrocytes in mammals do not contain nuclei, mitochondria or any other intracellular organelles, and they do not use oxygen in their own metabolism. Red blood cells contain about 35 percent by weight hemoglobin, which is responsible for binding and transporting oxygen.

Hemoglobin is a protein having a molecular weight of approximately 64,500 Daltons. It contains four polypeptide chains and four heme prosthetic groups in which iron atoms are bound in the ferrous state. Normal globin, the protein portion of the hemoglobin molecule, consists of two α chains and two β chains. Each of the four chains has a characteristic tertiary structure in which the chain is folded. The four-polypeptide chains fit together in an approximately tetrahedral arrangement, to constitute the characteristic quaternary structure of hemoglobin. There is one heme group bound to each polypeptide chain, which can reversibly bind one molecule of molecular oxygen. When hemoglobin combines with oxygen, oxyhemoglobin is formed. When oxygen is released, the oxyhemoglobin is reduced to deoxyhemoglobin.

Although the secondary and tertiary structure of various hemoglobin subunits are similar, reflecting extensive homology in amino acid composition, the variations in amino acid composition that do exist impart marked differences in hemoglobin's oxygen carrying properties. In addition, the quaternary structure of hemoglobin leads to physiologically important allosteric interactions between the subunits, a property lacking in monomeric myoglobin, which is otherwise very similar to the -subunit of hemoglobin.

Comparison of the oxygen-binding properties of myoglobin and hemoglobin illustrate the allosteric properties of hemoglobin that results from its quaternary structure and differentiate hemoglobin's oxygen-binding properties from that of myoglobin. The curve of oxygen-binding to hemoglobin is sigmoidal typical of allosteric proteins in which the substrate, in this case oxygen, is a positive homotropic effector. When oxygen binds to the first subunit, of deoxyhemoglobin, it increases the affinity of the remaining subunits for oxygen. As additional oxygen is bound to the second and third subunits, oxygen-binding is further, incrementally, strengthened, so that at the oxygen tension in lung alveoli, hemoglobin is fully saturated with oxygen. As oxyhemoglobin circulates to deoxygenated tissue, oxygen is incrementally unloaded and the affinity of hemoglobin for oxygen is reduced. Thus at the lowest oxygen tensions found in very active tissues the binding affinity of hemoglobin for oxygen is very low allowing maximal delivery of oxygen to the tissue. In contrast the oxygen-binding curve for myoglobin is hyperbolic in character indicating the absence of allosteric interactions in this process. When the affinity for oxygen is decreased, the sigmoidal curve is shifted to the right. This shift of the curve is commonly known as a "right shift".

The allosteric oxygen-binding properties of hemoglobin arise directly from the interaction of oxygen with the iron atom of the heme prosthetic groups and the resultant effects of these interactions on the quaternary structure of the protein. When oxygen binds to an iron atom of deoxyhemoglobin it pulls the iron atom into the plane of the heme. Since the iron is also bound to histidine F8, this residue is also pulled toward the plane of the heme ring. The conformational change at histidine F8 is transmitted throughout the peptide backbone resulting in a significant change in tertiary structure of the entire subunit. Conformational changes at the subunit surface lead to a new set of binding interactions between adjacent subunits. The latter changes include disruption of salt bridges and formation of new hydrogen bonds and new hydrophobic interactions, all of which contribute to the new quaternary structure.

The latter changes in subunit interaction are transmitted, from the surface, to the heme binding pocket of a second deoxy subunit and result in easier access of oxygen to the iron atom of the second heme and thus a greater affinity of the hemoglobin molecule for a second oxygen molecule. The tertiary configuration of low affinity, deoxygenated hemoglobin (Hb) is known as the taut (T) state. Conversely, the quaternary structure of the fully oxygenated high affinity form of hemoglobin $Hb(O_2)_4$ is known as the relaxed (R) state.

Delivery of oxygen to tissues depends upon a number of factors including, but not limited to, the volume of blood flow, the number of red blood cells, the concentration of hemoglobin in the red blood cells, the oxygen affinity of the hemoglobin and, in certain species, on the molar ratio of intra-erythrocytic hemoglobins with high and low oxygen affinity. The oxygen affinity of hemoglobin depends on four factors as well, namely: (1) the partial pressure of oxygen, (2) the pH, (3) the concentration of the allosteric effector 2,3-diphosphoglycerate (DPG) in the hemoglobin, and (4) the concentration of carbon dioxide. In the lungs, at an oxygen partial pressure of 100 mm Hg, approximately 98% of circulating hemoglobin is saturated with oxygen. This represents the total oxygen transport capacity of the blood. When fully oxygenated, 100 ml of whole mammalian blood can carry about 21 ml of gaseous oxygen.

The effect of the partial pressure of oxygen and the pH on the ability of hemoglobin to bind oxygen is best illustrated by examination of the oxygen saturation curve of hemoglobin. An oxygen saturation curve plots the percentage of total oxygen-binding sites present in a unit of blood, or a sample that are occupied by oxygen molecules when solutions of the hemoglobin are in equilibrium with varying partial pressures of oxygen.

As stated above, the oxygen saturation curve for hemoglobin is sigmoid. Thus, binding the first molecule of oxygen increases the affinity of the remaining hemoglobin for binding additional oxygen molecules. As the partial pressure of oxygen is increased, a plateau is approached at which each of the hemoglobin molecules is saturated and contains the upper limit of four molecules of oxygen.

The reversible binding of oxygen by hemoglobin is accompanied by the release of protons, according to the equation:

$$HHb^+ + O_2 \rightleftharpoons HbO_2 + kH^+$$

Thus, an increase in the pH will pull the equilibrium to the right and cause hemoglobin to bind more oxygen at a given partial pressure. A decrease in the pH will decrease the amount of oxygen bound.

In the lungs, the partial pressure of oxygen in the air spaces is approximately 90 to 100 mm Hg and the pH is also high relative to normal blood pH (up to 7.6). Therefore, hemoglobin will tend to become almost maximally saturated with oxygen in the lungs. At that pressure and pH, hemoglobin is approximately 98 percent saturated with oxygen. On the other hand, in the capillaries in the interior of the peripheral tissues, the partial pressure of oxygen is only about 25 to 40 mm Hg and the pH is also relatively low (about 7.2 to 7.3). Because muscle cells use oxygen at a high rate thereby lowering the local concentration of oxygen, the release of some of the bound oxygen to the tissue is favored. As the blood passes through the capillaries in the muscles, oxygen will be released from the nearly saturated hemoglobin in the red blood cells into the tissue. Hemoglobin will release about a third of its bound oxygen as it passes through the muscle capillaries, so that when it leaves the muscle, it will be only about 64 percent saturated. In general, the hemoglobin in the venous blood leaving the tissue cycles between about 65 and 97 percent saturation with oxygen in its repeated circuits between the lungs and the peripheral tissues. Thus, oxygen partial pressure and pH function together to affect the release of oxygen by hemoglobin A third important factor in regulating the degree of oxygenation of hemoglobin is the allosteric effector 2,3-diphosphoglycerate (DPG). DPG is the normal physiological effector of hemoglobin in mammalian erythrocytes. DPG regulates the oxygen-binding affinity of hemoglobin in the red blood cells in relationship to the oxygen partial pressure in the lungs. In general, the higher the concentration of DPG in the cell, the lower the affinity of hemoglobin for oxygen.

When the delivery of oxygen to the tissues is chronically reduced, the concentration of DPG in the erythrocytes is increased in normal individuals. For example, at high altitudes the partial pressure of oxygen is significantly less. Correspondingly, the partial pressure of oxygen in the tissues is less. Within a few hours after a normal human subject moves to a higher altitude, the DPG level in the red blood cells increases, causing more DPG to be bound and the oxygen affinity of the hemoglobin to decrease. Increases in the DPG level of red blood cells also occur in patients suffering from hypoxia. This adjustment allows the hemoglobin to release its bound oxygen more readily to the tissues to compensate for the decreased oxygenation of hemoglobin in the lungs.

As normally isolated from blood, hemoglobin contains a considerable amount of DPG. When hemoglobin is "stripped" of its DPG, it shows a much higher affinity for oxygen. When DPG is increased, the oxygen-binding affinity of hemoglobin decreases. A physiologic allosteric effector such as DPG is therefore essential for the normal release of oxygen from hemoglobin in the tissues.

While DPG is the normal physiologic effector of hemoglobin in mammalian red blood cells, phosphorylated inositols are found to play a similar role in the erythrocytes of some birds and reptiles. Although IHP is unable to pass through the mammalian erythrocyte membrane, it is capable of combining with hemoglobin of mammalian red blood cells at the binding site of DPG to modify the allosteric conformation of hemoglobin, the effect of which is to reduce the affinity of hemoglobin for oxygen. For example, DPG can be replaced by inositol hexaphosphate (IHP), which is even more potent than DPG in reducing the oxygen affinity of hemoglobin. IHP has a 1000-fold higher affinity to hemoglobin than DPG (R. E. Benesch et al., *Biochemistry*, Vol. 16, pages 2594–2597 (1977)) and increases the $P_{50}$ of hemoglobin up to values of 96.4 mm Hg at pH 7.4, and 37° C. (*J. Biol. Chem.*, Vol. 250, pages 7093–7098 (1975)).

The oxygen release capacity of mammalian red blood cells can be enhanced by introducing certain allosteric effectors of hemoglobin into erythrocytes, thereby decreasing the affinity of hemoglobin for oxygen and improving the oxygen economy of the blood. This phenomenon suggests various medical applications for treating individuals who are experiencing lowered oxygenation of their tissues due to the inadequate function of their lungs or circulatory system.

Because of the potential medical benefits to be achieved from the use of these modified erythrocytes, various techniques have been developed in the prior art to enable the encapsulation of allosteric effectors of hemoglobin in erythrocytes. Accordingly, numerous devices have been designed to assist or simplify the encapsulation procedure. The encapsulation methods known in the art include osmotic pulse (swelling) and reconstitution of cells, controlled lysis and resealing, incorporation of liposomes, and electroporation. Current methods of electroporation make the procedure commercially impractical on a scale suitable for commercial use.

The following references describe the incorporation of polyphosphates into red blood cells by the interaction of liposomes loaded with IHP: Gersonde, et al., "Modification of the Oxygen Affinity of Intracellular Haemoglobin by Incorporation of Polyphosphates into Intact Red Blood Cells and Enhanced $O_2$ Release in the Capillary System", *Biblthca. Haemat.*, No. 46, pp. 81–92 (1980); Gersonde, et al., "Enhancement of the $O_2$ Release Capacity and of the Bohr-Effect of Human Red Blood Cells after Incorporation of Inositol Hexaphosphate by Fusion with Effector-Containing Lipid Vesicles", *Origins of Cooperative Binding of Hemoglobin*, (1982); and Weiner, "Right Shifting of Hb-$O_2$ Dissociation in Viable Red blood cells by Liposomal Technique," *Biology of the Cell,* Vol. 47, (1983).

Additionally, U.S. Pat. Nos. 4,192,869, 4,321,259, and 4,473,563 to Nicolau et al. describe a method whereby fluid-charged lipid vesicles are fused with erythrocyte membranes, depositing their contents into the red blood cells. In this manner, it is possible to transport allosteric effectors such as inositol hexaphosphate into erythrocytes, where, due to its much higher binding constant, IHP replaces DPG at its binding site in hemoglobin.

In accordance with the liposome technique, IHP is dissolved in a phosphate buffer until the solution is saturated and a mixture of lipid vesicles is suspended in the solution. The suspension is then subjected to ultrasonic treatment or an injection process, and then centrifuged. The upper suspension contains small lipid vesicles containing IHP, which are then collected. Erythrocytes are added to the collected suspension and incubated, during which time the lipid vesicles containing IHP fuse with the cell membranes of the erythrocytes, thereby depositing their contents into the interior of the erythrocyte. The modified erythrocytes are then washed and added to plasma to complete the product.

The drawbacks associated with the liposomal technique include poor reproducibility of the IHP concentrations incorporated in the red blood cells and significant hemolysis of the red blood cells following treatment. Additionally, commercialization is not practical because the procedure is tedious and complicated.

In an attempt to solve the drawbacks associated with the liposomal technique, a method of lysing and the resealing red blood cells was developed. This method is described in the following publication: Nicolau, et al., "Incorporation of Allosteric Effectors of Hemoglobin in Red Blood Cells. Physiologic Effects," *Biblthca. Haemat.,* No. 51, pp. 92–107, (1985). Related U.S. Pat. Nos. 4,752,586 and 4,652,449 to Ropars et al. also describe a procedure of encapsulating substances having biological activity in human or animal erythrocytes by controlled lysis and resealing of the erythrocytes, which avoids the RBC-liposome interactions.

The technique is best characterized as a continuous flow dialysis system which functions in a manner similar to the osmotic pulse technique. Specifically, the primary compartment of at least one dialysis element is continuously supplied with an aqueous suspension of erythrocytes while the secondary compartment of the dialysis element contains an aqueous solution, which is hypotonic with respect to the erythrocyte suspension. The hypotonic solution causes the erythrocytes to lyse. The erythrocyte lysate is then contacted with the biologically active substance to be incorporated into the erythrocyte. To reseal the membranes of the erythrocytes, the osmotic and/or oncotic pressure of the erythrocyte lysate is increased and the suspension of resealed erythrocytes is recovered.

In related U.S. Pat. Nos. 4,874,690 and 5,043,261 to Goodrich et al., a related technique involving lyophilization and reconstitution of red blood cells is disclosed. As part of the process of reconstituting the red blood cells, the addition of various polyanions, including inositol hexaphosphate, is described. Treatment of the red blood cells according to the process disclosed results in a cell with unaffected activity. Presumably, the IHP is incorporated into the cell during the reconstitution process, thereby maintaining the activity of the hemoglobin.

In U.S. Pat. Nos. 4,478,824 and 4,931,276 to Franco et al., a second related method and apparatus is described for introducing effective agents, including inositol hexaphosphate, into mammalian red blood cells by effectively lysing and resealing the cells. The procedure is described as the "osmotic pulse technique." In practicing the osmotic pulse technique, a supply of packed red blood cells is suspended and incubated in a solution containing a compound, which readily diffuses into and out of the cells, the concentration of the compound being sufficient to cause diffusion thereof into the cells so that the contents of the cells become hypertonic. Next, a trans-membrane ionic gradient is created by diluting the solution containing the hypertonic cells with an essentially isotonic aqueous medium in the presence of at least one desired agent to be introduced, thereby causing diffusion of water into the cells with a consequent swelling and an increase in permeability of the outer membranes of the cells. The increase in permeability of the membrane is maintained for a period of time sufficient only to permit transport of at least one agent into the cells and diffusion of the compound out of the cells. These fluxes must be coupled because polyanionic compounds do not simply diffuse across membranes but exchange for ions of equal charge.

Polyanions which may be used in practicing the osmotic pulse technique include pyrophosphate, tripolyphosphate, phosphorylated inositols, 2,3-diphosphoglycerate (DPG), adenosine triphosphate, heparin, and polycarboxylic acids which are water-soluble, and non-disruptive to the lipid outer bilayer membranes of red blood cells.

The osmotic pulse technique has several shortcomings including the fact that the technique is tedious, complicated and unsuited to automation. For these reasons, the osmotic pulse technique has had little commercial success.

Another method for encapsulating various biologically-active substances in erythrocytes is electroporation. Electroporation has been used for encapsulation of foreign molecules in different cell types including IHP red blood cells as described in Mouneimne, et al., "Stable rightward shifts of the oxyhemoglobin dissociation curve induced by encapsulation of inositol hexaphosphate in red blood cells using electroporation," *FEBS,* Vol. 275, No. 1, 2, pp. 117–120 (1990).

The process of electroporation involves the formation of pores in the cell membranes, or in any vesicles, by the application of electric field pulses across a liquid cell suspension containing the cells or vesicles. During the poration process, cells are suspended in a liquid media and then subjected to an electric field pulse. The medium may be electrolyte, non-electrolyte, or a mixture of electrolytes and non-electrolytes. The strength of the electric field applied to the suspension and the length of the pulse (the time that the electric field is applied to a cell suspension) varies according to the cell type. To create a pore in a cell's outer membrane, the electric field must be applied for such a length of time and at such a voltage as to create a set potential across the cell membrane for a period of time long enough to create a pore.

Electroporation has been used effectively to incorporate allosteric effectors of hemoglobin in erythrocytes. In the article by Mouneime, et al., supra, it was reported that right shifts of the hemoglobin-oxygen dissociation curve in treated erythrocytes having incorporated IHP can be achieved. Measurements at 24 and 48 hours after loading with IHP showed a stable $P_{50}$ value indicating that resealing of the erythrocytes was permanent. Furthermore, it was shown that red blood cells loaded with inositol hexaphosphate have a normal half life of eleven days. However, the results obtained by Mouneimne and his colleagues indicate that approximately 20% of the re-transfused cells were lost within the first 24 hours of transfusion. U.S. Pat. Nos.

5,720,921, 6,090,617, and 6,074,605 are incorporated herein by reference in their entirety and all disclose an apparatus and method for flow electroporation.

The electroporation methods disclosed in the prior art are not suitable for processing large volumes of sample, nor use of a high or repetitive electric charge. In addition, the stability of the $P_{50}$ right shift as well as the stability of the red blood cells has not proved adequate for clinical use. Furthermore, the methods are not suitable for use in a continuous or "flow" electroporation chamber. Available electroporation chambers are designed for static use only; namely, processing of samples by batch. Continuous use of a "static" chamber results in over heating of the chamber and increased cell lysis. Furthermore, the existing technology is unable to incorporate a sufficient quantity of IHP in a sufficient percentage of the cells being processed to dramatically change the oxygen carrying capacity of the blood. In addition, the prior art methods require elaborate equipment and are not suited for loading red blood cells of a patient at the point of care. Thus, the procedure is time consuming and not suitable for use on a commercial scale.

What is needed is a simple, efficient and rapid method for encapsulating biologically-active substances in erythrocytes in sufficient volume while preserving the integrity and biologic function of the cells. The potential therapeutic applications of biologically altered blood cells suggests the need for simpler, and more effective and complete methods of encapsulation of biologically-active substances, including allosteric effectors of hemoglobin in intact erythrocytes.

There are numerous clinical conditions that would benefit from treatments that would increase of oxygen bound to hemoglobin. For example to tissue, the leading cause of death in the United States today is cardiovascular disease. The acute symptoms and pathology of many cardiovascular diseases, including congestive heart failure, ischemia, myocardial infarction, stroke, intermittent claudication, and sickle cell anemia, result from an insufficient supply of oxygen in fluids that bathe the tissues. Likewise, the acute loss of blood following hemorrhage, traumatic injury, or surgery results in decreased oxygen supply to vital organs. Without oxygen, tissues at sites distal to the heart, and even the heart itself, cannot produce enough energy to sustain their normal functions. The result of oxygen deprivation is tissue death and organ failure. Another area that would benefit from treatments that would increase delivery of oxygen bound to hemoglobin to tissue is racing animals, athletes, etc.

Another area is in treating diseases such as adult respiratory distress syndrome because administration of blood that is capable of increased delivery of oxygen to the peripheral tissues will ease the pressure of loading hemoglobin in the lungs.

Although the attention of the American public has long been focused on the preventive measures required to alleviate heart disease, such as exercise, appropriate dietary habits, and moderation in alcohol consumption, deaths continue to occur at an alarming rate. One approach to alleviate the life-threatening consequences of cardiovascular disease is to increase oxygenation of tissues during acute stress. The same approach is also appropriate for persons suffering from blood loss or chronic hypoxic disorders, such as congestive heart failure.

Another condition that could benefit from an increase in the delivery of oxygen to the tissues is anemia. A significant portion of hospital patients experience anemia or a low "crit" caused by an insufficient quantity of red blood cells or hemoglobin in their blood. This leads to inadequate oxygenation of their tissues and subsequent complications. Typically, a physician believes that he or she can temporarily correct this condition by transfusing the patient with units of packed red blood cells.

Enhanced tissue oxygenation may also reduce the number of heterologous transfusions and allow use of autologous transfusions in more cases. The current method for treatment of anemia or replacement of blood loss is transfusion of whole human blood. It is estimated that three to four million patients receive transfusions in the U.S. each year for surgical or medical needs. In situations where there is more time or where the religious beliefs of the patient forbid the use of heterologous blood for transfusions, it is advantageous to completely avoid the use of donor or heterologous blood and instead use autologous blood.

Often the amount of blood that can be drawn and stored prior to surgery limits the use of autologous blood. Typically, a surgical patient does not have enough time to donate a sufficient quantity of blood prior to surgery. A surgeon would like to have several units of blood available. As each unit requires a period of several weeks between donations and can not be done less than two weeks prior to surgery, it is often impossible to sequester an adequate supply of blood. By processing autologous blood with IHP, less blood is required and it becomes possible to completely avoid the transfusion of heterologous blood.

As IHP-treated red blood cells transport 2–3 times as much oxygen as untreated red blood cells, in many cases, a physician will need to transfuse fewer units of IHP-treaded red blood cells. This exposes the patient to less heterologous blood, decreases the extent of exposure to viral diseases from blood donors and minimizes immune function disturbances secondary to transfusions. The ability to infuse more efficient red blood cells is also advantageous when the patient's blood volume is excessive. In other more severe cases, where oxygen transport is failing, the ability to rapidly improve a patient's tissue oxygenation is life saving.

Although it is evident that methods of enhancing oxygen delivery to tissues have potential medical applications, currently there are no methods clinically available for increasing tissue delivery of oxygen bound to hemoglobin. Transient elevations of oxygen deposition (6 to 12 hours) have been described in experimental animals using either DPG or molecules that are precursors of DPG. The natural regulation of DPG synthesis in vivo and its relatively short biological half-life, in addition to its lower efficiency in modulating Hb properties, however, limit the DPG concentration and the duration of increased tissue $PO_2$, and thus limit its therapeutic usefulness.

What is needed is a simple, efficient and rapid method for encapsulating biologically-active substances, such as IHP, in erythrocytes without damaging the erythrocytes beyond their ability to produce a clinical effect. An important requirement for any system of introducing IHP into red blood cells is that the right shift of the sigmoidal oxygen-binding curve be substantially stable and the red blood cell must be substantially similar to untreated red blood cells.

Gene Transfection

Efforts to develop human gene therapies have their roots in the 1950s, when early successes with kidney transplantation led to speculation that it might be possible to transplant cells from a normal individual into a patient suffering from a genetic disease. Soon after the discovery of the enzymatic defects in Gaucher's and Niemann-Pick disease, scientists considered organ and bone marrow transplantation and enzyme supplementation to treat rare genetic disorders (Brady, R., NEJM 275:312 (1966)). By the late 1960s and early 1970s, several investigators speculated that it also might be possible to introduce genes into a patient's own cells, and the cloning of the first human genes only a few years later intensified work in the field.

Until recently, almost all of the theoretical and experimental work on human gene therapy was centered on extremely rare genetic diseases, and gene therapy has come to mean, to many in the field, the modification of a patient's genes to treat a genetic disease. However, gene therapy has far wider applications than simply treatment of a genetic disease. Gene therapy is perhaps more appropriately described as medical intervention in which cells, either from the individual to be treated or another appropriate source, are modified genetically to treat or cure any condition, regardless of etiology, that will be ameliorated by the long-term delivery of a therapeutic protein. Gene therapy can therefore be thought of as an in vivo protein production and delivery system, and almost all diseases that are currently treated by the administration of proteins are candidates for treatment using gene therapy.

Gene therapy can be divided into two areas: germ cell and somatic cell gene therapy. Germ cell gene therapy refers to the modification of sperm cells, egg cells, zygotes, or early stage embryos. On the basis of both ethical and practical criteria, germ cell gene therapy is inappropriate for human use. In contrast to germ cell gene therapy, somatic cell gene therapy would affect only the person under treatment (somatic cells are cells that are not capable of developing into whole individuals and include all of the body's cells with the exception of the germ cells). As such, somatic cell gene therapy is a reasonable approach to the treatment and cure of certain disorders in human beings.

In conventional somatic cell gene therapy system, somatic cells (e.g., fibroblasts, hepatocytes, or endothelial cells) are removed from the patient, cultured in vitro, transfected with the gene(s) of therapeutic interest, characterized, and reintroduced into the patient. The means by which these five steps are carried out are the distinguishing features of a given gene therapy system.

Presently-available approaches to gene therapy include the use of infectious vectors, such as retroviral vectors, which include the genetic material to be expressed. Such approaches have limitations, such as the potential of generating replication-competent viruses during vector production; recombination between the therapeutic virus and endogenous retroviral genomes, potentially generating infectious agents with novel cell specificities, host ranges, or increased virulence and cytotoxicity; independent integration into large numbers of cells, increasing the risk of a tumorigenic insertional event; limited cloning capacity in the retrovirus (which restricts therapeutic applicability) and short-lived in vivo expression of the product of interest. A better approach to providing gene products, particularly one that avoids the risks associated with presently available methods and provides long-term production, would be valuable.

A method for encapsulating genetic material in various cell populations is electroporation. Electroporation has been used for encapsulation of foreign molecules in different cell types including IHP red blood cells as described in Mouneimne, et al supra. The electroporation methods disclosed in the prior art are not suitable for processing large volumes of sample, nor use of a high or repetitive electric charge. One of the problems with electroporation of cells has always been the excess heat that occurs during the electroporation process. This heat generated by the electroporation process causes extensive damage to living cells. In addition, the stability of the transformed cells has not proved adequate for clinical use. Furthermore, the methods are not suitable for use in a continuous or "flow" electroporation chamber. Most available electroporation chambers are designed for static use only. Namely, processing of samples by batch. Continuous use of a "static" chamber results in over heating of the chamber and increased cell lysis. Furthermore, the existing technology is unable to incorporate a sufficient quantity of genetic material in a sufficient percentage of the cells being processed. In addition, the prior art methods require elaborate equipment and are not suited for transforming cells of a patient at the point of care. Thus, the procedure is time consuming and not suitable for use on a commercial scale.

Prior Art Flow Cells

U.S. Pat. No. 5,676,646 discloses a flow electroporation apparatus with a flow cell comprising two electrodes separated by a non-conductive spacer, the spacer defining a flow path. The major problem with this flow cell as well as other prior art flow cells is that the surface area of the electrode is not sufficient to dissipate heat as the cells are being electroporated. Thus, the heat buildup in the prior art flow cells is very large as the cells are being electroporated. This heat build up can cause damage to cells and cell components and decrease the efficiency of the electroporation process.

What is needed is a simple, efficient and rapid method for encapsulating genetic material in cells in sufficient volume in real-time, while preserving the integrity and biologic function of the cells. The potential therapeutic applications of transformed cells suggests the need for simpler, and more effective and complete methods of encapsulation of genetic material in intact cells. In addition, a flow cell is needed that is capable of removing heat so that damage to living cells that are being electroporated is kept to a minimum.

SUMMARY OF THE INVENTION

The present invention relates to a method and apparatus for the encapsulation of biologically active substances in cell populations. The present invention is particularly suited for cells found in blood and other body fluids. More specifically, the present invention provides an electroporation chamber that may form part of an automated, self-contained, flow apparatus for encapsulating compounds or compositions, such as inositol hexaphosphate, in cells found in blood. More particularly, the present invention also provides a novel flow electroporation cell assembly that is both simple and efficient. One embodiment of the present inventions is a flow electroporation device comprising walls defining a flow channel configured to receive and to transiently contain a continuous flow of a suspension comprising particles, an inlet flow portal in fluid communication with the flow channel, whereby the suspension can be introduced into the flow channel through the inlet flow portal, an outlet flow portal in fluid communication with the flow channel, whereby the suspension can be withdrawn from the flow channel through the outlet flow portal, the walls defining the flow channel comprising a first electrode plate forming a first wall of the flow channel and a second electrode plate forming a second wall of the flow channel opposite the first wall; wherein the area of the electrodes contact with the suspension, and the distance between the electrodes is chosen so that the thermal resistance of the flow channel is less than approximately 10° C. per Watt, preferably less than approximately 4° C. per Watt, the paired electrodes are placed in electrical communication with a source of electrical energy, whereby an electrical field is formed between the electrodes; whereby the suspension of the particles flowing through the flow channel can be subjected to an electrical field formed between the electrodes.

In a specific embodiment, the biologically active substances are incorporated in red blood cells, thereby reducing the affinity of the hemoglobin for oxygen and enhancing the delivery of oxygen by red blood cells to tissues of a patient. The term "patient" as used here is either a human or an animal. Encapsulation is preferably achieved by electroporation; however, it is contemplated that other methods of encapsulation may be used in practicing the present invention. The method and apparatus, including the electroporation chamber, of the present invention, is equally suited to the encapsulation of a variety of biologically active substances in various cell populations.

The apparatus and method of the present invention is suited to the incorporation of a variety of biologically active substances in cells and lipid vesicles. The method, apparatus and chamber of the present invention may be used for introducing a compound or biologically active substance into a vesicle whether that vesicle is engineered or naturally occurring.

In one embodiment of the present invention, substances or drugs can be introduced into cells or fragments of cells such as platelets. For example, thrombus-dissolving substances such as tissue plasminogen activator or streptokinase and the like can be introduced into a population of platelets. These platelets loaded with the thrombus dissolving substances can be then introduced into a patient who is suffering from a thrombus blocking a blood vessel. The platelet containing the thrombus dissolving substance will then migrate to the site of the thrombus and attach itself to the thrombus. Because the treated platelets contain active thrombus dissolving enzymes, the thrombus is then dissolved. The thrombus dissolving substances can be introduced into the platelets by a variety of methods with the most preferable method being according to the apparatus of the present invention. In another embodiment of the present invention, substances or drugs can be introduced into white cells for the delivery of drugs to the body as a whole or to specific sites within the body. An example of white cells that can be used as delivery vehicles include, but are not limited to, dendritic cells, lymphocytes, macrophages, and the like.

The apparatus, method, and chamber of the present invention may be used to introduce IHP into erythrocytes. The encapsulation of inositol hexaphosphate in red blood cells by electroporation according to the present invention results in a significant decrease in the hemoglobin affinity for oxygen without substantially affecting the life span, ATP levels, K+ levels, or normal Theological competence of the cells. In addition, the Bohr effect is not altered except to shift the $O_2$ binding curve to the right. Lowering the oxygen affinity of the erythrocytes increases the capacity of erythrocytes to dissociate the bound oxygen and thereby improves the oxygen supply to the tissues. Enhancement of the oxygen-release capacity of erythrocytes brings about significant physiological effects, such as a reduction in cardiac output, an increase in the arteriovenous differences, and improved tissue oxygenation.

The modified erythrocytes prepared in accordance with the present invention, having improved oxygen release capacities, may find their use in situations such as those illustrated below:

1. Under conditions of low oxygen-partial pressure, such as at high altitudes;

2. When the oxygen exchange surface of the lung is reduced, such as occurs in emphysema and adult respiratory distress syndrome;

3. When there is an increased resistance to oxygen diffusion in the lung, such as occurs in pneumonia or asthma;

4. When there is a decrease in the oxygen-transport capacity of erythrocytes, such as occurs with erythropenia or anemia, or when an arteriovenous shunt is used;

5. To treat blood circulation disturbances, such as arteriosclerosis, thromboembolic processes, organ infarct, congestive heart failure, cardiac insufficiency or ischemia;

6. To treat conditions of high oxygen affinity of hemoglobin, such as hemoglobin mutations, chemical modifications of N-terminal amino acids in the hemoglobin-chains, or enzyme defects in erythrocytes;

7. To accelerate detoxification processes by improving oxygen supply;

8. To decrease the oxygen affinity of conserved blood;

9. To improve the efficacy of various cancer treatments; and

10. To enhance the athletic performance of humans or animals.

According to the method and apparatus of the present invention, it is possible to produce modified erythrocytes that contribute to an improved oxygen economy of the blood. These modified erythrocytes are obtained by incorporation of allosteric effectors, such as IHP, by electroporation of the erythrocyte membranes.

The incorporation of the biologically active substances into the cells in accordance with the method of the present invention, including the encapsulation of allosteric effectors of hemoglobin into erythrocytes, is conducted extracorporally via an automated, flow electroporation apparatus. Briefly, in one embodiment of the present invention, a cell suspension is introduced into a separation and wash stage of a flow encapsulation apparatus. It is to be understood that cells can be washed by any suitable method known to those of ordinary skill in the art, including but not limited to, centrifugation, filtration, chelation, and osmotic methods. The cells are separated from the suspension, washed and re-suspended in a solution of the biologically active substance to be introduced into the cell. This suspension is introduced into the electroporation chamber and then incubated. Following electroporation and incubation, the cells are washed and separated. A contamination check is optionally conducted to confirm that all unencapsulated biologically active substance has been removed. Then, the cells are prepared for storage or reintroduction into a patient.

In accordance with the present invention and with reference to the preferred embodiment, blood is drawn from a patient, the erythrocytes are separated from the drawn blood, the erythrocytes are modified by the incorporation of allosteric effectors and the modified erythrocytes and blood plasma is reconstituted. In this manner, it is possible to prepare and store blood containing IHP-modified erythrocytes.

The apparatus of the present invention provides an improved method for the encapsulation of biologically-active substances in cells including an apparatus which is self-contained and therefore sterile, an apparatus which can process large volumes of cells within a shortened time period, an apparatus having improved contamination detection, cooling and incubation elements, an apparatus that is entirely automated and which does not require the active control of a technician once a sample is introduced into the apparatus.

Another embodiment of the present invention is a preparation of red blood cells that has a stable right shifted oxygen dissociation curve. The phrase "stable right shifted blood" as used herein means that the right shifted oxygenation curve remains higher than untreated red blood cells over the same period of time. Untreated freshly drawn red blood cells will have a $P_{50}$ of approximately 27 mm Hg. This value decreases over time as it is stored in the blood bank at 2–8° C. due to the loss of the allosteric effector 2,3-diphosphoglycerate. After several days in storage the $P_{50}$ drops to around 22–25 mm Hg. After 1 to 2 weeks the value can drop to around 18–20 mm Hg. It is contemplated as part of the present invention a preparation of isolated red blood cells that have a $P_{50}$ greater than approximately 30 mm Hg. These red blood cells have a stable $P_{50}$ that remains substantially the same over the storage life of the red blood cells or the $P_{50}$ remains substantially above the $P_{50}$ of untreated blood over a period of time. Thus, one embodiment of the present invention is an isolated preparation of red blood cells that can be stored under normal blood bank conditions; e.g., 2–8° C., and has a substantially stable $P_{50}$ of greater than approximately 30 mm Hg, more desirably greater than approximately 35 mm Hg, even more desirably greater than approximately 40 mm Hg, and most desirably greater than approximately 45 mm Hg. It should be noted that depending upon the particular condition that is being treated, more cells with less of an average right shift may be used or fewer cells with a greater average right shift may be used. The present invention of treating red blood cells by flow electroporation with IHP is capable of achieving right shifts greater than approximately 30 mm Hg, more desirably greater than approximately 35 mm Hg, even more desirably greater than approximately 40 mm Hg, and most desirably greater than approximately 45 mm Hg in at least one unit of blood in less than 4 hours. Transfection efficiency can be measured either by the percentage of the cells that express the product of the gene or the secretion level of the product express by the gene.

Another aspect of the present invention is the ability to electroporate cells with minimal cell damage. For example, according to the present invention, red blood cells can be loaded with IHP by flow electroporation with a minimum of 10% hemolysis. Typically there is 3% to 5% hemolysis immediately after the electroporation process and another 3% to 5% hemolysis in the recovery buffer. After several hours, the rate of hemolysis drops to near zero.

It is further contemplated as part of the present invention that the red blood cells that have a substantially stable elevated $P_{50}$ have been treated with IHP, so that the IHP passes through the red blood cell membrane so that it can bind allosterically to the DPG binding site of hemoglobin. The method of introducing the IHP into the interior of the red blood cell membrane can be by any method that will produce a substantially stable preparation of red blood cells with an elevated $P_{50}$. For example, the red blood cells can be treated as described herein by flow electroporation in the presence of IHP, or the red blood cells can be exposed to hypo- or hyperosmotic agents, or to membrane solubilizing agents to allow a chemical such as IHP to pass through the red blood cell membrane so that the IHP molecule can bind allosterically to the DPG binding site, thereby replacing the natural DPG in the allosteric binding site on the hemoglobin molecule.

In addition, the red blood cell preparation can be a population of normal, untreated red blood cells that naturally have an elevated $P_{50}$ level. A population of normal, untreated red blood cells that has an elevated $P_{50}$ level can be isolated by density gradient fractionation methods. (See e.g., Bourget, et al., Adv. Exp. Med. Biol, 1992).

Another embodiment of the present invention includes a method of gene therapy including, but not limited to, the introduction of ribonucleic acid preparations, such as DNA, into live cells. The DNA preparations preferably code for a desired protein and can optionally contain vectors that will facilitate the introduction of the DNA into the genetic mechanisms of the cell and thereby (1) increase the expression of the desired protein; (2) regulate the metabolism of a cell; (3) change the phenotype of a cell or (4) be used as a carrier inside the cell. These methods of adding vectors to naked DNA preparations are well known to those of ordinary skill in the art. The DNA that is introduced using the flow electroporation apparatus of the present invention can be naked DNA or can contain other agents to facilitate entry of the DNA into the cell.

The present invention relates to a method and apparatus for the encapsulation of genetic material in various cell populations found in blood. More specifically, the present invention provides an electroporation chamber that may form part of an automated, self-contained, flow apparatus for encapsulating genetic materials in cells and, more specifically in cells found in blood. In a specific embodiment the genetic material is incorporated in lymphocytes, thereby altering the genetic component of the lymphocytes and transforming the lymphocytes. Encapsulation is preferably achieved by electroporation. The method and apparatus, including the electroporation chamber, of the present invention is equally suited to the encapsulation of genetic material in various cell populations.

The apparatus and method of the present invention is suited to the incorporation of genetic material in cells and lipid vesicles. The method, apparatus and chamber of the present invention may be used for introducing genetic material into a vesicle whether that vesicle is engineered or naturally occurring. Thus, the present invention includes a method of transfecting a cell comprising providing a nucleic acid or an expression vector coding for a desired protein or peptide and introducing the nucleic acid or expression vector into the cell by flow electroporation.

The incorporation of the genetic material into the cells in accordance with the method of the present invention, including the encapsulation of genetic material into lymphocytes, is conducted extracorporally via an automated, flow electroporation apparatus. Briefly, a cell suspension is introduced into the separation and washbowl chamber of the flow encapsulation apparatus. The cells are separated from the suspension, washed and re-suspended in a solution of the genetic material to be introduced into the cell. This suspension is introduced into the electroporation chamber and then incubated. Following electroporation and incubation, the cells are washed and separated. A contamination check is optionally conducted to confirm that all unencapsulated genetic material has been removed. Then, the cells are prepared for storage or reintroduction into a patient. The present invention also includes vaccine wherein an expression vector coding for an antigen is introduced into a cell and the transfected cell is then introduced into a human or animal. The transected cell line expresses the antigen and the body then mounts an immune reaction against the antigen. Optionally, the cell line can be cotransfected with an expression vector that codes for the desired antigen and with a cytokine that will act as an adjuvant thereby enhancing the immune response.

In accordance with the present invention and with reference to the preferred embodiment, blood is drawn from a patient, the lymphocytes are separated from the drawn blood, the lymphocytes are modified by the incorporation of genetic material and the transformed lymphocytes and other components of the blood are reconstituted.

Accordingly, it is an object of the present invention to provide an automated, continuous flow electroporation apparatus.

It is another object of the present invention to provide a continuous flow electroporation device that produces a homogenous population of loaded cells or vesicles.

It is another object of the present invention to provide a sterile and nonpyrogenic method of encapsulating biologically active substances in cells.

It is another object of the present invention to provided a method and apparatus which results in stable resealing of cells or vesicles following electroporation to minimize lysis of the modified cells or vesicles after electroporation.

It is another object of the present invention to provide a flow electroporation system of the present invention that produces a modified cell population from which all exogenous non-encapsulated biologically active substances have been removed.

It is another object of the present invention to provide a method and apparatus that allows continuous encapsulation of biologically active substances in a population of cells or vesicles.

It is a further object of the present invention to provide a method and apparatus that achieves the above-defined objects, features, and advantages in a single cycle.

It is a further object of the present invention to provide a method and apparatus that is capable of introducing drugs and substances into platelets.

It is another object of the present invention to provide a continuous flow electroporation chamber.

It is another object of the present invention to provide an improved and more efficient method of encapsulating biologically active substances in cells than those methods currently available.

It is another object of the invention to provide improved combinations of electrical treatment of cells in terms of electric field strength, duration and frequency of electrical treatment that improve the efficiency of electroporation of various cell types.

It is another object of the invention to provide a device for flow electroporation that maintains a sterile path through which cells can pass during the electroporation process, thereby enabling use of flow electroporation in a clinical setting.

It is a further object of the present invention to provide a composition suitable for use in the treatment of conditions and/or disease states resulting from a lack of or decrease in oxygenation.

Other objects, features, and advantages of the present invention will become apparent upon reading the following detailed description of the disclosed embodiments of the invention when taken in conjunction with the appended drawing and the claims.

BRIEF DESCRIPTION OF THE DRAWING

FIG. 3 is a schematic diagram system board general layout.

FIG. 30A is an exploded perspective view of a fourth disclosed embodiment of the flow electroporation cell assembly of the present invention.

FIG. 30D is a side cross-sectional view taken along the line 30D—30D shown in FIG. 30C.

FIG. 30F is the opposite end view of the flow electroporation cell assembly shown in FIG. 30B.

FIG. 32A is an exploded perspective view of a sixth disclosed embodiment of the flow electroporation cell assembly of the present invention.

DETAILED DESCRIPTION OF THE DISCLOSED EMBODIMENTS

Figure 1:
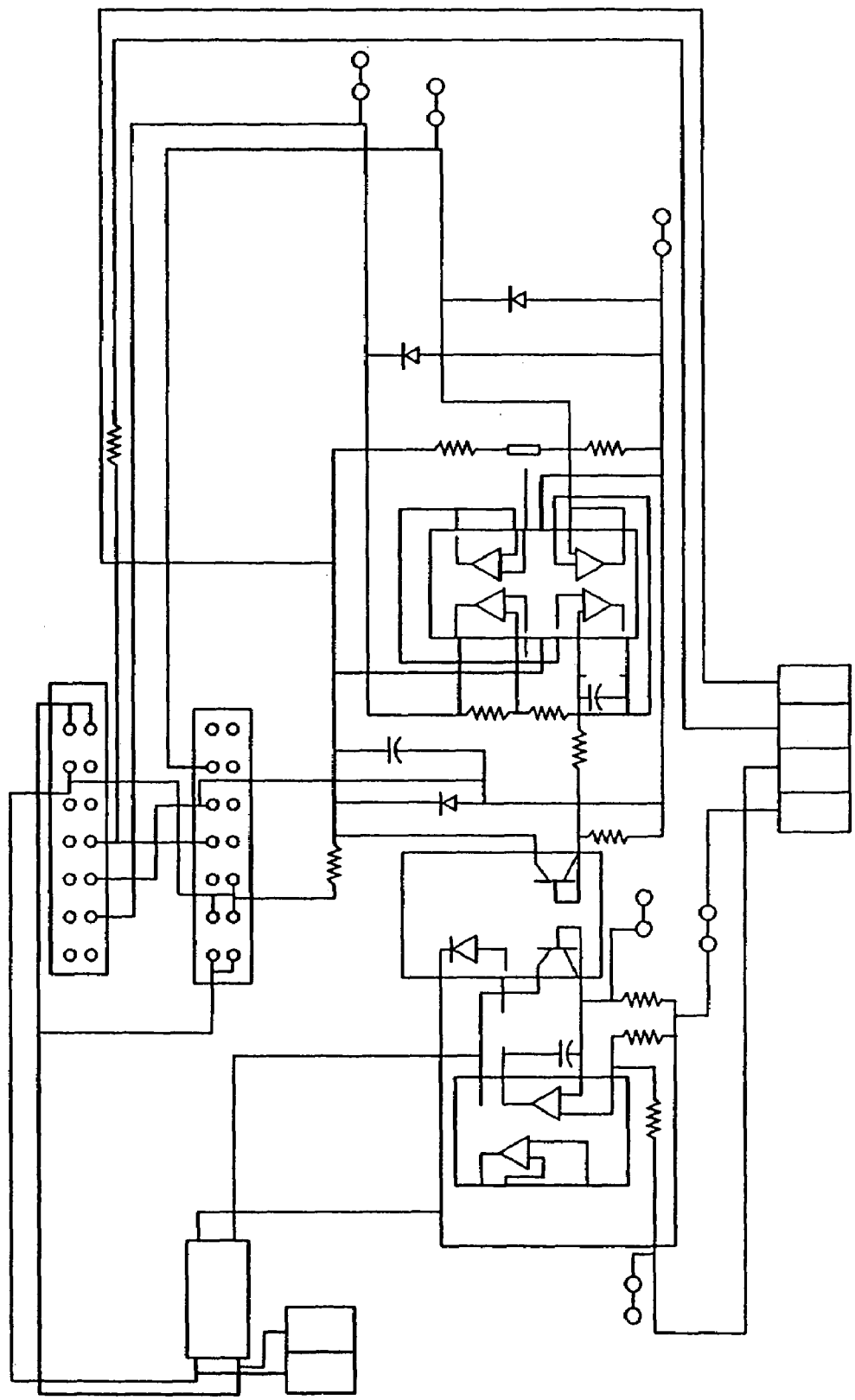
FIG. 1 is a schematic of a high voltage control board layout.

One embodiment of the present invention provides an automated, self-contained, flow apparatus for encapsulating allosteric compounds or compositions, such as inositol hexaphosphate, in cells or fragments of cells, including, but not limited to, red blood cells, white blood cells, platelets, stem cells, genetically engineered stem cells, or an expanded population of stem cells. In one embodiment, the apparatus of the present invention combines the features of a plasmaphoresis apparatus with those of a flow electroporation apparatus to form an automated, self-contained flow electroporation device. The present invention further comprises a new flow electroporation chamber that allows use of the chamber under flow rather than static conditions. It is contemplated that the method and apparatus, including the electroporation chamber of the present invention, may be used to encapsulate a variety of biologically active substances in diverse cell populations.

In one embodiment, the present invention provides a population of modified cells having characteristics that make the cells particularly useful for treating conditions that demand or benefit from an increase in the delivery of oxygen to the tissues. In accordance with the method of the present invention, a homogenous population of IHP loaded red blood cells can be obtained under sterile conditions and with a reduced propensity to lyse following encapsulation. The treated red blood cells exhibit normal life spans in circulation. Using the present invention, red blood cells of a patient in need of the treatment can be quickly loaded and returned to the patient's circulation.

The method of operation of the apparatus of the present invention is described below with reference to the preferred use of the apparatus, i.e., the encapsulation of allosteric effectors of hemoglobin in red blood cells. Inositol hexaphosphate is the preferred allosteric effector to be used with the present invention. Other sugar phosphates, such as inositol pentaphosphate, inositol tetraphosphate, inositol triphosphate, inositol diphosphate and diphosphatidyl inositol diphosphate, can also be used. Other suitable allosteric effectors include polyphosphates such as nucleotide triphosphates, nucleotide diphosphates, nucleotide monophosphates, and alcohol phosphate esters. In case of certain mutations of hemoglobin, e.g. "Zurich" hemoglobin, organic anions such as polycarboxylic acids can be used as allosteric effectors. Finally, it is possible to use inorganic anions such as hexacyano ferrate, phosphate or chloride as allosteric effectors.

The uses of IHP-treated red blood cells is quite extensive including the treatment of numerous acute and chronic conditions including, but not limited to, hospitalized patients, cardiovascular operations, chronic anemia, anemia following major surgery, coronary infarction and associated problems, chronic pulmonary disease, cardiovascular patients, autologous transfusions, as an enhancement to packed red blood cells transfusion (hemorrhage, traumatic injury, or surgery), congestive heart failure, myocardial infarction (heart attack), stroke, peripheral vascular disease, intermittent claudication, circulatory shock, hemorrhagic shock, anemia and chronic hypoxemia, respiratory alkalemia, metabolic alkalosis, sickle cell anemia, reduced lung capacity caused by pneumonia, surgery, pneumonia, trauma, chest puncture, gangrene, anaerobic infections, blood vessel diseases, such as diabetes, substitute or complement to treatment with hyperbaric pressure chambers, intra-operative red cell salvage, cardiac inadequacy, organ transplant, carbon monoxide, nitric oxide, and cyanide poisoning.

Treating a human or animal for any one or more of the above disease states is done by transfusing into the human or animal between approximately 0.5 and 6 units (1 unit=453 ml±50 ml) of IHP-treated blood that has been prepared according to the present invention. In certain cases, there may be a substantially complete replacement of all the normal blood in a patient with IHP-treated blood. The volume of IHP-treated red blood cells that is administered to the human or animal will depend upon the indication being treated. In addition, the volume of IHP-treated red blood cells will also depend upon concentration of IHP-treated red blood cells in the red blood cell suspension. It is to be understood that the quantity of IHP red blood cells that is administered to the patient is not critical and can vary widely and still be effective.

IHP-treated packed red blood cells are similar to normal red blood cells except that the IHP-treated packed red blood cells can deliver 2 to 3 times as much oxygen to tissue per unit of blood when compared to normal, untreated red blood cells. A physician would therefore chose to administer a single unit of IHP-treated packed red blood cells rather than 2 units of the normal red blood cells. IHP-treated packed red blood cells could be prepared in blood processing centers analogously to the present blood processing methods, except for the inclusion of a processing step where the IHP is encapsulated in the cells.

Red blood cells that have been loaded with inositol hexaphosphate according to the present invention can be used to treat a wide variety of diseases and disease states. The IHP loaded red blood cells made according to the present invention can be administered to a patient undergoing a heart attack thereby increasing the oxygen delivery to the ischemic heart tissue and, at the same time, reducing the cardiac output. The IHP-loaded red blood cells made according to the present invention also can be used to treat any ischemic condition including, but not limited to, "bleeding" anemia, surgical complications, stroke, diabetes, sickle cell disease, bums, intermittent claudication, emphysema, hypothermia, peripheral vascular disease, congestive heart failure, angina, transient ischemic disease, disseminated intravascular coagulation, adult respiratory distress syndrome (ARDS) and cystic fibrosis.

The present invention includes a method of treating a patient in need of tissue oxygenation comprising administering to the patient an effective amount of red blood cells containing a quantity of IHP sufficient to cause a right shift in the oxygen dissociation curve of the hemoglobin associated with the red blood cells. The present invention also includes a method of treating a patient in need of a therapeutic agent comprising administering to the patient an effective amount of red blood cells containing the therapeutic agent.

In one embodiment of the present invention, substances or drugs can be introduced into cells or fragments of cells such as platelets. For example, thrombus-dissolving substances such as tissue plasminogen activator, urokinase or streptokinase and the like can be introduced into a population of platelets. Tissue plasminogen activator is sold under the trademark ACTIVASE® by Genentech Corporation, South San Francisco, Calif. These platelets loaded with the thrombus dissolving substances can be then introduced into a patient who is suffering from a thrombus blocking a blood vessel. The platelet containing the thrombus dissolving substance will then migrate to the site of the thrombus and attach itself to the thrombus. Because the treated platelets contain active thrombus dissolving enzymes, the thrombus is then dissolved. It is to be understood that other drugs can be introduced into the platelets or other cells for delivery to damaged tissue. These drugs include, but are not limited to, antibiotics, smooth muscle inhibitors, antifungal agents, antibacterial agents, antiviral agents, chemotherapeutic agents and the like. Antiangiogenic drugs can be incorporated into the platelets. Antiangiogenic drugs include, but are not limited to, AGM-1470 (TNP-470) or antagonists to one of its receptors, MetAP-2; growth factor antagonists, or antibodies to growth factors (including VEGF or bFGF); growth factor receptor antagonists or antibodies to growth factor receptors; inhibitors of metalloproteinases including TIMP, batimastat (BB-94), and marimastat; tyrosine kinase inhibitors including genistein and SU5416; integrin antagonists including antagonists alphaVbeta3/5 or antibodies to integrins; retinoids including retinoic acid or the synthetic retinoid fenretinide; steroids 11α-epihydrocortisol, corteloxone, tetrahydrocortisone and 17α-hydroxyprogesterone; protein kinase inhibitors including staurosporine and MDL 27032; vitamin D derivatives including 22-oxa-1 alpha, and 25-dihydroxyvitamin D3; arachidonic acid inhibitors including indomethacin and sulindac; tetracycline derivatives including minocycline; thalidomide and thalidomide analogs and derivatives; 2-methoxyestradiol; tumor necrosis factor-alpha; interferon-gamma-inducible protein 10 (IP-10); interleukin 1 and interleukin 12; interferon alpha, beta or gamma; angiostatin protein or plasminogen fragments; endostatin protein or collagen 18 fragments; proliferin-related protein; group B streptococcus toxin; CM101; CAI; troponin I; squalamine; nitric oxide synthase inhibitors including L-NAME; thrombospondin; wortmannin; amiloride; spironolactone; ursodeoxycholic acid; bufalin; suramin; tecogalan sodium; linoleic acid; captopril; irsogladine; FR-118487; triterpene acids; castanospermine; leukemia inhibitory factor; lavendustin A; platelet factor-4; herbimycin A; diaminoantraquinone; taxol; aurintricarboxylic acid; DS-4152; pentosan polysulphite; radicicol; fragments of human prolactin; erbstatin; eponemycin; shark cartilage; protamine; Louisianin A, C and D; PAF antagonist WEB 2086; auranofin; ascorbic ethers; and sulfated polysaccharide D 4152. The agents, including thrombus dissolving substances, can be introduced into the platelets by a variety of methods with the most preferable method being according to the apparatus of the present invention as described herein.

The present invention also includes a method of treating a patient in need of a therapeutic agent comprising administering to the patient an effective amount of platelets containing the therapeutic agent.

Patients that can be treated with the modified platelets include, but are not limited to, heart attack patients, patients suffering a stroke, and any patient that is suffering from an embolism. The amount of thrombus dissolving substance that is introduced into a platelet is between 0.01 μg to 1 mg per platelet. Generally speaking, one loads as much thrombus dissolving substance as possible into a population of platelets. The method of introducing the thrombus dissolving substance into the platelets is similar to the method of introducing IHP into red blood cells as described herein.

The present invention also includes methods and compositions for delivering bioactive compounds to the body by loading red blood cells, white blood cells and/or platelets with agents including, but not limited to, cytokines, such as inteferon, colony stimulating factors, and interleukins; hormones, such as growth hormone, insulin, and prolactin; antibodies, including monoclonal antibodies and polyclonal antibodies as well as antibodies conjugated to toxins or radioactive agents, chemotherapeutic agents, such as doxirubicin, amphotericin, and taxol, bioactive peptides, and antiviral agents.

Another embodiment of the present invention is the targeting of therapeutic agents to certain locations in the body by loading a particular cell with a therapeutic agent or agents. Examples of this embodiment include, but are not limited to, loading of platelets with an antiangiogenic agent that will be targeted to a site that has been treated mechanically to remove an atherosclerotic plaque (as in angioplasty) and loading of leukocytes with antibiotics that migrate to a site of an infection.

The present invention includes a method of gene therapy including, but not limited to the introduction of deoxyribonucleic acid and ribonucleic acid preparations into live cells. The DNA and/or RNA preparations preferably code for a desired protein or fragment of a protein and the DNA can optionally contain vectors that will facilitate the introduction of the DNA into the genetic mechanisms of the cell and thereby increase the expression of the desired protein. These methods of adding vectors to naked DNA preparations are well know to those of ordinary skill in the art. The DNA that is introduced using the flow electroporation apparatus of the present invention can be naked DNA or can contain other agents to facilitate entry of the DNA into the cell.

The present invention can be used to introduce any genetic material into a cell or cell fragment. The genetic material may code for a specific protein or peptide or may be an antisense genetic material. Examples of proteins and peptides that can be introduced into human or animal cells by introducing a nucleic acid or the expression vector that codes for that protein or peptide include, but is not limited to, genes that code for b-cell differentiation factors, b-cell growth factors, mitogenic cytokines, chemotactic cytokines, colony stimulating factors, angiogenesis factors, adhesion factors (cadherins, selectins, inteegrins, NCAMs, ICAMs, and L1) t-cell replacing factors, differentiation factors, transcription factors, mRNA, heat shock proteins, nuclear protein complexes, and RNA/DNA oligomers. Specific factors that can be introduced into a human or animal using the flow electroporation system of the present invention include, but are not limited to, IFN-alpha, IFN-beta, IFN-omega, IL1, IL2, IL3, IL4, IL5, IL6, IL7, IL8, IL9, IL10, IL11, IL12, IL13, IL14, IL15, IL16, IL17, IL18, leptin, myostatins (growth differentiation factors), macrophage stimulating protein and derivatives thereof, platelet-derived growth factor, tumor necrosis factors (TNF-alpha, TNF-beta, NGF, CD40L, CD137L/4-1BBL, human lymphotoxin-beta, TNF-related apoptosis-inducing ligand (trail)), monoclonal antibodies, G-CSF, M-CSF, GM-CSF, PDGF, IL1-alpha, IL1-beta, FGF IFN-gamma, IP-10, PF4, GRO, and 9E3, erythropoietin (EPO), endostatin and fragments thereof, angiostatin and fragments thereof, fibroblast growth factors (FGF), VEGF, soluble receptors and any fragments or combinations thereof.

The present invention of transfecting cells by electroporation, preferably flow electroporation, is capable of achieving transfection efficiencies of greater than 40%, preferable greater than 50% and most preferably greater than 60% or 70%. Transfection efficiency can be measured either by the percentage of the cells that express the product of the gene or the secretion level of the product express by the gene. The cells maintain a high viability during and after the electroporation process. Viability is routinely more than 50% or greater. Preferably, viability is greater than 60%, more preferably greater than 70%, more preferably greater than 80%, more preferably greater than 90%.

Another advantage of the present invention is the speed at which a large population of cells can be transfected. For example, a population of lymphocytes can be transfected by electroporation by electroporating the sample in less than 5 hours, preferably less than 4 hours and most preferable in less than 3 hours and most preferably in less than 2 hours. The time of electroporation is the time that the sample is processed by the flow electroporation process.

Description of Flow Electroporation Device

The flow electroporation device of the present invention is, in one embodiment, comprised of the following:
  Instrument (electronics module [power box+tower]);
  Computer (communicates with electronics module);
  Monitor (displays graphical user interface [GUI] and enables user interaction); and
  Disposable Set (component in which flow electroporation of cell suspension occurs.

The present invention uses flow electroporation to overcome the practical limitations in respect to the number of cells that can be electroporated, the time in which they can be electroporated and the volume of solution in which they are suspended that attend to static or batch electroporation methods. With this method, a cell suspension is passed across parallel bar electrodes that are contained in a flow cell that is preferably disposable. It is to be understood that different configurations of flow cells can be used in the present invention. For example, see below. During this passage, the cells are subjected to electrical pulses with predetermined characteristics. For example, the specific settings for preparation of IHP-loaded red blood cells are: voltage, 750V; pulse width, 650 μsec; time between pulses, 100 μsec; 2 biphasic pulses in a burst; time between bursts, 12 sec; flow rate, 0.05 mL/sec. The molecule of interest (e.g., IHP) then diffuses into the cell following concentration and/or electrical gradients. The present invention is optionally capable of subjecting the cells to a range of electric field strengths. Generally speaking, field strengths useful in the present invention are greater than approximately 1 kV/cm; preferably, approximately 1 kV/cm to 3.5 kV/cm.

The process is initiated by attaching the flow cell with solutions and cell suspensions in the containers with the necessary fluids and samples. The flow cell snaps into place and is secured by closing a hinged panel. Priming solution (saline) and cell suspension are introduced by providing the required commands to the electroporation system, which controls operation of the pump and pinch valves. As the cells transit the flow path between electrodes, electric pulses of the chosen voltage, duration, and frequency are applied. Product and waste fluids are collected in the designated containers.

The user inputs the desired voltage and other parameters into the flow electroporation system of the present invention. As noted above, a range of settings is optionally available. The computer communicates to the electronics in the tower to charge the capacitor bank to the desired voltage. Appropriate switches then manipulate the voltage before it is delivered to the flow path to create the electric field (the switches provide alternating pulses or bursts to minimize electrode wear brought on by prolonged exposure to the electric field). The voltage is delivered according to the duration and frequency parameters set into the flow electroporation system of the present invention by the operator. The flow electroporation system of the present invention is now described in detail.

Electronics Module

This section describes how the various components of the electronics module interface with each other in one embodiment of the present invention. Details for all the mechanical and electrical components in the electronics module are included on Tables 1 and 2 below.

TABLE 1

Mechanical Components

| COMPONENT | DESCRIPTION/FUNCTION | MANUFACTURER | PART NUMBER |
|---|---|---|---|
| POWER CABINET ASSY | PLASTIC PANELS THAT HOUSE THE 24-VOLT POWER SYSTEM | NICHOLSON PRECISION INSTRUMENTS (NPI) | 1SP00001100AD |
| TOWER CABINET ASSY | PLASTIC PANELS THAT HOUSE MOST OF THE ELECTRONICS, PUMP, COOLER, HIGH VOLTAGE SUPPLY | NPI | 1ST00001200AD |
| SYSTEM BOARD GUIDE | POLYCARBONATE PIECE THAT GUIDES THE PHYSICAL POSITION OF THE SYSTEM BOARD IN THE TOWER ASSY | NPI | 1ST08101100PD |
| SYSTEM BOARD SLIDE | POLYCARBONATE PIECE THAT ENSURES THE SYSTEM BOARD IS LEVEL FOR PROPER CONNECTION | NPI | 1ST08101100PD |
| SYSTEM BOARD SCREW MOUNT | POLYCARBONATE FIXTURES THAT SECURE SYSTEM BOARD TO TOWER | NPI | 1ST08301100PD |
| MECHANICAL SWITCH WITH BRACKET | SWITCH THAT WHEN ACTIVATED SIGNALS THE SYSTEM THAT HIGH VOLTAGE PULSES MAY BE DELIVERED TO DISPOSABLE | MANUFACTURER MICRO SWITCH DISTRIBUTOR MOUSER | 1ST09001100PD |
| DRIP TRAY + CURRENT MONITOR BRACKET | POLYCARBONATE COMPONENT THAT COLLECTS ANY FLUID THAT MAY DRIP FROM THE PELTIER COOLER, USUALLY IN THE FORM OF CONDENSATION IT ALSO SUPPORTS THE CURRENT MONITOR USED FOR DISPLAYING THE CURRENT DRAWN THROUGH THE DISPOSABLE SET | NPI | 1ST09201100PD |
| ALUMINUM FRAME | FRAME FOR THE INSTRUMENT | ITEM PRODUCTS | 1ST10001100SA |
| INFRARED (IR) HOUSING | BLACK DELRON HOUSING THAT HOLDS THE IR DETECTOR AS WELL AS TUBING FOR TEMPERATURE MEASUREMENT | NPI | 1ST03201000PD |
| COMPRESSION PLATE | POLYCARBONATE PANEL THAT COMPRESSES THE DISPOSABLE FLOW CELL TO PREVENT AIR OR FLUID LEAKAGE | NPI | 1ST04101100PD |
| HEAT SINK | ALUMINUM PLATE THAT PROVIDES MEANS FOR REMOVING HEAT FROM HIGH VOLTAGE SWITCHES | NPI | 1ST10101100PD |
| COMPRESSION PLATE LATCHES | LATCHES USED TO LOCK COMPRESSION PLATE ON TO DISPOSABLE FLOW CELL | MCMASTER CARR | 1ST08301100PD |

TABLE 2

Electrical Components

| COMPONENT | DESCRIPTION | MANUFACTURER PART# | THERAMED PART# |
|---|---|---|---|
| HIGH VOLTAGE (HV) POWER SUPPLY | BIPOLAR SUPPLY PROVIDING 125 WATTS AT A MAXIMUM OF 1000 V DESIGNED WITH A FLOATING GROUND FOR SAFETY | ULTRA VOLT ½C24-NP125 | 1ST201100PD |
| PINCH VALVES | ACTUATE TO OCCLUDE TUBING FROM DISPOSABLE SETS | ASCO/ANGAR 401139 | 1ST01201100PD AND 1ST04401100PD |
| PERISTALTIC PUMP | STEPPER MOTOR, PUSHES FLUID THROUGH DISPOSABLE SET | CAVRO SP-4/724439 | 1ST04501100PD |
| PELTIER COOLER WITH FAN | REMOVES HEAT FROM DISPOSABLE SET CONTROLLED BY TEMPERATURE SENSOR AND SOFTWARE | TE TECHNOLOGIES CP-2061 | 1ST04801100PD |
| 300 A SWITCHES | CONNECTS HIGH VOLTAGE SYSTEM TO ELECTRODE CONTACT POINTS SOFTWARE CONTROLLED | POWEREX PM300DSA120 | 1ST10201100PD |

TABLE 2-continued

Electrical Components

| COMPONENT | DESCRIPTION | MANUFACTURER PART# | THERAMED PART# |
| --- | --- | --- | --- |
| 150 A SWITCHES | CONNECTS HIGH VOLTAGE SYSTEM TO ELECTRODE CONTACT POINTS WHEN ENERGY REDUCTION PULSES ARE USED (SEE GRAPHICAL USER INTERFACE [GUI] SECTION) SOFTWARE CONTROLLED | POWEREX PM150DSA120 | 1ST10301100PD |
| CURRENT LIMITING RESISTORS | 330 Ω RESISTOR THAT LIMIT THE AMOUNT OF CURRENT THAT THE HIGH VOLTAGE SYSTEM CAN DELIVER TO THE CAPACITOR BANK | VISHAY DALE 71-RH50-330 | 1ST10401100PD |
| ENERGY REDUCTION RESISTORS | 5 Ω BLEED OFF RESISTORS THAT CAUSE MORE RAPID DISCHARGE OF CAPACITORS DURING ENERGY REDUCTION PULSES | VISHAY DALE 71-RH50-10K | 1ST10501100PD |
| LOW PASS FILTER | 2 UF CAPS THAT PREVENT HIGH FREQUENCY NOISE FROM EFFECTING HIGH VOLTAGE SWITCHES | CORNELL DUBLIER SCD205K122A3Z25 | 1ST05001100PD |
| MINI MEGA PACK | PROVIDES POWER FOR ENTIRE SYSTEM THROUGH TWO 24 VOLT POWER SUPPLIES AND TWO BOOSTERS PROVIDING 83 AMPS EACH | VICOR MM2-14517 | 1P0511100PD |
| IR SENSOR | INFRARED TEMP SENSOR THAT MONITORS THE FLUID TEMPERATURE EXITING THE FLOW CELL | OMEGA 0S36-01-K-80F | 1ST03101100PD |
| INDICATOR LIGHT | ACTIVATES WHEN THE MECHANICAL SWITCH IS ACTIVATED THIS ALSO SIGNALS THE SYSTEM THAT HIGH VOLTAGE PULSES ARE CAPABLE OF BEING DELIVERED TO THE DISPOSABLE | DISTRIBUTOR MOUSER 604-L531T | 1T0341100PD |
| HIGH VOLTAGE CAPACITORS | STORE ENERGY FOR HIGH VOLTAGE PULSES EACH CAP IS RATED FOR 350 V AND 1000 UF | MALLORY CGH102T350V2L | 1ST06101100PD |
| CURRENT MONITOR | HALL EFFECT CURRENT SENSOR THAT MEASURES DC CURRENTS THROUGH INDUCTION OF CURRENT ON ITS COILS VIA THE MAGNETIC FIELD GENERATED MEASURES UP TO 300 AMPS TURN RATIO OF 12000 PROVIDING A NOMINAL ANALOG OUTPUT CURRENT OF 150 MA | F W BELL CLN-300 | 1T0711100PD |
| AC SYSTEM RELAY | PROVIDES GATE FOR AC POWER TO SYSTEM | CRYDOM CTD2425 | 1P0521100PD |
| DC COOLER RELAY | PROVIDES GATE FOR DC POWER TO PELTIER COOLER | CRYDOM DID40 | 1P0541100PD |
| DC HIGH VOLTAGE RELAY | PROVIDES GATE FOR POWER TO HIGH VOLTAGE SUPPLY | CRYDOM DID40 | 1P0551100PD |
| HIGH VOLTAGE CONTROL BOARD | USES COMPUTER D/A VOLTAGE TO CONTROL BOTH HV SUPPLIES AND PROVIDE FOR HV ISOLATION FROM GROUND | EMDS/ECA | 1E0101100PD |
| CAPACITOR BOARD | HOLDS HIGH VOLTAGE SWITCHES, CURRENT LIMITING RESISTORS, LOW PASS FILTERS, AND HIGH VOLTAGE CAPS | EMDS | 1E0201100PD |
| ER BOARD | CLOSES CIRCUIT WITH ENERGY REDUCTION RESISTORS AND 150 A SWITCHES FOR RAPID DISCHARGE OF CAPACITORS PROVIDES OPTICAL ISOLATION FOR PULSES BETWEEN THE COMPUTER AND TO HV MODULATOR SWITCHES | EMDS/ECA | 1E0301100PD |
| PULSE MODULATION BOARD | CLOSES CIRCUIT WITH 300 A SWITCHES FOR DISCHARGE OF CAPACITORS DURING NORMAL PULSING PROVIDES OPTICAL ISOLATION FOR PULSES BETWEEN THE COMPUTER AND TO HV MODULATOR SWITCHES | EMDS/ECA | 1E0401100PD |
| SYSTEM BOARD | MAIN CONTROL BOARD FOR FLOW ELECTROPORATION DEVICE [VERSION 10] SYSTEM CONTAINS CIRCUITRY FOR CONTROLLING PINCH VALVES, WATCHDOG, HIGH VOLTAGE PULSE CREATION, FLUID DETECTOR CONTROL, AND HIGH VOLTAGE SIGNAL MEASUREMENT CONTAINS OPTICAL ISOLATION CIRCUITRY FOR HIGH VOLTAGE SUPPLY AND FLUID DETECTOR IF HIGH VOLTAGE DIFFERENTIAL > 20 V SYSTEM WILL BE SHUT DOWN | EMDS/ECA | 1E0501100PD |
| COMPUTER | DIRECT CONNECTION TO PERISTALTIC PUMP THROUGH RS232 PORT, AND SYSTEM CONTROL BOARD THROUGH KPC13104 CABLE FROM KPCI A/D BOARD IN PCI SLOT | ICS ADVENT 400-H53 | 1C0101100PD |

TABLE 2-continued

Electrical Components

| COMPONENT | DESCRIPTION | MANUFACTURER PART# | THERAMED PART# |
|---|---|---|---|
| MONITOR | DISPLAYS GUI AND ALLOWS FOR USER INTERACTION AND CONTROL OF GUI PARAMETERS LISTED IN FOLLOWING SECTIONS | DELL 0532U | 1C0301100PD |
| DATA ACQUISITION CARD | INPUT/OUTPUT FROM COMPUTER TO SYSTEM CONTROL BOARD | KEITHLEY KPCI-3104 | 1C0501100PD |
| ROCKER SWITCH | PROVIDES 24 VOLTS TO SYSTEM | MOUNTAIN SWITCH 10DS322 | 1P0321100PD |
| TOP FAN | COOLS UNIT | NMB 4715KL-05W-B30 | 1ST03501100PD |
| COOLER PLATINUM SENSOR | PROVIDES TEMPERATURE FEEDBACK TO COMPUTER FROM THE PELTIER COOLER | OMEGA SRTD-1 | 1ST04701100PD |

FIGS. 1–4 provide layouts/diagrams of the high voltage system, system board, and pulse modulator and energy reduction modulator boards. The electronics module can be divided into two parts, the power box and the tower. The module requires a 15 A outlet to supply AC power. This power is taken in through the power box and delivered to a 250V/10 A fuse and an illuminated rocker switch. The "ON" illuminated position of the rocker switch permits the passage of power to the System AC solid-state relay. A relay acts as a gate for the power. The gate can only be opened by the correct logic signal. The correct logic signal here is the "watchdog" signal, which is generated by activation of the FED Version 1.0 software. The watchdog signal was created to circumvent potential hazards to the user from the electronics module in the event the software may not be functioning. Without the watchdog signal, no electronic component in the electronics module will function.

The gated AC power is then converted into DC power and regulated by a Mini MegaPAC. Internally, the Mini Mega-PAC (Vicor Corporation, Andover, Mass.) has two isolated 24V power supplies and two 24V power boosters. The two boosters are attached to only one of the 24V isolated supplies. This trio is the power supply that supplies power to the entire system with the exception of the high voltage power supply. The remaining isolated 24V power supply in the Mini MegaPAC supplies power only to the high voltage power supply in the tower. This separation is an intentional design feature that creates a floating ground for the high voltage pulses, which minimizes potential hazards to the user. The user would have to touch both a point of high voltage and the floating ground to be harmed by the instrument.

With respect to the Mini MegaPAC, power is transferred from the power supplies to the individual electronic components via an umbilical cord connecting the power box to the tower. Two paths of power from the Mini MegaPAC have additional relays. The power to the cooler is gated by software control. Activation of the cooler depends upon the cooler set temperature determined by the user and the corresponding software algorithm used to regulate cooler temperature. The power to the high voltage supply system is gated by the micromechanical switch in the tower, which confirms proper alignment of the disposable set on the instrument. Without a properly attached disposable set, the high voltage system is disabled. The high voltage system is composed of an Ultravolt bipolar high voltage power supply, a capacitor bank, two 330 ohm current limiting resistors, two 150 A switches, two 300 A switches, two 5 ohm energy reduction resistors, two low pass filters, the capacitor board, and the high voltage control board.

Figure 2:
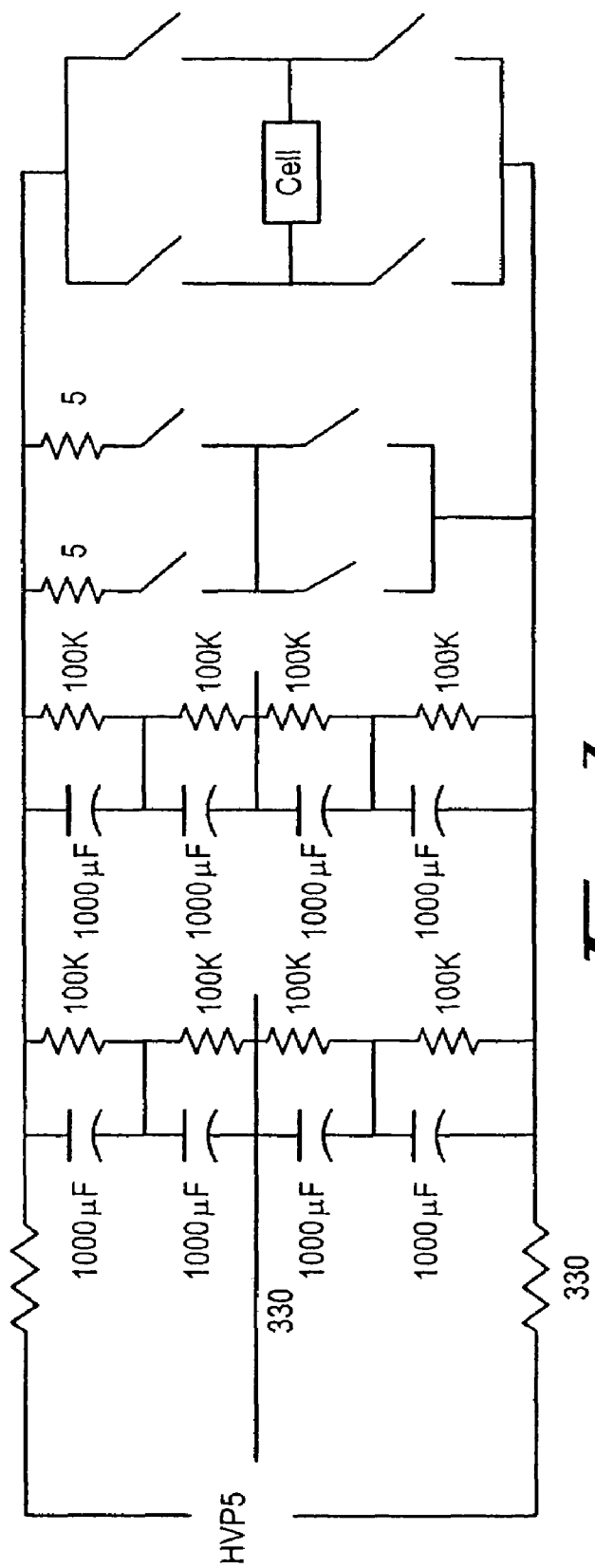
FIG. 2 is a schematic diagram of a high voltage system diagram.
Figure 1:
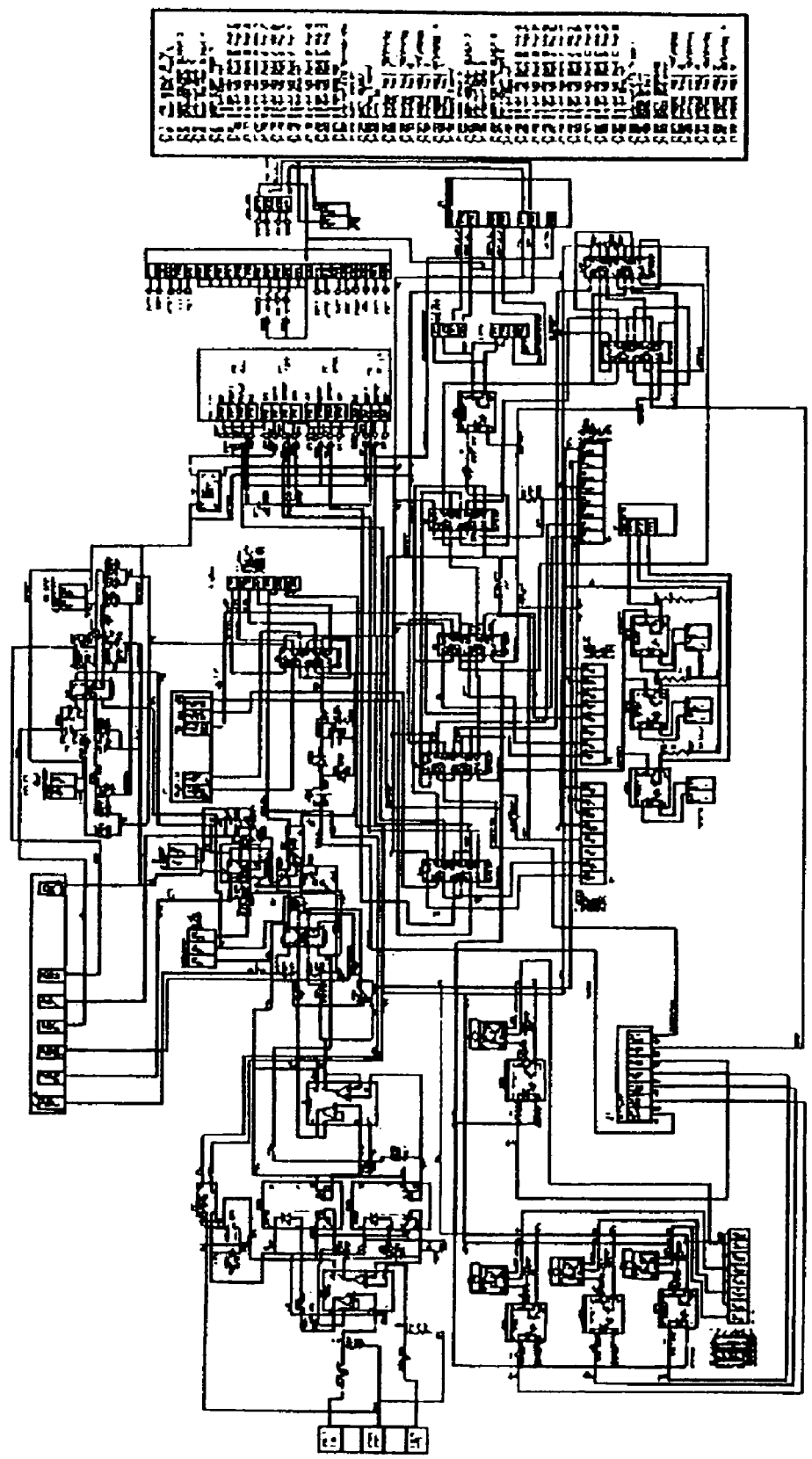

FIGS. 1 and 2 better illustrate the high voltage system and the components that comprise this system. FIG. 1 is the high voltage control board layout. This board controls and synchronizes the two bipolar 500V voltage supplies that lie within the Ultravolt high voltage supply. Together the control board and these supplies can produce up to 1000V at alternating polarity. FIG. 2 is an overview of how the pulses are generated by the capacitor bank and manipulated by switches to produce the alternating pulses. The energy reduction switches are also included in this figure. When activated, the energy reduction reduces the charge generated by the capacitors through its own set of resistors and switches. Finally, the manipulated pulses are delivered to the disposable set through low gauge stranded copper wires. To minimize the potential hazard to the user, the entire high voltage system is fed by an isolated power supply to create a floating ground, which is separate from the common ground shared by the rest of the instrument.

The remaining electronics components are fed from the boosted 24V power supply. The pinch valves, tower fan, and pump are activated and initialized when the flow electroporation system of the present invention is on (electronics module and software). This power supply also supplies voltage to the following three printed circuit boards: the pulse modulator board, the energy reduction modulator board, and the system board. The system board is the communication terminal between the computer and the instrument. FIG. 3 displays the general layout of the system board. It is connected to an A/D card in the computer via cable. The system board interfaces with both the high voltage system and the main power supply. The board maintains the isolation between these two systems.

The system board and the computer A/D card in the computer communicate through analog and digital signals. The system board receives analog signals from components, processes them, and relays the information back to the computer. Signals processed this way are analog inputs. Analog inputs on the system board include the high voltage, current, infrared temperature, and cooler temperature. The transfer of analog information also flows in the opposite direction, which is called analog output. Analog outputs on the system board include the control voltage in the high voltage system, +5V supply, an analog ground, and an A/D trigger. The control voltage in the high voltage system is the signal the computer generates to tell the high voltage system what voltage to attain in order to give the desired output voltage. Any signals related to the high voltage system are optically isolated electronically to preserve the isolation of the high voltage power supply. The A/D trigger is the signal the computer generates to gate the pulses to the desired length.

Digital signals from the computer can be communicated to the instrument via the system board. These signals are processed, manipulated with logic circuitry, and delivered to the electronic component they control. This is known as digital output. Operation of the pinch valves, the watchdog, the cooler, biphasic or monophasic pulses, and the level of energy reduction is under digital output control. This transfer of digital signals can also be sent from the system board to the computer and is known as digital input. The remainder of the system board is logic circuitry used to manipulate the four counter timers available on the computer A/D card to generate the waveforms desired by the user.

Figure 4:
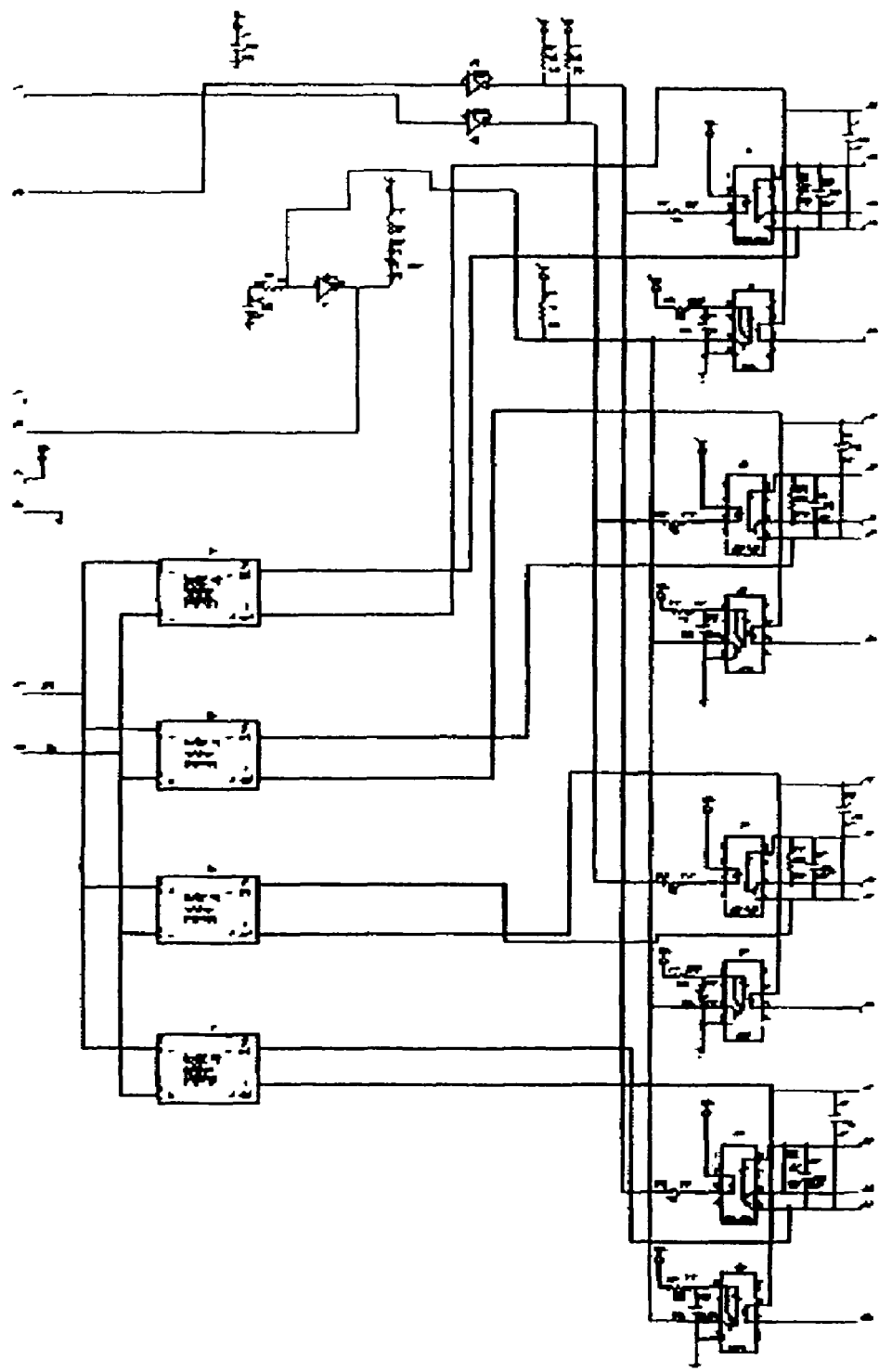
FIG. 4 is a schematic diagram of a pulse modulator and energy reduction modulator board general layout.
Figure 5:
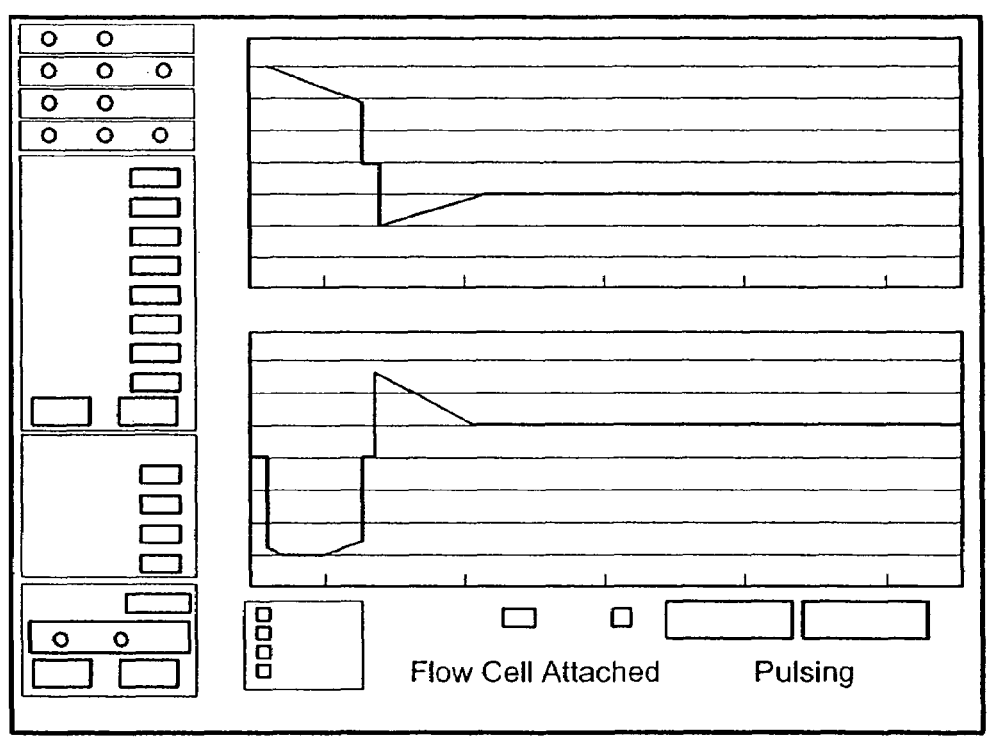
FIG. 5 is a pictorial representation of the Graphical User Interface During IHP/RBC Preparation.

The system board also interfaces with the pulse modulator board and the energy reduction modulator board. Both modulator boards contain identical circuitries but are not interchangeable due to incongruent connections between the 300 A pulse switches and the 150 A switches. FIG. 4 displays the general layout of the pulse modulator board and energy reduction modulator board. The system board feeds the signal from the generated waveform to the modulator boards. The modulator boards drive the switches to produce the desired waveform.

The mechanical framework of the electronics module is primarily polycarbonate, acrylic, and aluminum. Aluminum was chosen based on it weight and ability to transfer heat. Polycarbonate was chosen based on its high strength and easy machinability. Acrylic was used primarily for the drip tray and the shaped base plate for the instrument. Advantages of acrylic are that it is lightweight and that two separate pieces of acrylic can be chemically bonded. It is to be understood that the materials used are not critical to the present invention. The components discussed in the text are listed in Tables 1–5.

Computer and Monitor

The main function of the computer and monitor is to enable the user to communicate with the electronics module. Communication is made possible through a data acquisition card in the PCI slot of the computer. The data acquisition card is a Keithley KPCI-3104 containing 16 single-ended analog input channels or 8 differential analog input channels, two 8 bit digital ports programmable as inputs or outputs, one 7 bit digital I/O programmable port, and four programmable user counter/timers.

The system software and its subsequent versions were created in Visual Basic as a method of communication with the Keithley card. The software contains a Graphical User Interface (GUI) displayed on the monitor, which facilitates the communication between user and electronics module. Traces displaying the voltage and current on the GUI give the user real-time updates on the current run. In addition to communicating through the Keithley card, a communication port (COM port) on the computer is used to communicate with the peristaltic pump in the electronics module via an RS232 port.

The monitor displays the GUI. The GUI presents the various settings used for the flow electroporation process. Table 3 below provides an overview of the GUI settings.

TABLE 3

GUI Settings

| Item | Description | Operational Range |
|---|---|---|
| High voltage | This entry on the screen establishes the sum of the voltages that are generated by two high voltage supplies connected in series The software program commands this voltage when the "ON" button in the pulse control section of the GUI is depressed The high voltage supply is returned to zero at the completion of the indicated number of "Pulse Bursts" or the depression of the "OFF" button The voltage is controlled through an isolated high voltage control board that converts a single analog control voltage from the KPCI-3104 into a pair of complementary control voltages required by the high voltage supplies. | 0–1000 V |
| Monophasic/biphasic | Determines whether the pulses in a burst are of the same polarity or alternating polarity. Internally the system always generates the pulses necessary to provide for biphasic pulses If the biphasic mode is chosen the biphasic pulses are passed to the high voltage modulator switches In monophasic mode, one modulator switch is prevented from receiving modulator pulses The visual basic program controls the flow of pulses through the System Control Board by means of a digital bit in the KPCI-3104. | Option buttons mono or biphasic choice. |
| First pulse | Determines polarity of first pulse in a burst The software controls the flow of pulses through the System Control Board by a digital bit in the KPCI-3104. Taken in combination with the previous Monophasic/biphasic option buttons, it is possible to generate a wide set of possible pulse configurations. | Option button Positive or negative choice |
| Pulse width | Determines width of applied pulses by means of a counter timer located in the KPCI-3104 An integer number determines the pulse width in microseconds This number is related to the number of cycles of a clock that are counted for the pulse width and the interval between pulses. The internal system clock on KPCI-3104 operates at 20 MHz, which limits the system to approximately 1600 microseconds for a maximum pulse width including interval between pulses An external clock is included on the System Control Board, which operates at 2 MHz thus permitting a 10X multiplier of the total period. The time constant of these pulses is determined primarily by two parallel banks of the 4X1000 uF capacitors in series and buffer conductivity within the disposable set. In monophasic mode the pulse width must be less than the selected time between pulses | User input 15 μsec–6,000 μsec (using 10X multiplier) |

TABLE 3-continued

GUI Settings

| Item | Description | Operational Range |
|---|---|---|
| Time between pulses | Determines time between pulses in a burst In monophasic mode the time between pulses must be greater than the selected pulse width. | 15 μsec–6,000 μsec (using 10X multiplier) including pulse width |
| Pulses in burst | Determines number of pulses in each burst by input of positive whole numbers Limitations are based on the number of pulses, time between pulses, and desired pulse width. | User input |
| Time between bursts | Determines time between each pulse burst This time interval is developed by a Visual Basic Timer control, which has a time resolution of approximately 20 milliseconds. Limitations are based on time needed to display bursts. As a result the mimimum time should be 200 msec with a maximum of 32 sec | User input 200 msec–30 sec |
| ER pulse delay | Determines number of pulses prior to initiating energy reduction pulses ER pulses are pulses with a shorter time constant than the normal pulses and thus discharge the capacitors quickly. Note: ER also occurs after last pulse See Safety Section 817 | User input 0–10,000 (even numbers) |
| ER pulse number | Determines number of pulses in each burst that will be delivered at the reduced time constant See Safety Section 817 | User input 0–1000 (even numbers) |
| PULSE ON | Enables the high voltage power supply and controls the high voltage pulses ON or OFF Also initiates the timer and data saving algorithms. | User clicks ON |
| PULSE OFF | Stops the generation of the high voltage pulses and sets the high voltage supply to 0 However, depending on the capacitance of the capacitor bank, additional time must be allowed for the high voltage to discharge to a safe value Energy reduction mode is activated when OFF has been depressed to more rapidly discharge the capacitors See Safety Section 817 | User clicks OFF |
| Pulse width/time between pulses multiplier | Multiplies the pulse width and time between pulses value by a factor of 10 if required This increases the range of these two parameters An external clock at 2 MHz is utilized instead of the 20 MHz internal clock. | User input toggle button 1 or 10X |
| Set temp cooler | Establishes the Peltier cooler temperature The Visual Basic (VB) program controls this temperature through a digital port in the KPCI-3104 | User input |
| Flow rate | Determines the rate at which fluid should be pumped through the system based on the existing tube diameter | Text combo window with pull down menu. 0.005–1 mL/sec |
| Flow direction | Determines the direction that the peristaltic pump should turn, thus determining the direction of fluid flow through the system | Option buttons CW or CCW |
| PUMP ON/OFF | Determines whether the pump will be ON or OFF. | ON or OFF - two separate buttons |
| PRIME START | Actuates certain solenoid pinch valves that allow priming fluid to flow through the flow cell | User clicks on option button |
| PRIME END | Actuates certain solenoid pinch valves when the priming process is over. | User clicks on option button |
| SAMPLE START | Actuates certain solenoid pinch valves when the blood sample is ready for flow electroporation | User clicks on option button. |
| OFF | Closes all the pinch valves. | User clicks on option button |
| Save data | This button is used to activate the data saving form, which allows for data to be saved to a designated disk file. Time, date, voltage, monophasic/biphasic setting, pulse width, time between pulses, clock frequency, IR exit temp, elapsed time, er pulse delay, er pulse number, and up to ten sets of pulse voltage and pulse current displays One pulse burst is saved every minute for up to a total of ten minutes | User clicks on option button |
| Temperature/voltage calibration | This button allows the user to calibrate the cooler, voltage waveforms, and fluid outlet IR sensor. The form is divided into two sections. The upper section is used for the calibration of the various temperature measurement channels. For each temperature channel, four values are required The two-point calibration method uses an independently measured High and Low temperature value along with a corresponding set of digital outputs from the system A/D converter. The digital values can be read by means of the "Display New Temperature Count" button in the center bottom of the form These count values can be manually inserted into the Temperature count window for the given condition VB text windows in the lower section of the form contain the current set calibration constants for the non-temperature section of the program. These values can be edited directly as needed When the "Exit and Save (Calibration Values and Display Constants)" button is depressed all of the current calibration values are passed on to the VB program and stored in the disk calibration file. This form is password-protected | User click on button |

The system software provides the user complete control of all parameters influencing electroporation. The user may only manipulate the high voltage and the set cooler temperature. All other parameters are fixed to the optimized red blood cell (RBC) parameters. Once the run begins, pulsing parameters will freeze and appear dimmer. The remaining enabled controls are pushbuttons to begin and end the pulsing, pump motion, and release of the pinch valves. If the user enters a value for high voltage beyond the capability of the system, the GUI will ask the user to input a number in a given range. The voltage and current traces on the GUI keep the user informed in real time of the waveform being delivered to the sample. These traces also display a cumulative plot of the peak voltages and currents over the period of the run. At the end of the run, the user can chose to save data to a designated location. Plots of this data can be generated to determine the consistency of the waveform the sample was subjected to over the period of the run.

In addition to input parameters and traces, the GUI also displays real time information on the temperature of the cooler, the temperature of the sample, and the time elapsed. The watchdog is continually displayed as a redundant note to the user that the system is powered. Although the current system lacks an internal diagnostic system, a few simple diagnostics are implemented to increase the awareness of the system. The system can determine if the disposable set is attached properly and will display "Flow Cell Attached" in red text on the GUI when it is attached. Also during pulsing, should the sample reach a temperature that could potentially damage the sample, the system will notify the user via the GUI and discontinue the application of the electric field.

Figure 8:
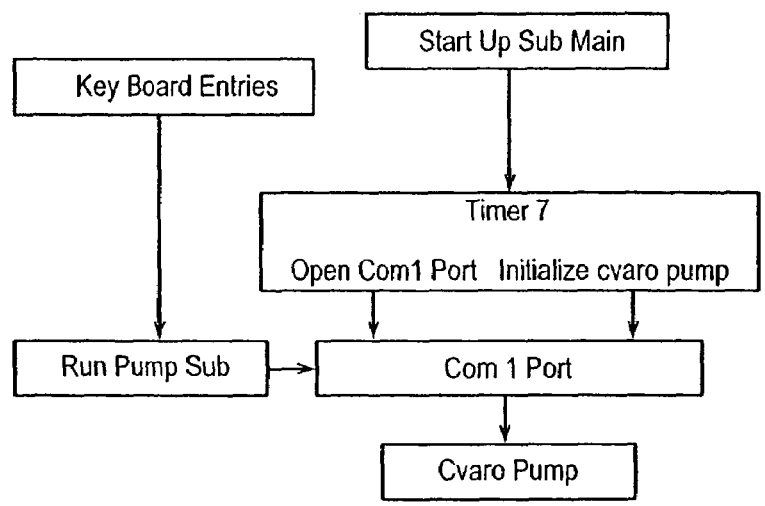
FIG. 8 is a schematic diagram of the CAVRO Pump Initialization and Control.

FIG. 8 is a photograph taken of the GUI during an RBC run. The parameters are dimmed and the traces show the conditions the sample is being subjected to. Table 4 below gives a general overview of the described displays.

Program Overview

A fundamental concept of the FES is that system operations, with the exception of an electronics AC power ON/OFF switch, are all controlled from the GUI using mouse clicks and keyboard entries.

Due to the high voltages often associated with electroporation, the AC power to the electronics is placed under the control of a watchdog system. The watchdog includes a VB module that generates a continuous series of pulses on one bit of a digital output port. An analog circuit that enables the AC power for the electronics portion of the FES detects these pulses. Since these pulses are only generated by the FES VB program, the AC power is only enabled while the program is running. Should the computer crash, or the program be stopped for any reason, the AC power to the electronics is terminated.

TABLE 4

GUI Displays

| ITEM | DESCRIPTION |
|---|---|
| Fluid exit temperature | This display shown on the PC monitor shows an unsigned integer representing the temperature, in degrees Celsius, as measured by an infrared temperature sensor located on the top of the instrument When a disposable is attached, the outlet tubing is inserted in the slot on the sensor so that the passing fluid temperature can be monitored Degrees are displayed to 01 degrees Celsius Accuracy is approximately +/− 2° C. If the fluid exit temp is between 35–40° C. the user will be warned through the GUI by displaying a "Temp is above limit" message If the temperature exceeds 40° C. the same message will be displayed and the high voltage pulsing will stop If the temperature is between 5° C.–10° C. the user will be warned through the GUI by displaying a "Temp is below limit" message If the temperature falls below 5° C. the same message will be displayed and the high voltage pulsing will stop |
| Timer display | THIS DISPLAY SHOWS THE TIME THAT HAS ELAPSED SINCE THE LAST TIME THE PULSE ON BUTTON WAS DEPRESSED THE TIME IS FORMATTED TO GIVE READINGS EVERY 01 SECONDS The timer display freezes at the current value if the system high voltage pulsing is OFF, or the ON/OFF rocker switch on the system is switched to the OFF position |
| Flow cell attached display | This indicator on the GUI labeled "Flow cell attached" signals the user that the flow cell micro-switch has been activated and power is available to the high voltage supply whenever the ON button in the pulse parameter section of the GUI is pressed When the flow cell is attached the text will turn red When the flow cell is not properly attached the display will turn a green color and read "FLOW CELL NOT ATTACHED" |
| Cooler measured temperature display | This indicator on the GUI displays the actual temperature as measured by the platinum sensor applied to the cooling plate This display is next to the cooler set point The actual temperature is automatically adjusted via the system controls and Peliter cooler until it equals the set temperature |
| Watchdog | This indicator on the GUI displays an alternating alphanumeric display The display toggles between "0" and "x" The software employs a "WATCHDOG" that generates a square wave signal With the exception of the external digital logic elements, power is only supplied to the circuitry external to the computer when the square wave signal is detected Should the visual basic program crash due to power failure or other reason, the required square wave will not be generated and power to the external circuits including the high voltage supply will be disabled The watchdog enables the system to properly initialize all of the KPCI-3104 systems prior to the system being powered |
| Pulsing notification | The word "PULSING" will appear in red lettering on the GUI when high voltage pulses are being delivered |

Flow Electroporation System Software Description

The software program employed in the new FES is written in Microsoft Visual Basic (VB), Version 6. The required computer operating system is Microsoft Windows NT, with Service Pack4 (at a minimum). With the exception of the CAVRO pump, the computer is interfaced to the hardware electronics by means of a Keithley instrument -3104 Data Acquisition and Control card that plugs into a PCI slot in the computer. This interface board allows for analog and digital input and output, as well as counter timers used for computer-controlled pulse generation. Keithley also supplies a VB software driver (DriverLINX). The version of this driver was selected specifically for Windows NT. The computer should operate at least 200 MHz with at least 64 Megabytes of RAM and must have at least one PCI slot.

The CAVRO pump is controlled through a COM port on the computer using a VB command syntax provided by the manufacturer.

The VB program is divided into the following five major parts (described in greater detail below): 1) Sub Main Start Up Calls (Module 1); 2) Temperature Measurement and Control; 3) CAVRO Pump Initialization and Control; 4) Modular Pulse Generation; and 5) Analog and Collect Plot Data.

Sub Main Start-up Calls

This section of the program begins the process by presetting and computing variables, initializing the KPCI-3104 card and its subsystems, starting the watchdog, and initializing the CAVRO pump.

Figure 6:
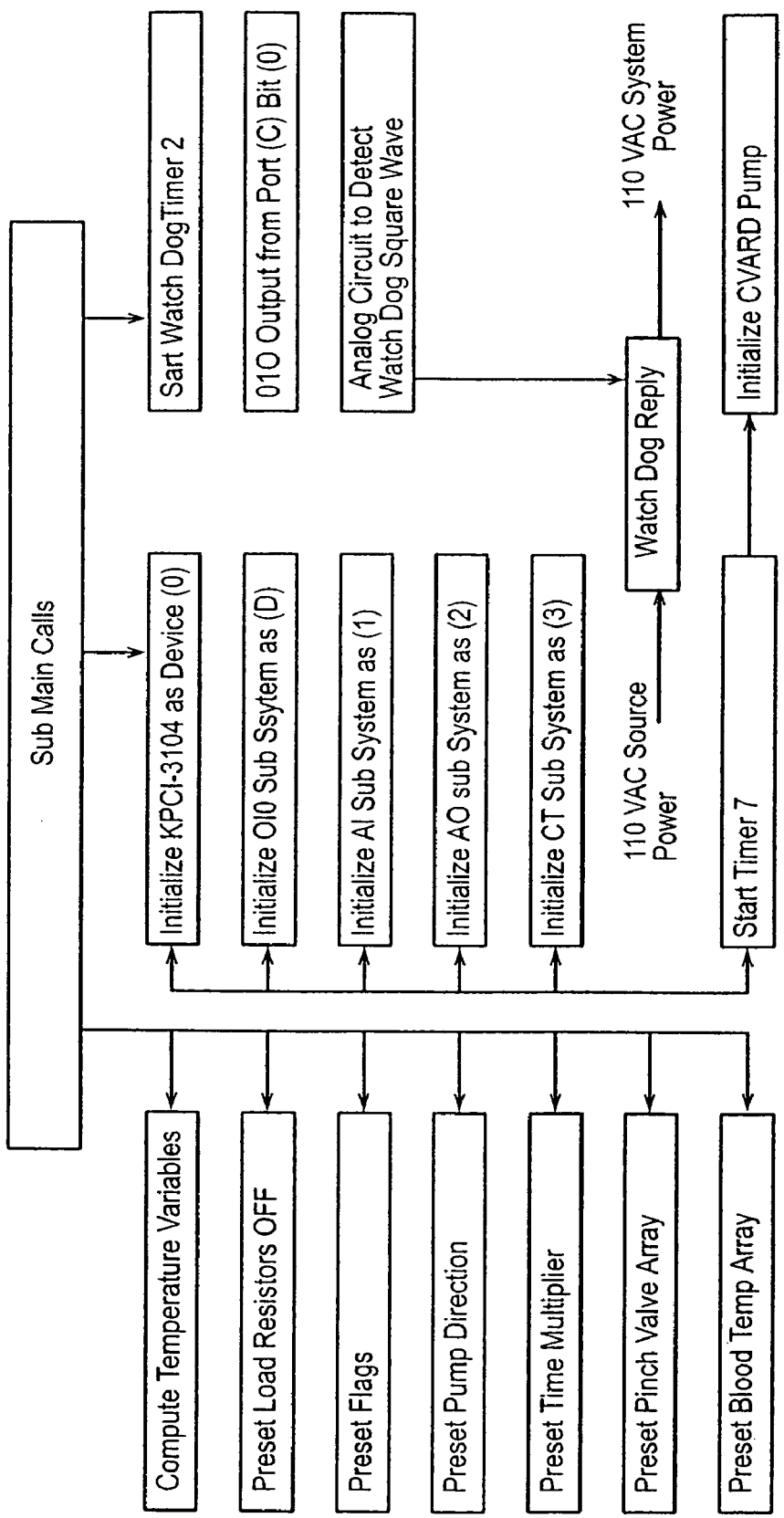
FIG. 6 is a schematic diagram of the Sub Main Start-up Calls (Module 1).

As can be seen in FIG. 6, the sub main calls up a series of sub routines at the beginning of the program as soon as the program is started. The first action is to compute a set of temperature variables. To compute the temperature variables it is necessary to download the appropriate calibration constants from a disk file. The electronics for the system is designed with only one analog control; consequently, the analog voltages need to be scaled for accuracy by means of constants stored on the hard disk of each system. By storing the constants in this manner, it is possible to upgrade the software in many systems with only one version of the code. It is also necessary to preset many of the variables and conditions prior to the start of the main program.

Following this process, a generalized initialization of the KPCI-3104 card is performed, followed by a more specific initialization of each of the KPCI-3104 subsystems. The shorter subsystem initializations are required any time the Keithley subsystem is used for a different task. The KPCI-3104 card has four different subsystems. Each subsystem is set up as a separate control in VB so that they can be reinitialized separately when their functions are changed. This is particularly important for the Analog Input (AI) subsystem as it is used for collecting pulse trace data at high speed using one set of channels and then reconfigured to collect low speed data for temperature measurements with another set of channels.

Two VB Timers are used in the "Start Up" portion of the program. The first timer, Timer 2 is used to generate the pulses needed for the watchdog signal. This timer runs continuously and with every clock cycle, the digital output (bit(0) of Port(C)), is cycled between a "one" and a "zero". An analog circuit located in the "Electronics" portion of the system then detects this square wave signal. Upon detection, a TTL level signal is sent to a solid-state relay that controls the 110 V AC power to the "Electronics" portion of the system. A second VB Timer is used to delay the initialization of the CAVRO pump until after the watchdog has completed its task.

Temperature Measurement and Control

This section of the software runs the IR and RTD (temperature control module) temperature measurements. Additionally, the RTD data is used to control the temperature of the thermal cooling system. This part of the program runs continuously; however, the control temperature may be changed through the GUI.

Figure 7:
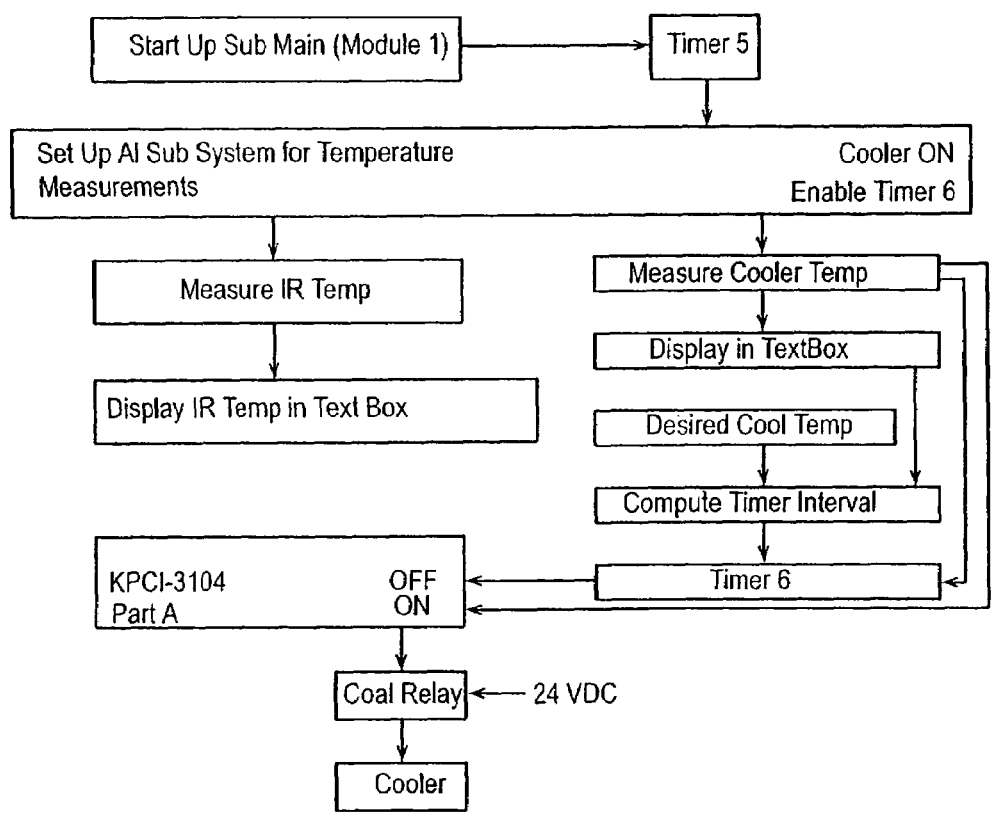
FIG. 7 is a schematic diagram of the Temperature Measurement and Control.

The Temperature Measurement and Control system is depicted in FIG. 7. After the various systems are initialized, VB Timer 5 is enabled. This timer is configured to continuously cycle every five seconds. At the end of each five-second period, it causes the IR temperature to be measured, the cooler temperature to be measured, it starts Timer 6 and then turns on the cooler system. The fraction of the next five-second cycle that the cooler remains on depends upon the difference between the "Desired Cold Temp" and the "Measured Cooler Temp". This system operates continuously while the main program is running.

CAVRO Pump Initialization and Control

This section enables the operator to control the CAVRO pump from the keyboard without involving the KPCI-3104 card. A significant aspect of this section is that the CAVRO pump can only be initialized after the watchdog has had sufficient time to provide power to the pump.

As shown in FIG. 6, the "Start Up Sub Main" module also starts VB Timer 7, which is used to delay the initialization of the CAVRO pump and the COM1 port on the computer. The delay time is sufficient for the watchdog to permit power to the "Electronics". This same power is supplied to the CAVRO pump. The pump requires power to be initialized. The pump is controlled from the keyboard using the COM1 Port.

Modulator Pulse Generation

This section of the program controls the timing of the pulses that are sent to the high voltage modulator switches. The switches allow the designated high voltage to be coupled to the electroporation flow cell.

Figure 9:
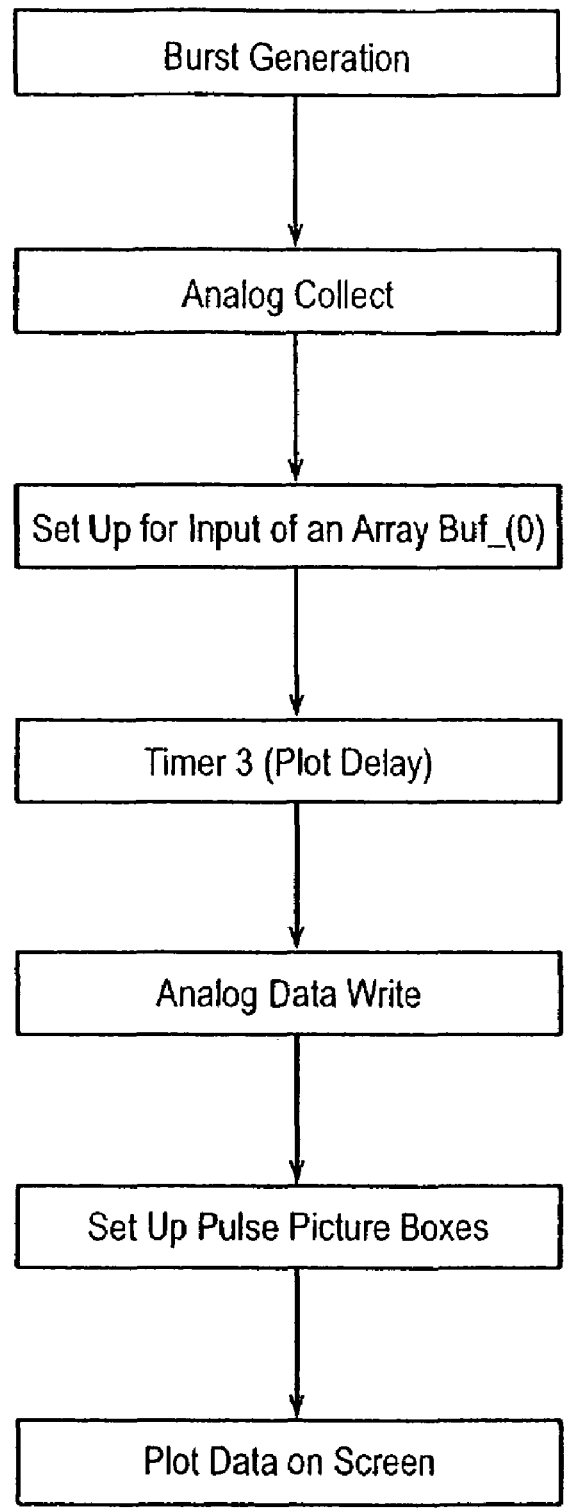
FIG. 9 is a schematic diagram of the Analog Collect and Plot Data.

FIG. 9 consists of a flow chart for the generation of the pulse timing and selection of pulses for the system. The Keithley-3104 card contains four independent Counter Timers (CT). These timers are capable of generating TTL level "Clock" pulses of the proper width and spacing as requested from the keyboard. These pulses are generated continuously until the counter subsystem is reinitialized. CT (3) pulses are used to gate the pulses from CT (0) and CT (1) in "Digital Logic". The timing of the CT (3) gating pulse is determined in software by the number of modulator pulses desired. The fourth and last CT Timer is used to control the timing of an "Energy Reduction" pulse. A second set modulator switches are used to impose a restive load to rapidly reduce the high voltage during a series of electroporation pulses. These switches are also used to discharge the capacitor bank when the high voltage is not needed.

Analog Collect and Plot Data

This section of the program addresses the synchronized collection of high voltage/current data of the pulses applied to the electroporation flow cell. The data is collected by the A/D converter located on the KPCI-3104 card synchronized with the pulse generation of the CT without interfering with their operation.

Figure 10:
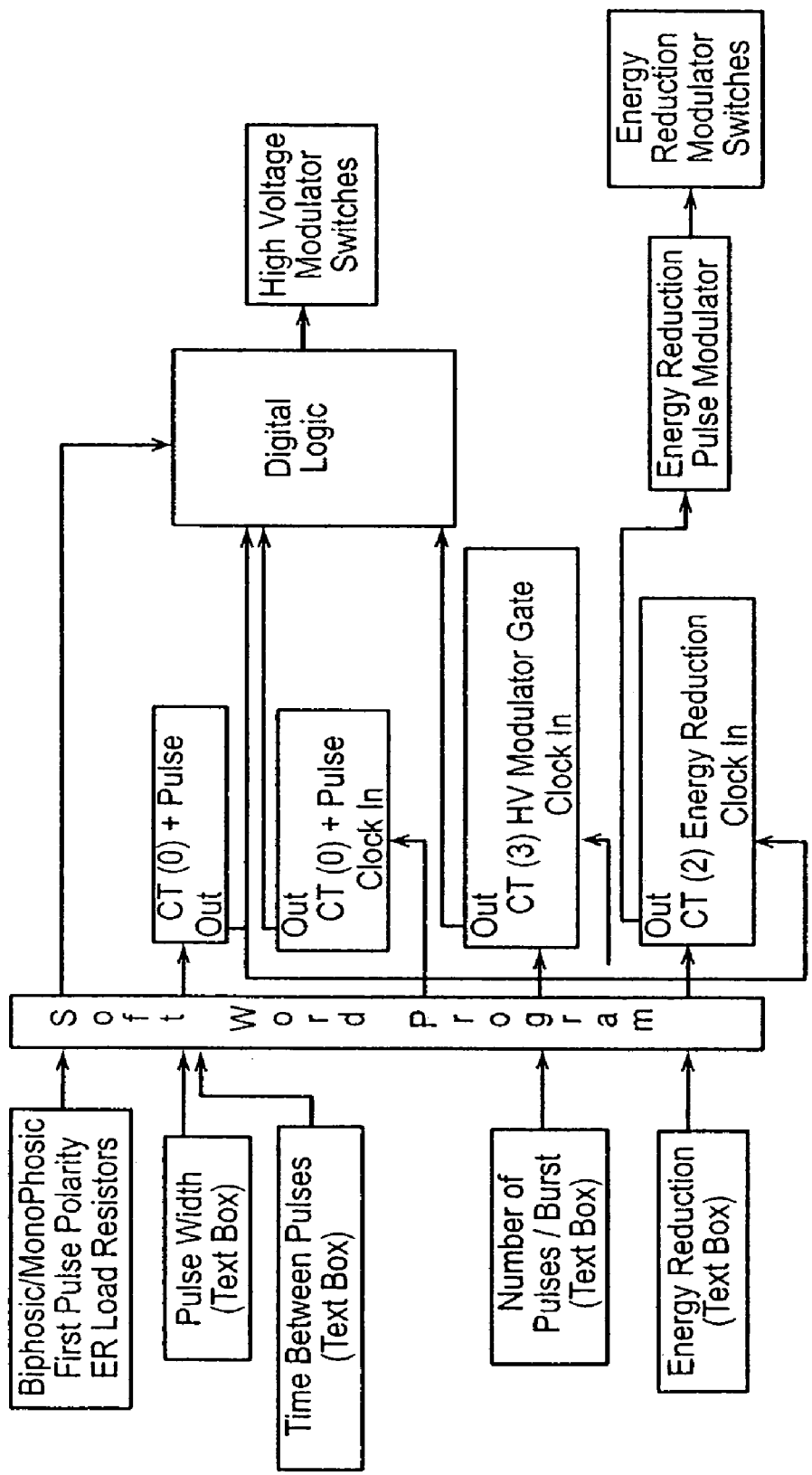
FIG. 10 is a schematic diagram of the Modulator Pulse Generation.

In FIG. 10, "bursts" of "modulator pulses" are used to trigger the "analog collect" sub routine. It is important to note that although initiation of the analog data collection of voltage and current pulses in the "Electroporation Flow Cell" are triggered by the modulator pulses, the two subsystems operate independently of each other. The same AI subsystem is employed for both the temperature and modulator pulse measurements. The sub routines controlling each AI function set flags, which prevent interference between the two systems. Prior to the generation of the "burst" of modulator pulses, the AI subsystem is initialized for high-speed data collection. Coincident with the first pulse in the "burst," the AI subsystem is triggered and data is collected into an array that was established in the AI initialization process. Timer 3 causes a time delay to insure all data is collected into the buffer prior to the plotting of the data on the GUI screen. One set of "Plot Data" is saved in an array every minute for up to twenty minutes. This data may be saved to hard disk if desired at the end of the electroporation procedure.

Disposable Set

The disposable set is composed of PVC bags, PVC tubing, connectors, silicone pump tubing, and a flow cell (see Table 5 below). All plastic components contacting blood are Medical Grade Class VI materials.

TABLE 5

Components of Disposable Set

| DESCRIPTION | MATERIAL | CONTACTS BLOOD PATH | CLASSIFICATION | VENDOR |
|---|---|---|---|---|
| Electrode gasket | Platinum cured silicone | Yes | USP XXII Class VI | Amermold |
| Electrodes | Iron (Low Carbon Flat Stock - AISI Type C 1018) | No | | NPI |
| Polycarbonate plate | Polycarbonate | Yes | USP XXI Class VI | Medsource Technologies |
| Polycarbonate retainer | Polycarbonate | No | USP XXI Class VI | Medsource Technologies |

TABLE 5-continued

Components of Disposable Set

| DESCRIP-TION | MATERIAL | CONTACTS BLOOD PATH | CLASSI-FI-CATION | VENDOR |
|---|---|---|---|---|
| Electroplating on electrode surface | 100 microinches pure gold | Yes | | AVM Plating |
| 14 7" PVC tubing | PVC | Yes | | Baxter |
| 7 7" PVC tubing | PVC | Yes | | Baxter |
| Polycarbonate Y tubing connector | Polycarbonate | Yes | USP Class VI | Value Plastics |
| Polycarbonate pump tubing connector | Polycarbonate | Yes | USP Class VI | Value Plastics |
| 4 7" medical grade silicone pump tubing - 0 104" ID × 0 192" OD | Silicone | Yes | USP Class VI | New Age Tech |
| 1 7" PVC tubing | PVC | Yes | | Baxter |
| 15" PVC w/150 mL transfer Bag | PVC | Yes | | Baxter |
| 16 5" PVC W/150 mL transfer Bag | PVC | Yes | | Baxter |

Figure 11:
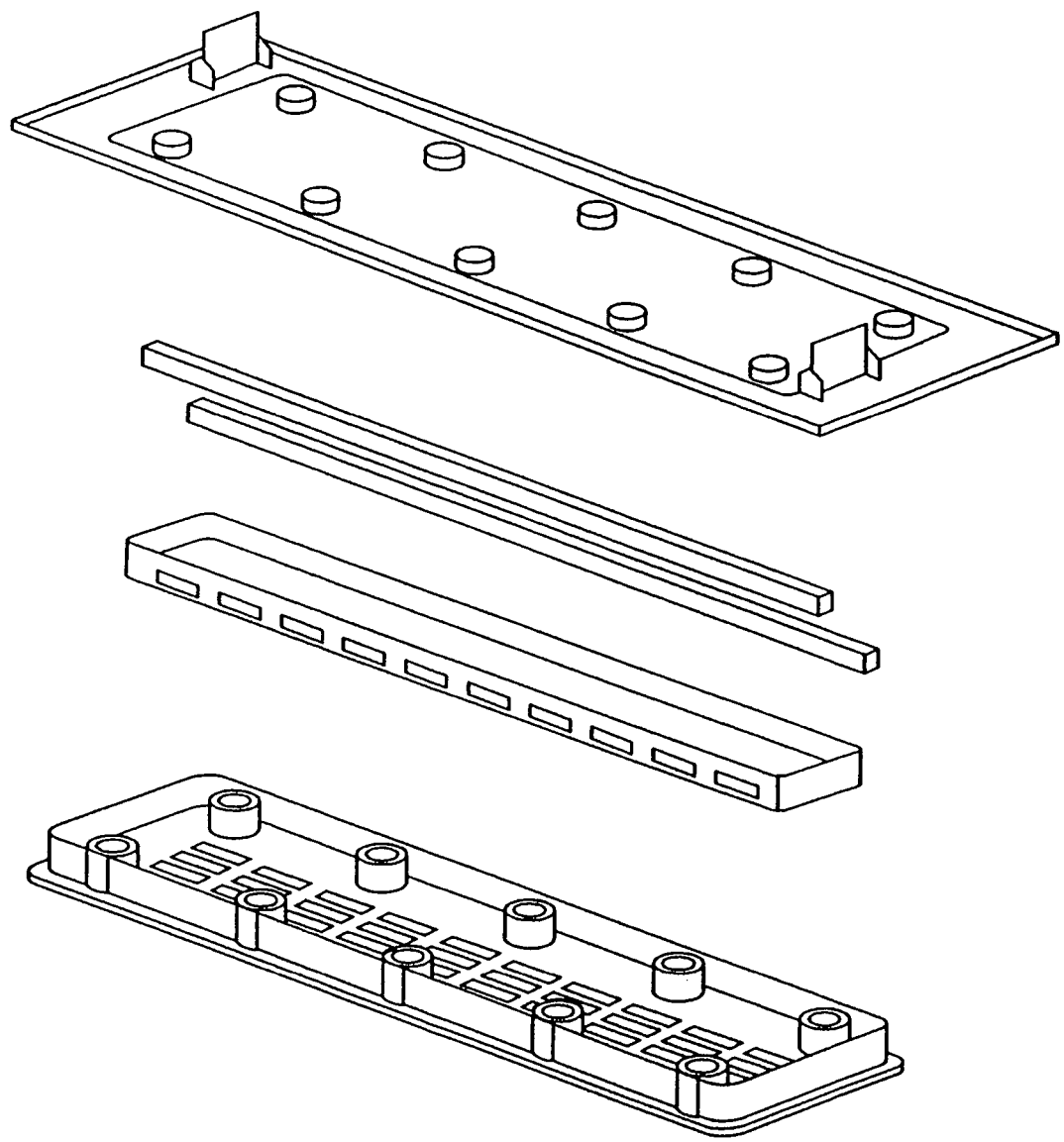
FIG. 11 is an exploded view of one embodiment of the flow cell.

FIG. 11 illustrates an "exploded" view of the flow cell. The flow cell (also shown in FIG. 15) consists of two low carbon steel (99+% Iron) electrodes electroplated with approximately 100 μinches of Pure Gold (99.9%). Part of the quality control process specifies that the electrodes are straight to within 77 μm over their entire length. When the electrodes are placed in parallel, there is a maximum deviation in distance between bar electrodes of 154 μm. During the Disposable Set assembly process, the electrodes are inserted into the electrode gasket, which is then sandwiched between the retainer and plate. The nominal gap between the parallel bar electrodes is 2 mm. When the disposable set is in use, approximately 750 Volts is applied across the electrodes, resulting in an applied electric field of approximately 3.7 kV/cm. Control of electrode position and straightness dictates that the field strength may vary by only 7.5% or 0.27 kV/cm. The flow cell holds a volume of approximately 1.6 mL.

There are four bags attached to the disposable set (150 ml Baxter Transfer Sets). The first bag is called the Prime Bag. This bag contains saline that is pumped from the bag, around the pump, through the flow cell, and into the waste bag. The purpose of the prime bag is to remove air and any particulates that may be in the tubing or flow cell. The second bag, called the Sample Bag, contains the cell suspension plus the IHP that will be inserted into the cell via the electroporation process. Each of these bags is connected to PVC tubing lines that pass through designated pinch valves.

The outlet port of the flow cell also has two bags attached, one of which is called the waste bag. This bag holds the priming fluid and a small volume of the sample after they have passed through the flow cell. The last bag is called the product bag, which holds the red blood cells that have been subject to the flow electroporation process with the IHP molecule. Again, there are pinch valves designated for each of these valves to prevent mixing of bag contents.

Alternative Flow Electroporation Cell Assembly

The alternative flow electroporation cell assembly is another embodiment of a flow cell that can be used in the present invention. This embodiment is easy to manufacture and is relatively inexpensive.

Figure 13:
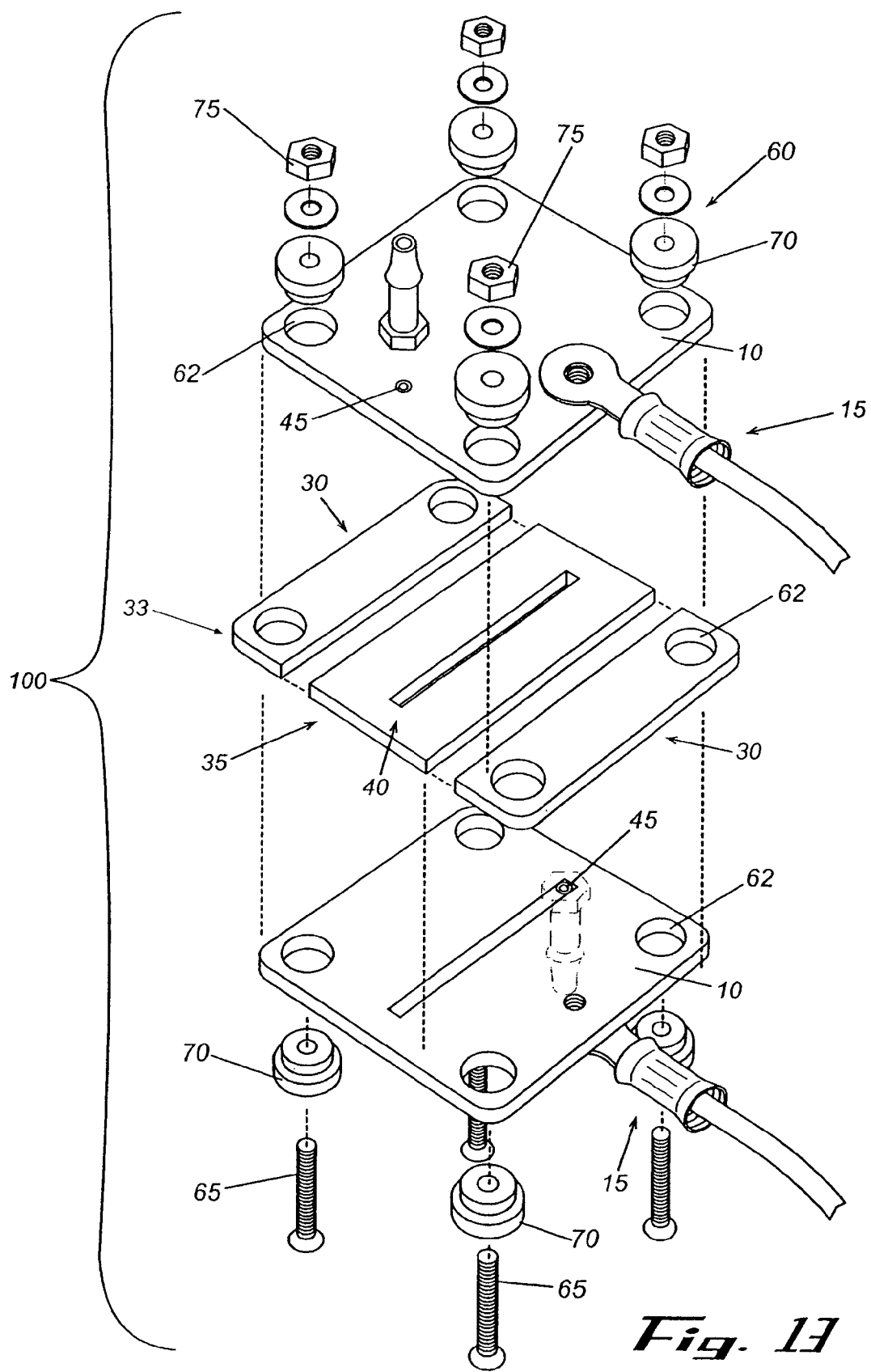
FIG. 13 is an exploded perspective view of a second disclosed embodiment of a flow electroporation cell assembly of the present invention.

Referring now to the figures wherein like reference numerals represent the same or equivalent features throughout the figures, the present invention includes a flow electroporation cell assembly as shown, for instance, in FIG. 13. According to the present invention, selectively fractionated biological units such as blood cells or platelets are introduced from an exterior source into a flow electroporation cell assembly, where the biological units are subjected to electroporation in the presence of a biological or chemical vector, causing the vector to enter transiently opened pores in the encapsulating membranes of the biological units. Once the desired electroporation effect is achieved, the biological units are moved exterior to the flow electroporation cell assembly to permit further handling of the treated units and electroporation of incoming, untreated units. A detailed description of the structure and construction of the flow electroporation cell assembly according to one embodiment of the present invention is provided below.

The present invention is a flow electroporation apparatus for electrical treatment of suspensions of particles, especially including living cells, comprising a flow electroporation cell assembly having one or more inlet flow portals, one or more outlet flow portals, and one or more flow channels, the flow channels being comprised of two or more walls, with the flow channels further being configured to receive and transiently contain a continuous flow of particles in suspension from the inlet flow portals; and paired electrodes disposed in relation to the flow channels such that each electrode forms at least one wall of the flow channels, the electrodes further comprising placing the electrodes in electrical communication with a source of electrical energy, whereby suspensions of particles flowing through the channels may be subjected to an electrical field formed between the electrodes.

As shown in FIG. 13, a flow electroporation cell assembly 100 may be constructed of two opposing electrode plates 10. Typically, the electrode plates 10 may be constructed of iron, steel, copper, aluminum, or other electrically conductive metals or metal alloys. The electrode plates 10 may further be coated with gold, platinum, zinc, carbon, or other plating materials to enhance their electrical conductivity. Each electrode plate 10 may be provided with one or more electrical terminals 15 that interface with the power supply circuitry of the overall flow electroporation system. In alternate embodiments, one or both of the opposing electrode plates 10 may further be provided with an interface having a cooling element 20. The cooling element 20 may be a thermoelectric cooling element, or may provide cooling by direct water or other coolant contact, by ventilation through a heat sink, or other cooling means to dissipate heat generated in the electroporation process, which is typically an exothermic process.

Referring still to FIG. 13, the electrode plates 10 may typically be separated by one or more electrode gap spacers 30. The thickness of the electrode gap spacers 30 will define and fix a gap 33 between the electrodes 10. The gap 33 between the electrodes 10 can easily be adjusted to any desired measurement simply by changing the gap spacers 30. The thickness of one such gap 33 will vary depending on the flow volume and field strength, but will generally be greater than 3 mm, preferably approximately 0.01 mm to approximately 2 cm, especially preferably approximately 0.1 mm to 1 cm. It is also preferred that the gap 33 be greater than 3 mm, preferably about 4 mm to about 2 cm, especially about 5 mm to about 1 cm. It is also desirable that the ratio of the combined surface area of the two electrode plates 10 in contact with buffer contained in the cell assembly 100 to the distance between the two electrode plates is approximately 1 to 40 cm; preferably approximately 1 to 50 cm, more preferably approximately 1 to 60 cm more preferably approximately 1 to 70 cm, more preferably approximately 1 to 80 cm, more preferably approximately 1 to 90cm, more preferably approximately 1 to 100 cm. For example, if each of the two electrode plates 10 have a surface area of approximately 5 $cm^2$ then the distance between the electrode plates should be approximately 0.2 cm and therefore the ratio of the combined surface area to the distance between electrodes should be 5 $cm^2*2/0.2$ cm=50 cm.

The electrode gap spacers 30 are typically constructed of an electrically insulating material, and may be fashioned from such materials as plastic, ceramic, rubber, or other non-conductive polymeric materials or other materials.

Figure 14:
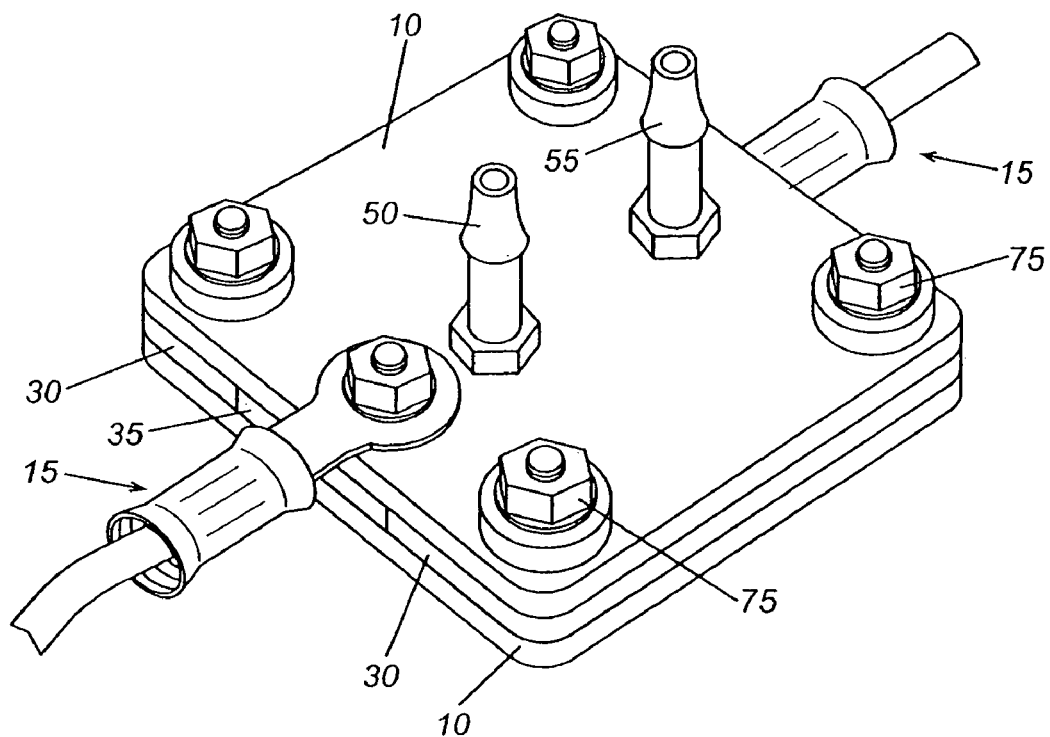
FIG. 14 is a perspective view of another disclosed embodiment of a flow electroporation cell assembly of the present invention.

Also in another embodiment of the present invention as shown in FIG. 14, a gasket 35 containing a flow channel 40 may be positioned between the electrode plates 10, with the thickness of the gasket 35 equal to the thickness of the electrode gap spacers 30. The gasket 35 typically forms a seal with the opposing electrode plates 10. The gasket 35 may be constructed of silicone, other synthetic or natural rubbers or other polymers, or other electrically non-conductive materials. Integral within the gasket 35, one or more flow channels 40 is provided. The flow channel 40 is defined by a channel or other cutout within the gasket 35. The size and shape of the flow channel 40 is proportional to the size and shape of the electrode plates 10.

In one embodiment of the flow electroporation cell assembly according to the present invention as shown in FIG. 14, the electrode plates 10 may contain one or more portal bores 45. Each portal bore 45 may further contain either a flow inlet portal 50 or a flow outlet portal 55, which serve to connect to and interface with the respective inflow/outflow transport pathways of the overall flow electroporation system.

In one embodiment of the flow electroporation cell assembly according to the present invention, the electrode plates 10 and electrode gap spacers 30 may also contain one or more attachment means to allow their secure assembly. In various embodiments of the present invention, the attachment means 60 may include fasteners such as screws, rivets, rods, or clips which may be employed to secure the desired positions of the electrode plates 10 with the gasket 35 and flow channel 40 interposed therewithin. In still other alternate embodiments of the electroporation flow cell assembly 100 according to the present invention, the attachment means 60 may be secured by adhesives, other bonding techniques, or encapsulation.

Figure 15:
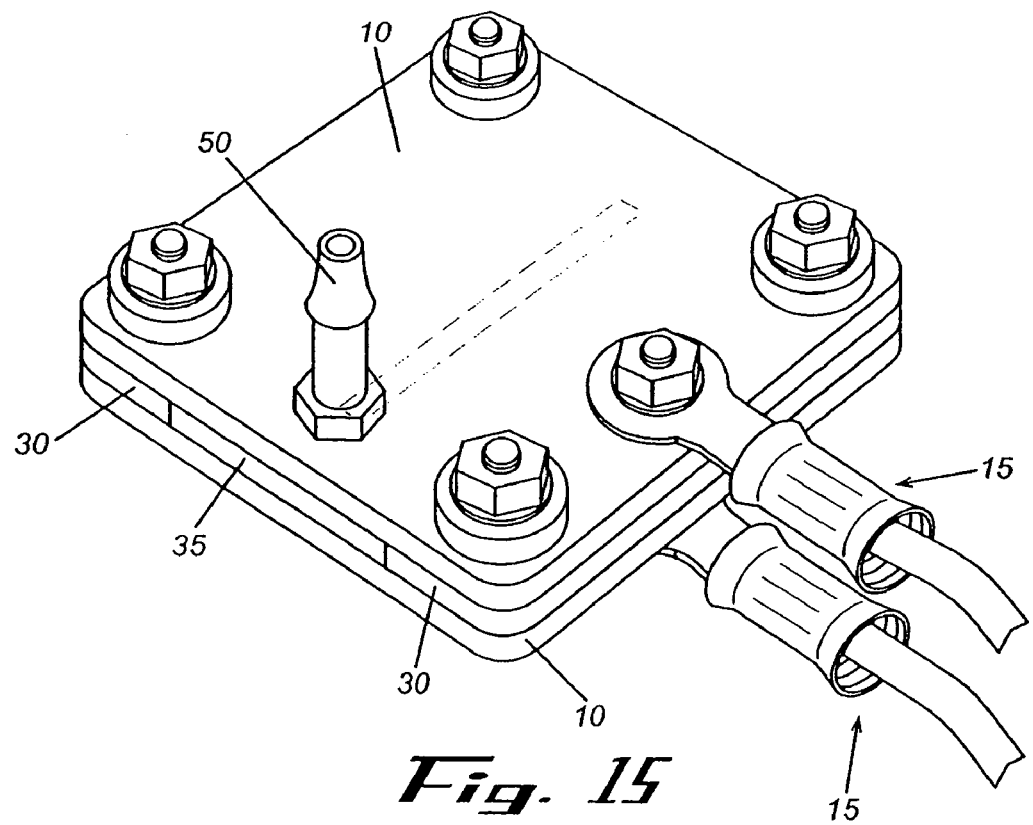
FIG. 15 is a perspective view of yet another disclosed embodiment of the flow electroporation cell assembly of the present invention.

In yet another embodiment as shown in FIG. 15, the attachment means 60 may be an attachment bore, sized and positioned to receive bolts 65. Such bolts 65 may be directly placed through the attachment bores 60, or may be received within plate bushings 70, and the bolts may be secured by nuts 75 that serve to secure the flow electroporation cell assembly 100. In embodiments that employ conductive electrode gap spacers 30, electrical insulation of the opposing plate electrodes 10 may be achieved by the use of insulating plate bushings 70.

Figure 16:
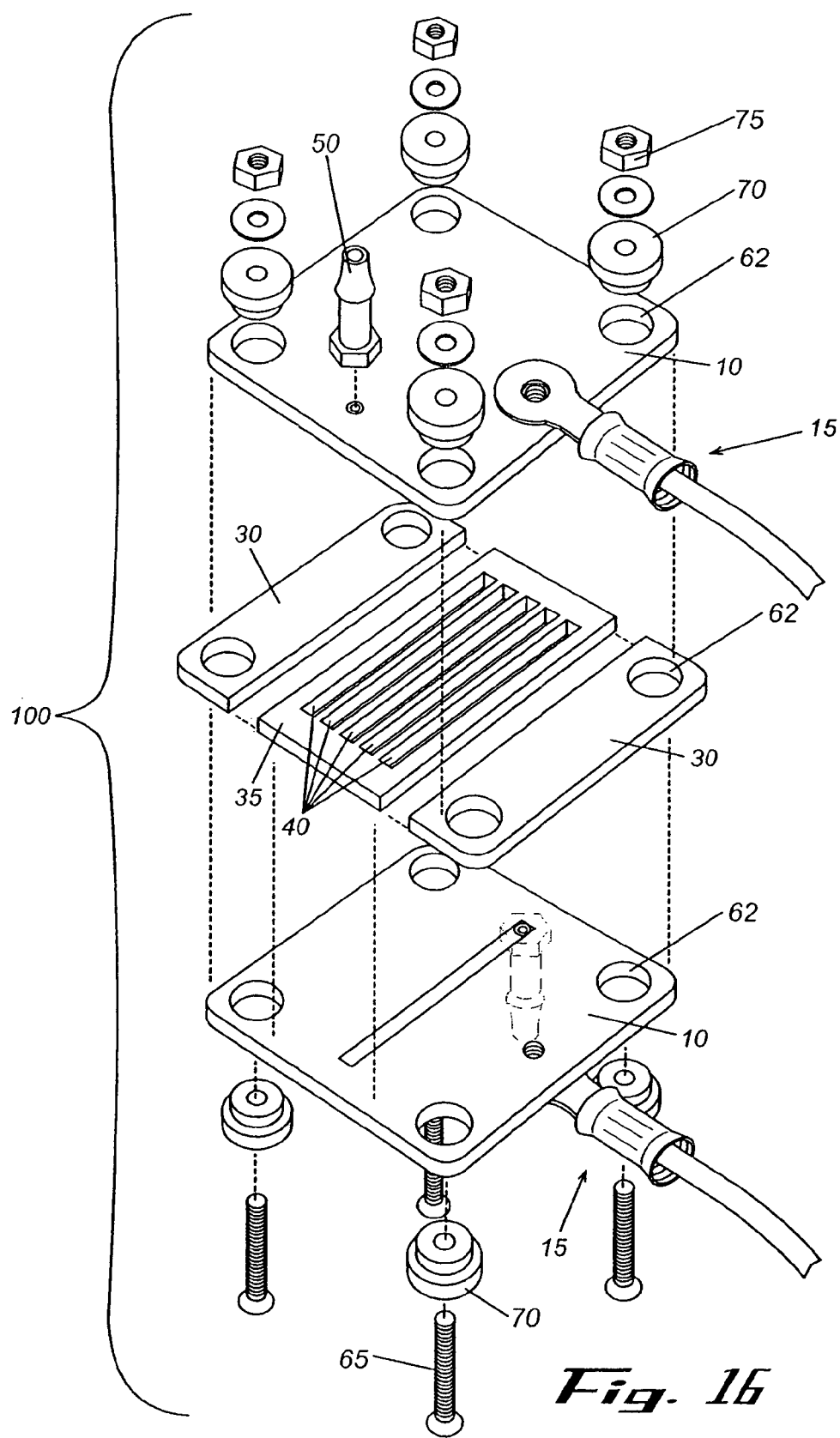
FIG. 16 is an exploded perspective view of another disclosed embodiment of a flow electroporation cell assembly of the present invention with multiple channels.

In various embodiments of the flow electroporation cell assembly according to the present invention, each flow electroporation cell assembly 100 may contain a single flow channel 40 or a plurality of flow channels 40 oriented between the opposing electrode plates 10, as shown in FIG. 16. When desirable, multiple flow channels 40 may be provided to achieve more rapid, higher volume electroporation treatment. The term electroporation region as used herein means that portion of the flow channel 40 in which material flowing therethrough is exposed to an electric field of sufficient strength to affect electroporation. In accordance with the present invention, it is desirable that the two opposed electrode plates 10 that define at least a portion of the opposed walls of the electroporation region of the flow channel form a substantial portion of those opposed walls in the electroporation region. As used herein the term substantial portion shall mean greater than approximately 50%; preferably greater than approximately 60%, more preferably greater than approximately 70%, more preferably greater than approximately 80%, more preferably greater than approximately 90%, most preferably approximately 100%.

Figure 17F:
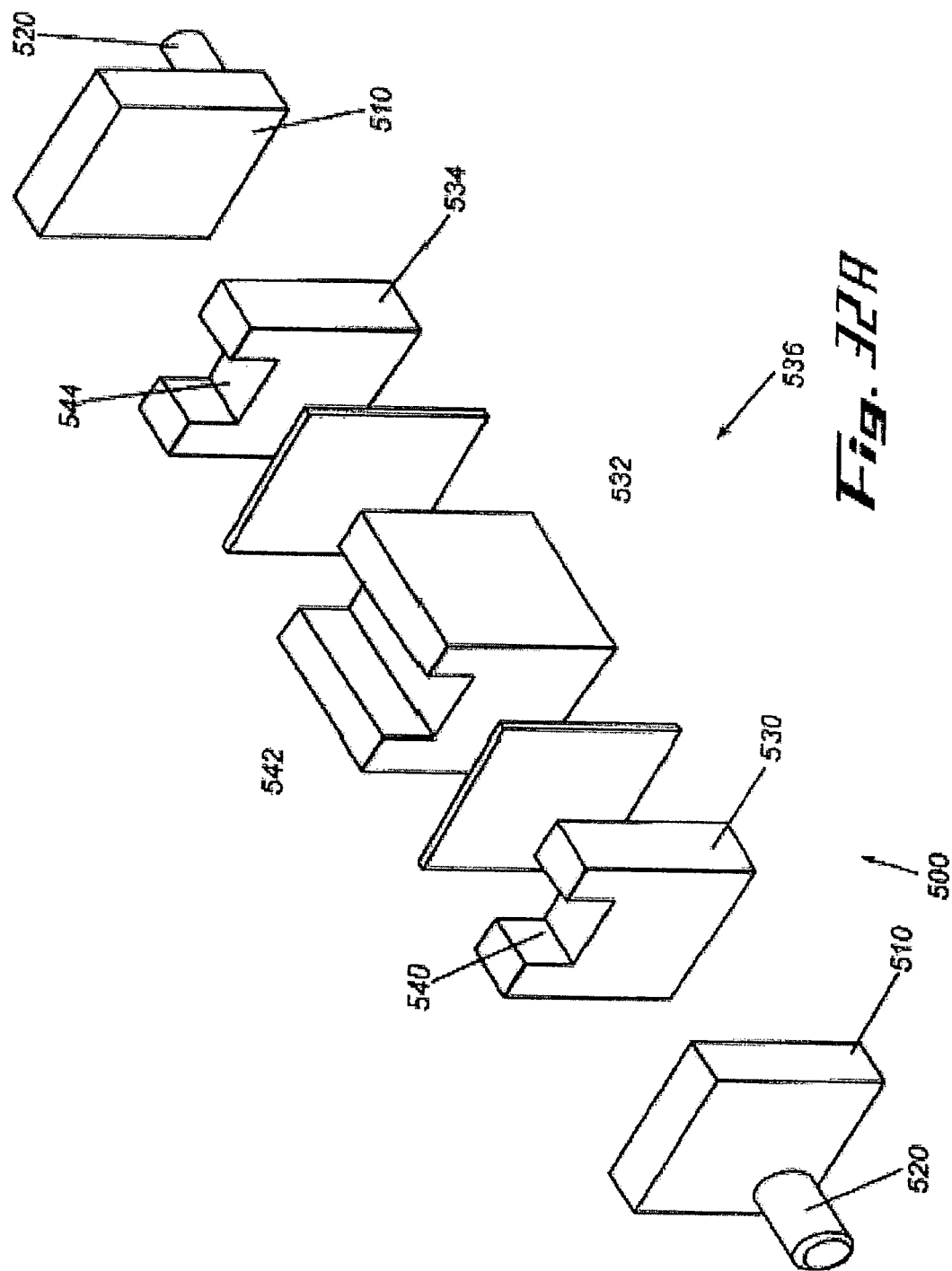
FIG. 17 is a perspective view of a disclosed embodiment of a non-planar electrode flow cell array of the present invention.

In an alternate preferred embodiment of the present invention as shown in FIG. 17, a non-planar electrode flow cell array 105 may be used. In an exemplary embodiment, concentric tubular electrodes 110 may be employed. The tubular electrodes typically have concentric insulating spacers 115 utilized to maintain the desired gap space 33. In such an embodiment, the space between the electrodes could also serve as a flow channel 120, with one or more inlet flow portals 125 and outlet flow portals 130 provided either through the outermost tubular electrode wall 135, or through one or both ends of the tubular electrodes 110. In various embodiments according to the present invention, such a tubular electrode flow cell array 105 could be used singularly, or with a plurality of similar tubular electrode flow cell arrays 105 operating in either parallel or serial function.

Preferably, the flow electroporation cell assembly 100 may be provided as a sterile unit for disposable, single-use applications. The components of the flow electroporation cell assembly 100 may thus preferably be constructed of materials capable of withstanding sterilization procedures, such as autoclaving, irradiation, or chemical sterilization.

Figure 27:
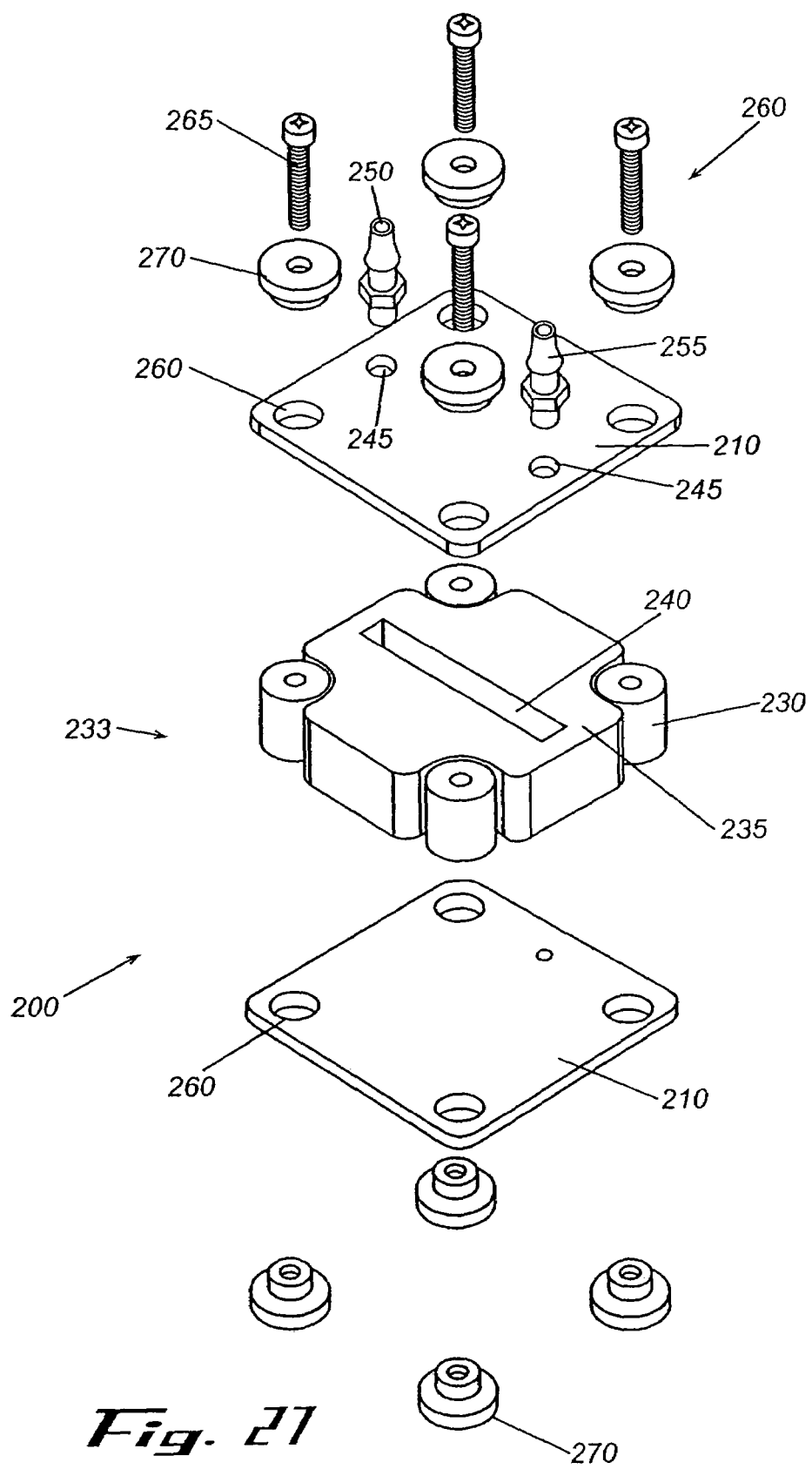
FIG. 27 is an exploded perspective view of a third disclosed embodiment of the flow electroporation cell assembly of the present invention.
Figure 28:
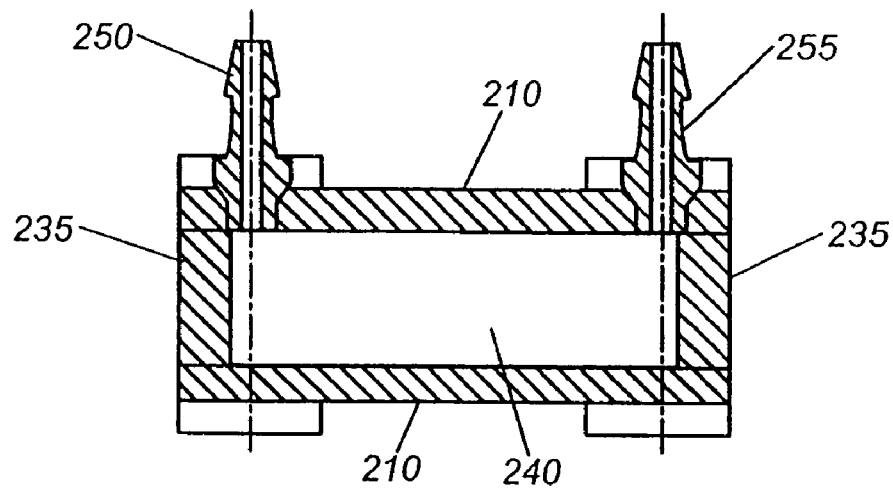
FIG. 28 is a cross-sectional side view taken along the line A—A of the cell assembly shown in FIG. 29.
Figure 29:
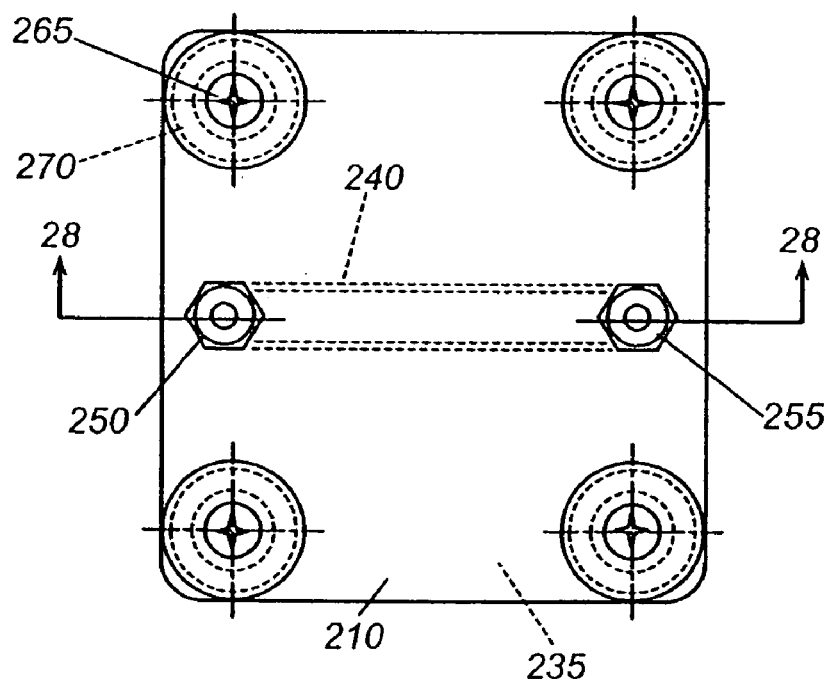
FIG. 29 is a top plan view of the cell assembly shown in FIG. 27.

With reference to FIGS. 27–29, there is also disclosed an alternate embodiment for the electroporation cell of the present invention. As shown in FIG. 27, a flow electroporation cell assembly 200 may be constructed of two opposing electrode plates 210. Typically, the electrode plates 210 may be constructed of iron, steel, copper, aluminum, or other electrically conductive metals or metal alloys. The electrode plates 210 may further be coated with gold, platinum, zinc, carbon, or other plating materials to enhance their electrical conductivity. Each electrode plate 210 may be provided with one or more electrical terminals (not shown) that interface with the power supply circuitry of the overall flow electroporation system. In alternate embodiments, one or both of the opposing electrode plates 210 may further be provided with an interface having a cooling element (not shown). The cooling element may be a thermoelectric cooling element, or may provide cooling by direct water or other coolant contact, by ventilation through a heat sink, or other cooling means to dissipate heat generated in the electroporation process, which is typically an exothermic process.

Referring still to FIG. 27, the electrode plates 210 may typically be separated by one or more electrode gap spacers 230. The thickness of the electrode gap spacers 230 will define and fix a gap 233 between the electrodes 210. The gap 233 between the electrodes 210 can easily be adjusted to any desired measurement simply by changing the electrode gap spacer 230. The thickness of one such gap 233 will vary depending on the flow volume and field strength, but will typically be from approximately 4.0 mm to approximately 2 cm, preferably 5.0 mm to 1.5 cm, most preferable approximately 1 cm. The electrode gap spacers 230 are typically constructed of an electrically insulating material, and may be fashioned from such materials as plastic, ceramic, rubber, or other non-conductive polymeric materials or other materials.

As shown in FIG. 27, a gasket 235 containing a flow channel 240 may be positioned between the electrode plates 210, with the thickness of the gasket 235 equal to the thickness of the electrode gap spacers 230. The gasket 235 typically forms a seal with the opposing electrode plates 210. The gasket 235 may be constructed of silicone, other synthetic or natural rubbers or other polymers, or other electrically non-conductive materials. Integral within the gasket 235, one or more flow channels 240 is provided. The flow channel 240 is defined by a channel or other cutout within the gasket 235 and by the upper and lower electrode plates 210, as shown in FIG. 28.

As shown in FIGS. 27–29, the shape of the flow channel 240 is rectangular in cross-section; i.e., the height (FIG. 28) is approximately equal to the width (FIG. 29). As explained above, the electrode gap spacers 230 establish the distance between the electrode plates 210, which is equal to the height of the flow channel 240. Thus, the height and width of the flow channel 240 are approximately 2.0 mm to approximately 2 cm, preferably approximately 5.0 mm to 1 mm, most preferable approximately 3.0 to 5.0 mm. The length of the flow channel 240 is approximately 5 mm to 5 cm, preferably approximately 1.0 cm to 3.0 cm, most preferable approximately 2.5 cm. The dimensions of the electroporation flow cell shown in FIGS. 27–29 is an electrode length of approximately 0.45 cm, and electrode width of approximately 2.5 cm and an electrode gap of approximately 0.5 cm. This produces a thermal resistance of approximately 37° C./Watt.

The height of the flow channel 240 is also such that the biological material, such as cells, that passes through the flow channel is not thermally degraded thereby. Not being substantially thermally degraded, as used herein, means that cells passing through the flow channel are subjected to a minimal amount of heat energy such that the desired expression vector is inserted into at least 50% of the cells passing through the flow channel, whereby that the cells will produce the desired protein or peptide. For any electroporation device, the passage of electrical current through the cells and the fluid in which they are suspended will generate heat within the cells and the fluid as the cells and fluid act as a resistor. This heating is described by Joule's Law, a well-known Law of Physics. The degree of heating is dependent on the geometry of the electroporation chamber and the materials used in its fabrication. As excessive heating of cells can be damaging, limitation of heating during electroporation is desirable. The degree of heating as a function of the power applied to the electroporation chamber is referred to herein as heat resistance or thermal resistance. In one embodiment of the flow electroporation cell assembly according to the present invention as shown in FIG. 27, the upper electrode plate 210 may contain two or more portal bores 245. Each portal bore 245 may further contain either a flow inlet portal 250 or a flow outlet portal 255, which serve to connect to and interface with the respective inflow/outflow transport pathways of the overall flow electroporation system.

In one embodiment of the flow electroporation cell assembly according to the present invention, the electrode plates 210 and electrode gap spacers 230 may also contain one or more attachment means to allow their secure assembly. In various embodiments of the present invention, the attachment means 260 may include fasteners such as screws, rivets, rods, or clips which may be employed to secure the desired positions of the electrode plates 210 with the electrode gap spacer 230 and flow channel 240 interposed therewithin. In still other alternate embodiments of the electroporation flow cell assembly 200 according to the present invention, the attachment means 260 may be secured by adhesives, other bonding techniques, or encapsulation.

In yet another embodiment as shown in FIG. 27, the attachment means 260 may be an attachment bore, sized and positioned to receive bolts 265. Such bolts 265 may be directly placed through the attachment bores 260, or may be received within plate bushings 270, and the bolts may be secured by nuts (not shown) which serve to secure the flow electroporation cell assembly 200. Electrical insulation of the opposing plate electrodes 210 is desired and may be achieved by the use of insulating plate bushings 270.

In various embodiments of the flow electroporation cell assembly according to the present invention, each flow electroporation cell assembly 200 may contain a single flow channel 240 or a plurality of flow channels (not shown) oriented between the opposing electrode plates 210. When desirable, multiple flow channels may be provided to achieve more rapid, higher volume electroporation treatment.

Figure 30E:
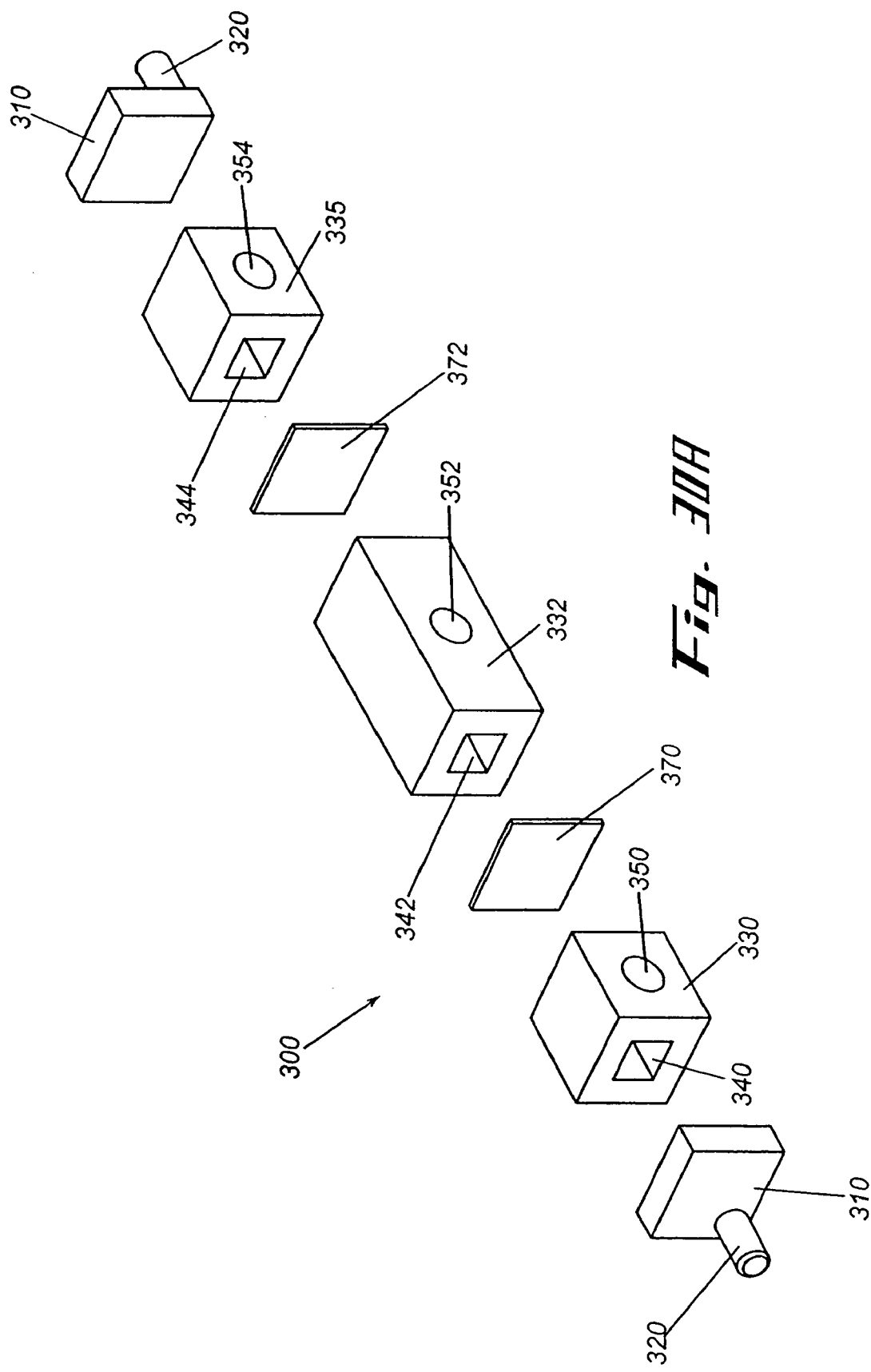
FIG. 30E is an end view of the flow electroporation cell assembly shown in FIG. 30B.
Figure 30B:
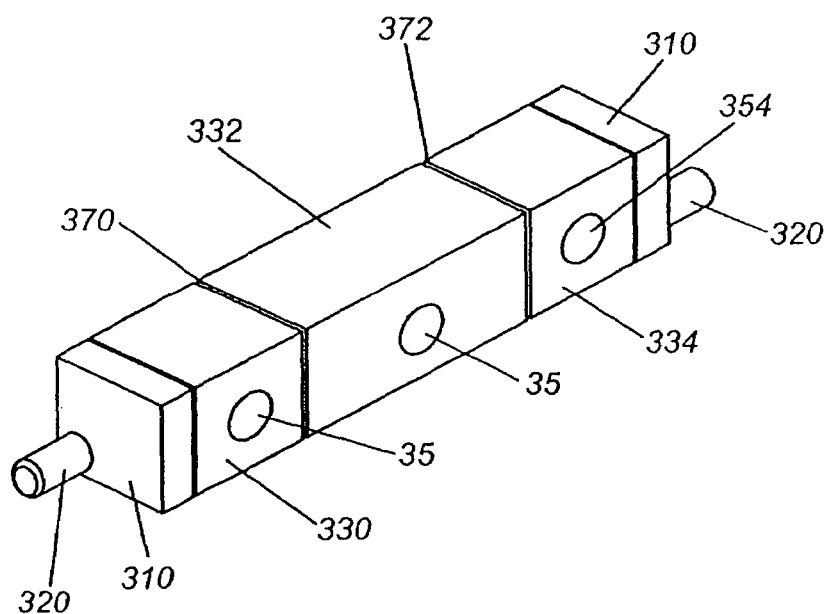
FIG. 30B is a perspective view of the flow electroporation cell assembly shown in FIG. 30A.
Figure 30C:
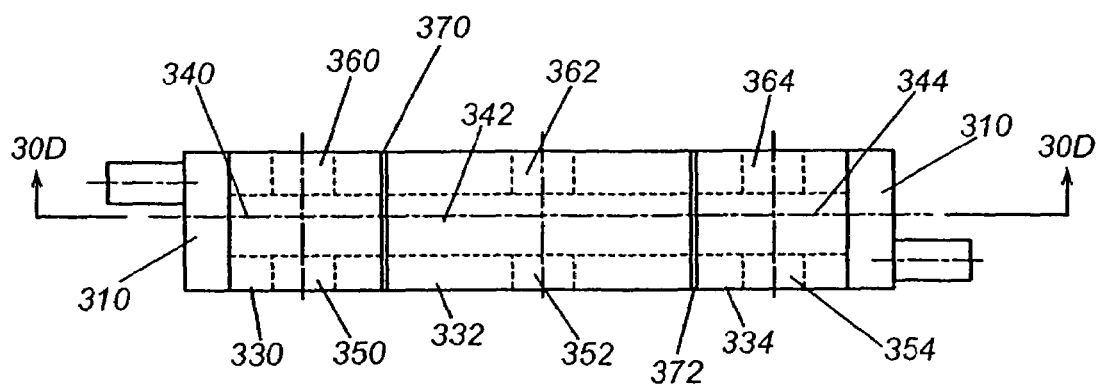
FIG. 30C is a side view of the flow electroporation cell assembly shown in FIG. 30B.

With reference to FIGS. 30A–30F, there is also disclosed an alternate embodiment for the electroporation cell of the present invention. As shown in FIG. 30A, a flow electroporation cell assembly 300 may be constructed of two opposing electrode plates 310. Typically, the electrode plates 310 may be constructed of iron, steel, copper, aluminum, or other electrically conductive metals or metal alloys. The electrode plates 310 may further be coated with gold, platinum, zinc, carbon, or other plating materials to enhance their electrical conductivity. Each electrode plate 310 may be provided with one or more electrical terminals 320 that interface with the power supply circuitry of the overall flow electroporation system. In alternate embodiments, one or both of the opposing electrode plates 310 may further be provided with an interface having a cooling element (not shown) as described above.

Referring still to FIG. 30A, the electrode plates 310 are separated by three electrode gap spacers 330, 332, 334. The thickness of the electrode gap spacers 330–334 will define and fix a gap 336 between the electrodes 310. The gap 336 between the electrodes 310 can easily be adjusted to any desired measurement simply by changing the electrode gap spacers 330–334. The electrode gap spacers 330–334 are typically constructed of an electrically insulating material, and may be fashioned from such materials as plastic, ceramic, rubber, or other non-conductive polymeric materials or other materials.

Each of the electrode gap spacers 330–334 defines a well 340, 342, 344, respectively. Each of the electrode gap spacers 330–334 also defines fluid inlets 350, 352, 354, respectively. The fluid inlets 350–354 permit fluid communication with the wells 340–344, respectively. Each of the electrode gap spacers 330–334 also defines fluid outlets 360, 262 and 364. The fluid outlets 360–364 permit fluid communication with the wells 340–344, respectively.

Interposed between the spacer 330 and the spacer 332 is a porous membrane 370. Interposed between the spacer 332 and the spacer 334 is another porous membrane 372. The porous membrane 570, 572 are made of a non-reactive material and has pore sizes that permit fluid to pass therethrough, but not materials that are being electroporated, such as cells.

Only the central sample well 342 is to contain material for electroporation, such as a suspension of particles, such as cells and expression vectors, while the side wells 340, 344 are filled with buffer or some other conductive fluid. In this case the central sample well 342 is still in electric contact with the electrodes 320 but the cells are kept far from the electrode surfaces, so that migration of metal from the electrodes does not affect the cells. During electroporation, gas bubbles are also formed at the electrode 320 surfaces. By isolating the cell suspension in the central sample well 342 and providing buffer in the outer wells 340, 344, the electrode bubbles remain in the outer sample wells and do not interact with the cells in the central sample well. Higher liquid flow rates can also be used in the outer wells 340, 344 so that gas bubbles formed at the electrodes 310 are more efficiently removed. Using the porous membranes 370, 372 serves the purpose to prevent mixing of buffer layers adjacent to electrodes 310 with the bulk of cell suspension, and keeps metal ions localized in the pores.

Figure 31D:
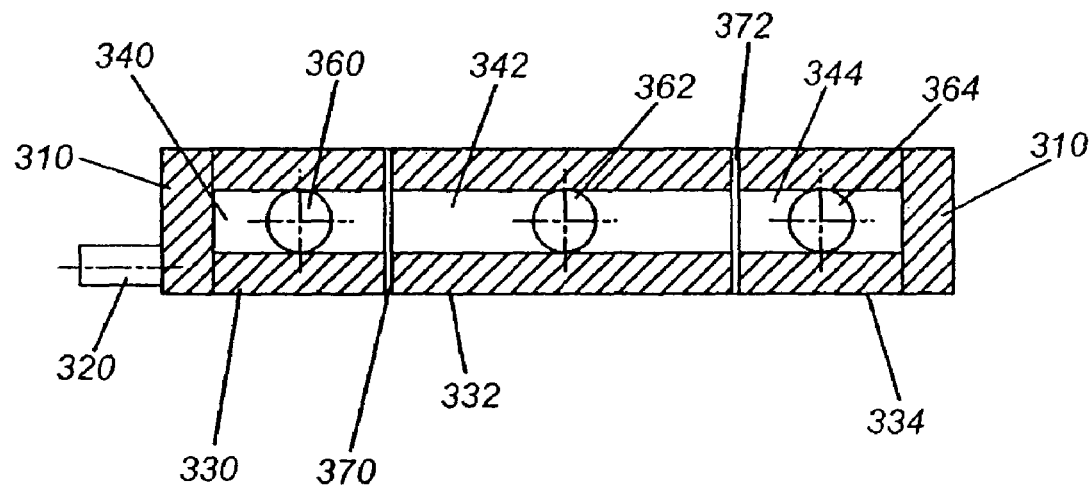
FIG. 31A is an exploded perspective view of a fifth disclosed embodiment of the flow electroporation cell assembly of the present invention.
FIG. 31B is a perspective view of the flow electroporation cell assembly shown in FIG. 31A.
Figure 31E:
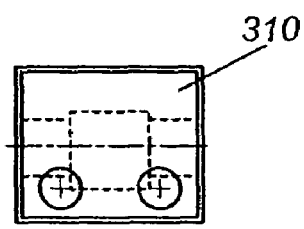
Figure 31F:
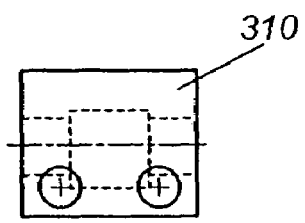
Figure 31A:
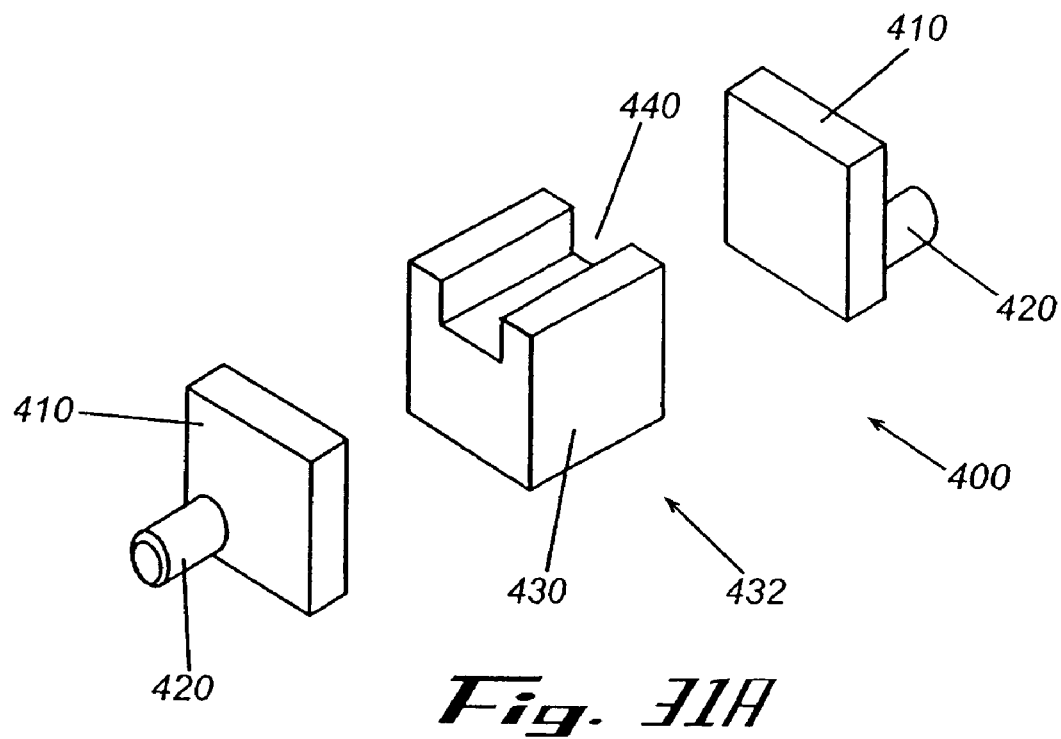
Figure 31B:
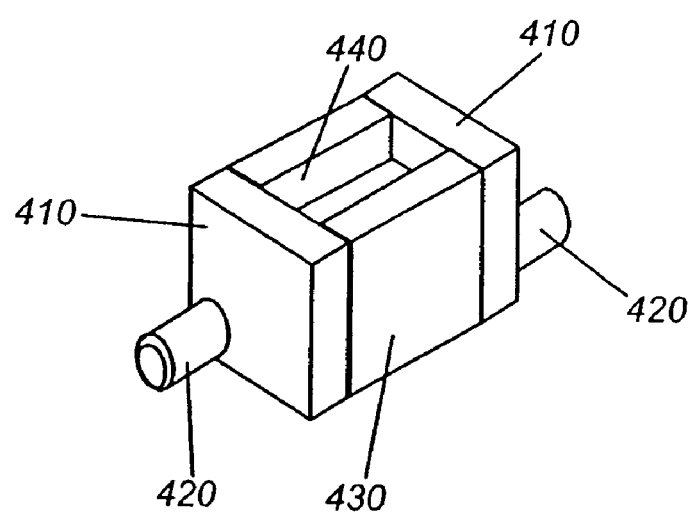

With reference to FIGS. 31A–31B, there is also disclosed an alternate embodiment for a static electroporation cell of the present invention. As shown in FIG. 31A, a static electroporation cell assembly 400 may be constructed of two opposing electrode plates 410. The electrode plates 410 may be constructed of iron, steel, copper, aluminum, or other electrically conductive metals or metal alloys. The electrode plates 410 may further be coated with gold, platinum, zinc, carbon, or other plating materials to enhance their electrical conductivity. Each electrode plate 410 may be provided with one or more electrical terminals 420 that interface with the power supply circuitry of the overall flow electroporation system.

The electrode plates 410 are separated by an electrode gap spacer 430. The thickness of the electrode gap spacer 430 will define and fix a gap 432 between the electrodes 410. The gap 432 between the electrodes 410 can easily be adjusted to any desired measurement simply by changing the electrode gap spacer 430. The electrode gap spacer 430 is typically constructed of an electrically insulating material, and may be fashioned from such materials as plastic, ceramic, rubber, or other non-conductive polymeric materials or other materials.

The electrode gap spacer 430 defines a sample channel 440 therein. The sample channel 440 is designed to contain material for electroporation, such as a suspension of particles, such as cells and an expression vector. The height and width of the sample channel 440 is approximately 2.0 mm to approximately 1 cm, preferably approximately 2.0 mm to 5 mm, most preferable approximately 3.0 to 5.0 mm. The length of the flow channel 440 is approximately 5 mm to 5 cm, preferably approximately 1.0 cm to 3.0 cm, most preferable approximately 1.2 cm. For the static electroporation cell in FIGS. 31A–31B, the electrode length is approximately 0.2 cm, the electrode width is approximately 0.45 cm and the electrode gap is approximately 1.2 cm.

Figure 32B:
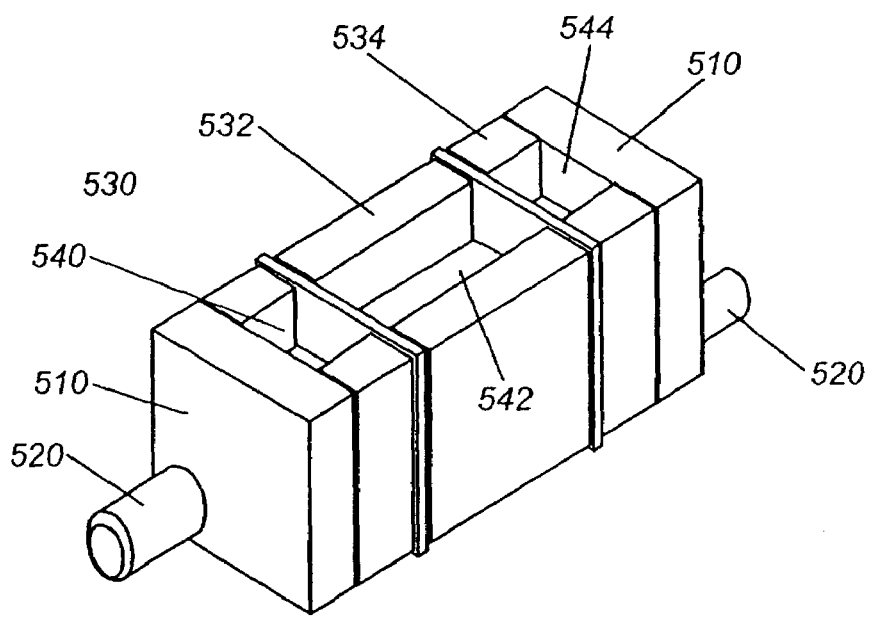
FIG. 32B is a perspective view of the flow electroporation cell assembly shown in FIG. 32A.
Figure 32C:
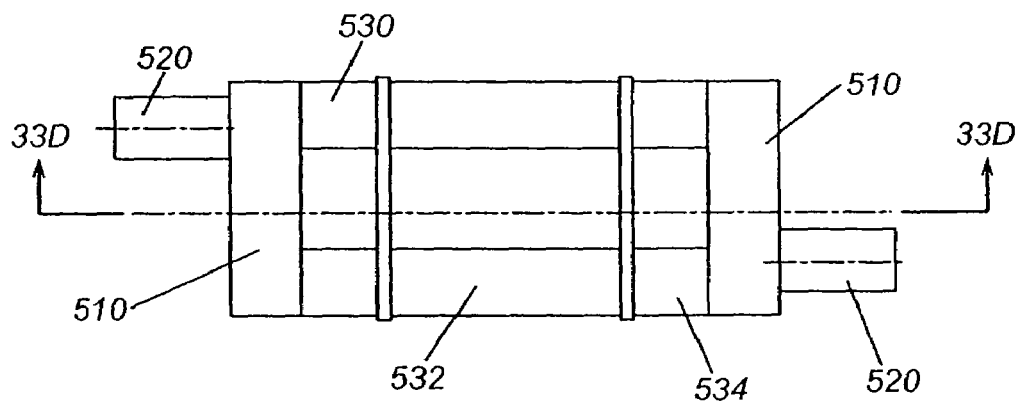
FIG. 32C is a side view of the flow electroporation cell assembly shown in FIG. 32B.
Figure 32D:
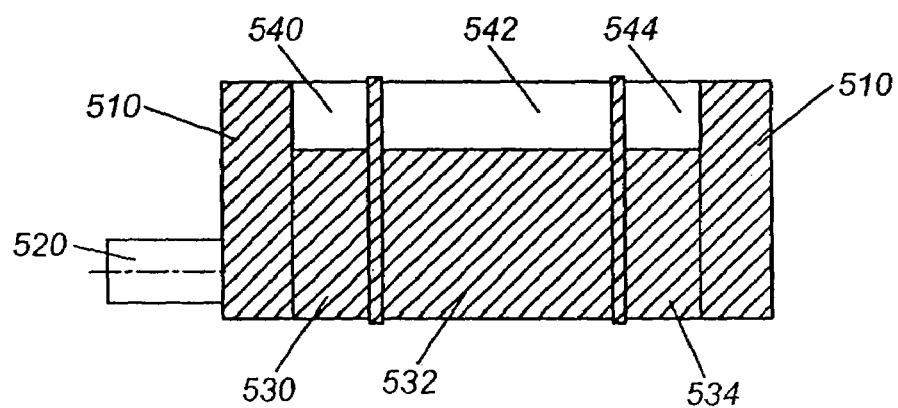
FIG. 32D is a side cross-sectional view taken along the line 33D—33D shown in FIG. 32C.

With reference to FIGS. 32A–32D, there is also disclosed an alternate embodiment for a static electroporation cell of the present invention. As shown in FIG. 32A, a static electroporation cell assembly 500 may be constructed of two opposing electrode plates 510. The electrode plates 510 may be constructed of iron, steel, copper, aluminum, or other electrically conductive metals or metal alloys. The electrode plates 510 may further be coated with gold, platinum, zinc, carbon, or other plating materials to enhance their electrical conductivity. Each electrode plate 510 may be provided with one or more electrical terminals 520 that interface with the power supply circuitry of the overall flow electroporation system.

The electrode plates 510 are separated by three electrode gap spacers 530, 532, 534. The thickness of the electrode gap spacers 530–534 will define and fix a gap 536 between the electrodes 510. The gap 536 between the electrodes 510 can easily be adjusted to any desired measurement simply by changing the electrode gap spacers 530–534. The electrode gap spacers 530–534 are typically constructed of an electrically insulating material, and may be fashioned from such materials as plastic, ceramic, rubber, or other non-conductive polymeric materials or other materials.

Each of the electrode gap spacers 530–534 defines a sample channel 540, 542, 544, respectively, therein. Interposed between the spacer 530 and the spacer 532 is a porous membrane 570. Interposed between the spacer 532 and the spacer 534 is another porous membrane 572. The porous membranes 570, 572 are made of a non-reactive material and has pore sizes that permit fluid to pass therethrough, but not materials that are being electroporated, such as cells.

Only the central sample channel 542 is designed to contain material for electroporation, such as a suspension of particles, such as cells and an expression vector, while the side wells 540, 544 are filled with buffer or some other conductive fluid. In this case the central sample channel 542 is still in electric contact with the electrodes 520 but the cells are kept far from the electrode surfaces, so that migration of metal from the electrodes does not affect the cells. During electroporation, gas bubbles are also formed at the electrode 520 surfaces. By isolating the cell suspension in the central sample channel 542 and providing buffer in the outer channels 540, 544, the electrode bubbles remain in the outer sample channels and do not interact with the cells in the central sample channel. Using the porous membranes 570, 572 serves the purpose to prevent mixing of buffer layers adjacent to electrodes 510 with the bulk of cell suspension, and keeps metal ions localized in the pores.

Suitable materials for use in any of the apparatus components as described herein include materials that are biocompatible, approved for medical applications that involve contact with internal body fluids, and should meet US PV1 or ISO 10993 standards. Further the materials will not substantially degrade, from for instance, exposure to the solvents used in the present invention, during at least a single use. The materials are typically sterilizable either by radiation or ethylene oxide (EtO) sterilization. Such suitable materials include materials that are extrudable if, for instance, used for tubing, and/or injection moldable if, for instance, used for hard containers. Materials useful to form the various components of the apparatus according to the present invention include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA) available as TEFLON PFA from E. I. du Pont de Nemours and Company, and combinations thereof.

In many cases it is important to refer to the throughput of electroporation process, or the amount of cell suspension processed in certain amount of time. Since it takes certain amount of energy to electroporate a unit of volume of cell suspension, the more volumetric units is processed in a given time, the more energy in the same time is consumed. Therefore, the speed, or the throughput, of a process can be unequivocally defined as the rate of energy consumption, or power, which is defined as the ratio of energy to time:

$$P = \frac{Q}{t}$$

It can be shown that big amount of heat is normally produced as a side effect of practically every electroporation process, what may cause irreversible damage to biologic material or live cells. Every electric field pulse can cause unwanted warming up of cell suspension by 20–30 degrees Celsius. To avoid or minimize this effect, cooling is often applied to suspensions of cells being electroporated, especially in the continuous; i.e., flow electroporation, processes.

However, while the cooling is usually provided by bringing cell suspension in immediate contact with metal parts which are in their turn being cooled by Peltier elements or by flow of air or fluid, some principal limitations to the cooling process exist. In many cases the designers of electroporation process either neglect or overlook the fact that thermal conductivity of metal is much higher that the one of water (or biological buffer), what means that transfer of heat from the flow channel to the cooling unit is always limited by the heat conductivity of water or, equivalently, the cell suspension itself. In such situation it is important to choose the proper geometry of the flow channel so that heat transfer is accomplished in the most efficient way. A straightforward derivation of the necessary parameters of an optimal design are shown below.

From the analysis of the heat flow equation:

$$Q = kA\frac{\Delta T}{\Delta x}t$$

where k is thermal conductivity of water [0.0061 W K$^{-1}$ cm$^{-1}$]

A is surface area of one electrode $\Delta T$ is the difference in temperature between the buffer and cooler $\Delta x$ is distance the heat has to travel inside the channel (one-half of the channel width, since the temperature of buffer is highest in the center of the channel or electroporation chamber) one can derive an important parameter called the thermal resistance $\Theta$ of the flow cell:

$$\Theta = \Delta T\frac{t}{Q} = \frac{\Delta x}{kA} = \frac{1}{2}\frac{w}{kA}$$

where w is the gap between electrodes.

This expression shows that thermal resistance is proportional to the width of a flow channel (the distance between electrodes) and inversely proportional to the area of an electrode. The lower the thermal resistance is the more efficient is the cooling, because heat has to travel a shorter distance and a larger area of contact with metal is available for its transfer.

Thermal resistance shows how large the temperature increase of a physical body will be if there is a continuous process of heat production within this body at the rate P. For example, if the thermal resistance is 10 degrees per Watt, one can state that the average temperature of the buffer will be 50 degrees above ambient (room temperature) if the power consumption in a continuous process is 5 Watts.

Normally one would want the temperature increase to be below 20 degrees because the cell suspension is subjected to electroporation at room temperature, what makes 20+20=40 degrees Celsius—even slightly more than the maximal temperature found in living beings. It is known that proteins denature at the temperatures as high as 50–60 degrees, so the choice of 40 degrees maximum for biological applications should be quite right. On the other end, the cooler temperature cannot be lower than 0° C., or freezing will occur. Therefore, the entire practical range of temperatures that the suspension of cells can be exposed to is 0 to 40 degrees C.

With this limitation in mind, one can calculate the maximal power rating of any flow electroporation chamber from its dimensions:

$$P_{max} = \frac{\Delta T}{\Theta} \text{ or } P_{max} = \frac{40 \cdot 2 \cdot k \cdot A}{w} \approx \frac{1}{2}\frac{A}{w}$$

If both A and w are measured in centimeters, $P_{max}$ is expressed in Watts. The value of $\Delta T$ value may vary depending on the temperature of electrodes: 0° C.<$\Delta T$<40° C.

The power rating allows deciding whether the geometry of electroporation chamber is optimal for required heat transfer. For example, in a continuous process where cell suspension is being electroporated at a given electric field strength and certain volume of this suspension must be processed in a given time, one can calculate the power consumption rate:

$P=VItN/T$, where

V is the magnitude of the voltage being applied to electrodes during each pulse, I is current flowing through the buffer during each pulse, t is the duration of each pulse;

N is the number of pulses applied during the process,

T is the time of the process;

For example, if 50 pulses of 1 ms duration and 500 Volts magnitude are applied to a flow cell in a process that takes 10 minutes, and the current during each pulse is 100 Amperes, the power consumption is:

500*100*0.001*50/600=4.2 Watts

If P (power consumption) is found to be higher than $P_{max}$ (flow-cell power rating), the conditions for optimal heat transfer are not satisfied. In this case either the process has to be slowed down to produce less heat, or a different flow cell must be used which has a higher ratio of electrode area to the distance between electrodes. According to the present invention, the dimensions of the electrodes, area of their contact with suspension, and the distance between the electrodes is chosen to ensure that the thermal resistance of the entire flow channel is less than approximately 10° C. per Watt; preferably less than approximately 9.5° C. per Watt, more preferably less than approximately 9° C. per Watt, more preferably less than approximately 8.5° C. per Watt, more preferably less than approximately 8° C. per Watt, more preferably less than approximately 7.5° C. per Watt, more preferably less than approximately 7° C. per Watt, more preferably less than approximately 6.5° C. per Watt, more preferably less than approximately 6° C. per Watt, more preferably less than approximately 5.5° C. per Watt, more preferably less than approximately 5° C. per Watt, more preferably less than approximately 4.5° C. per Watt, more preferably less than approximately 4° C. per Watt, more preferably less than approximately 3.5° C. per Watt, more preferably less than approximately 3° C. per Watt, more preferably less than approximately 2.5° C. per Watt, more preferably less than approximately 2° C. per Watt, more preferably less than approximately 1.5° C. per Watt. It is especially preferred that the flow channel of the present invention has a thermal resistance of approximately 0.1° C. per Watt to approximately 10° C. per Watt; more preferably approximately 0.5° C. per Watt to approximately 4° C. per Watt, more preferably approximately 1° C. per Watt to approximately 3° C. per Watt, more preferably approximately 1.5° C. per Watt to approximately 2.5° C. per Watt.

Thermal resistance of the flow channel can also be calculated by measuring certain parameters as described below. Temperature sensors, such as thermocouples, may be placed at the inlet, such as at 50 (FIG. 14), and the outlet, such as at 55 (FIG. 14), of the flow cell so that the temperature of the suspension going into and out of the flow cell can be measured. A steady flow of buffer, such as PBS, is then established through the flow channel. A preferred flow rate is approximately 0.01 to 0.1 mL/s (generally low flow rates are preferred). In the absence of any electric filed applied to the cell, the temperature of the buffer at the inlet and at the outlet is measured to verify that there is no difference. The pulsing parameters are then set on the electronic control module. A preferred set of parameters is a field strength of 1–2 kV/cm with a pulse width of 1–2 ms and 1–2 seconds between pulses. Using pulses of alternating polarity is preferred in order to avoid electrode polarization. Measurement of the applied voltage to the electrodes, current through the flow channel and inlet and outlet temperatures are recorded, such by digitizing those measurements and feeding that information into a computer. Pulsing of the flow channel is then begun while repetitive reading of voltage, current and temperature are taken and recorded as often as possible during and covering a period (the measurement period) of at least 50 pulses. Thermal resistance can then be calculated based upon the collected data as described below.

All outlet temperature readings are averaged and stored as $T_{out}$. All inlet temperature readings are averaged and stored as $T_{in}$. The difference between Tout and Tin is calculated and stored as T. Multiply paired readings of voltage (in Volts) and current (in Amperes) during each pulse and average them. Store the result as P. Multiply duration of each pulse by the total number of pulses applied during the measurement period and store the result as $D_{pulse}$. Set $D_{exp}$ equal to the duration of the measurement period (make sure to use the same units for time as with the pulse width). Then, calculate the value of heat resistance as $Q=(T*D_{exp})/(P*D_{pulse})$.

It is to be understood that the flow electroporation system of the present invention can be used in conjunction with commercially available cell separation apparati. These include, but are not limited to, Haemonetics Cell Save® 5 autologous blood recovery system, the Haemonetics Ortho-PAT® System, the Haemonetics MCS®+ Apheresis System, the Cobe Spectra Apheresis System, the Trima™ Automated Blood Component Collection System, the Gambro BCT System, and the Baxter Healthcare CS-3000 Plus blood cell separator. The flow electroporation system of the present invention can be in direct communication with these commercially available cell separation apparati so that the cells that are isolated can be introduced into the flow electroporation system of the present invention and treated as desired.

EXAMPLE 1

Electroporation of Red Blood Cells with IHP

It has been determined that one of the most important parameters to control is production of heat. Red blood cells are extremely sensitive to heat and this was found to be an important parameter in the inefficiency of prior art electroporation methods. The following example was performed using the apparatus described herein.

Figure 12:
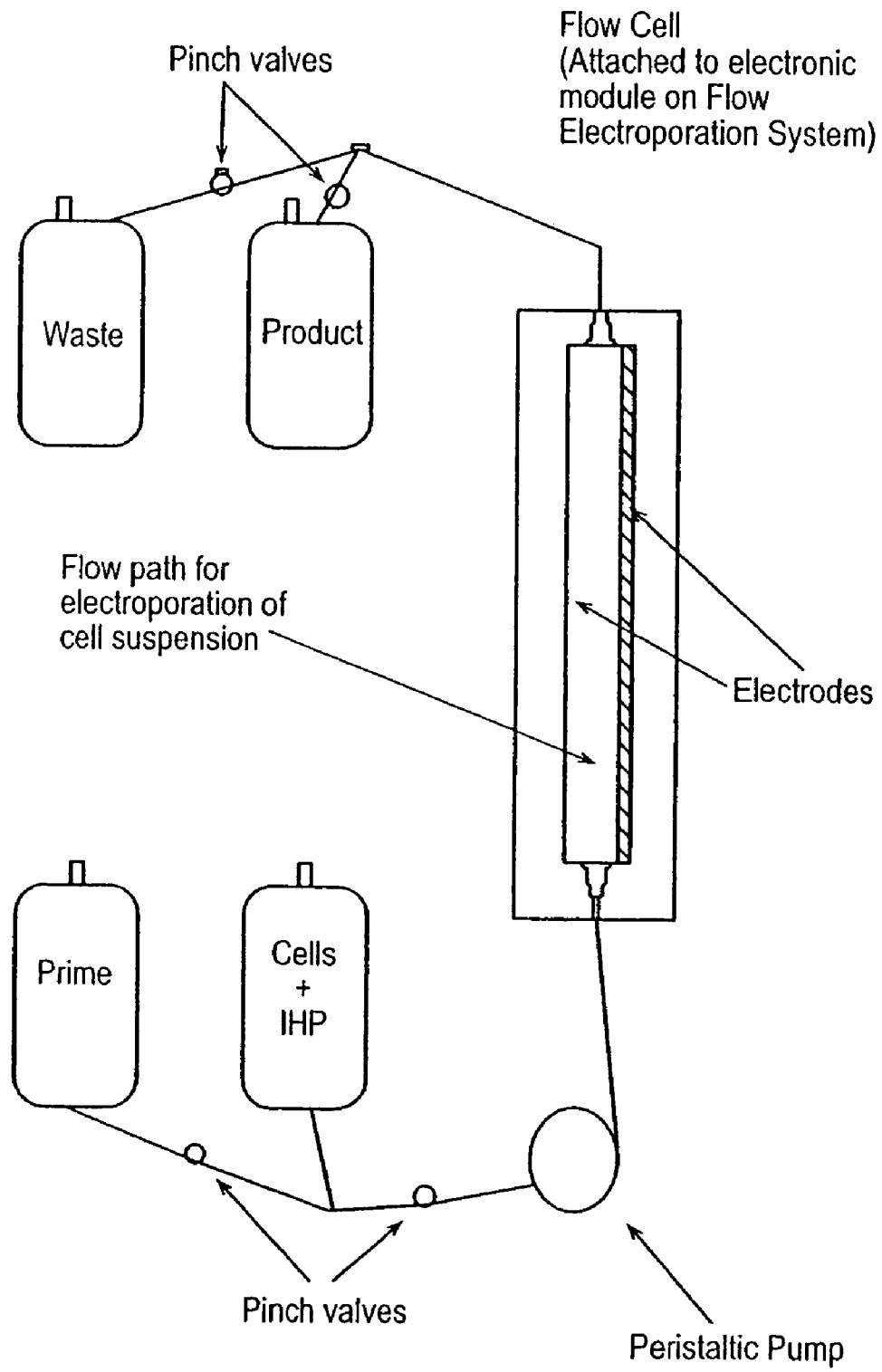
FIG. 12 is a schematic diagram of the disposable unit.

60 mL of blood is collected from a human donor into a collection set containing 15 to 20 m of CPDA-1 (21 CFR 640.4) buffer 26.3 g trisodium citrate 3.27 g citric acid: 31.9 g dextrose: 2.22 g monobasic sod phosphate: 0.275 g adenine:, $H_2O$ to 1000 mL. The volume per 100 ml of blood is 14 mL. It is to be understood that larger volumes of blood can be treated with the present invention. The blood is transferred to two 50 ml centrifuge tubes and then is centrifuged for 10 minutes at 2000 g. The plasma is collected from above the cell pellets and transferred into a separate sterile 50 ml tubes and stored. The buffy coat is removed from the top of the cell pellets using a plastic transfer pipette. The cells are then resuspended in 50 ml of sterile phosphate buffered saline by gently inverting the tubes. The resuspended cells are centrifuged at 2000 g for 5 minutes. The supernatant is discarded and the resuspension/centrifugation procedure is repeated. The red blood cells are then resuspended in 45 ml of electroporation buffer. The electroporation buffer is 35 mM Na6-IHP (EntreMed, Rockville Md.,), 60 mM KCl, and 10 mM D-glucose. The cell suspension is centrifuged at 2000 g for 5 minutes. The volume of the red blood cell pellet is estimated visually and approximately 1.5 times the volume of the pellet of electroporation buffer is added to the cells. The cells are resuspended in the electroporation buffer by gently inverting the tubes. Insert syringe ports onto cell suspension bags (Baxter Transfer Packs, Baxter Healthcare, Chicago Ill.) clamp tubing onto the bags with hemostats. Transfer the cell suspensions from both tubes into the first bag using 30 ml syringes and plastic needles. After the last injection of cells, pull out 15 ml of suspension and dispense the cells into a separate 50 ml tube for control. The second bag is filled with 30 ml of electroporation buffer. With reference to FIG. 12, install a disposable set on the flow electroporation device (described above). Matching the bag and valve numbers, the tubing is inserted into the four pinch valves and the appropriate part of the harness on the peristaltic pump is installed. The pump key and compression plate is closed.

The computer software is then initialized and the hemostats are removed from the bags. The pump is primed by clicking on the "prime start" button on the GUI. The pump is started by clicking on the "pump on" button on the GUI. This begins the electroporation process. When the blood flow reaches the waste bag, the stream is switched so the sample is collected in the product bag by clicking the "sample start" button. The pulsing schedule with preferred ranges is shown below in Table 6:

TABLE 6

| Parameter | Preferred value | Range of values |
|---|---|---|
| Pulse width | 650 μs | 200 to 900 μs |
| Interval between pulses | 100 μs | 25 to 400 μs* |
| Pulses in burst | 2 | 1 to 6 |
| Time between bursts | 12000 ms | 1000 to 20000 |
| Bursts/cell | 2 | 1 to 5 |

*The interval between bursts is dependent on the flow rate and the volume of the flow cell.

Figure 18:
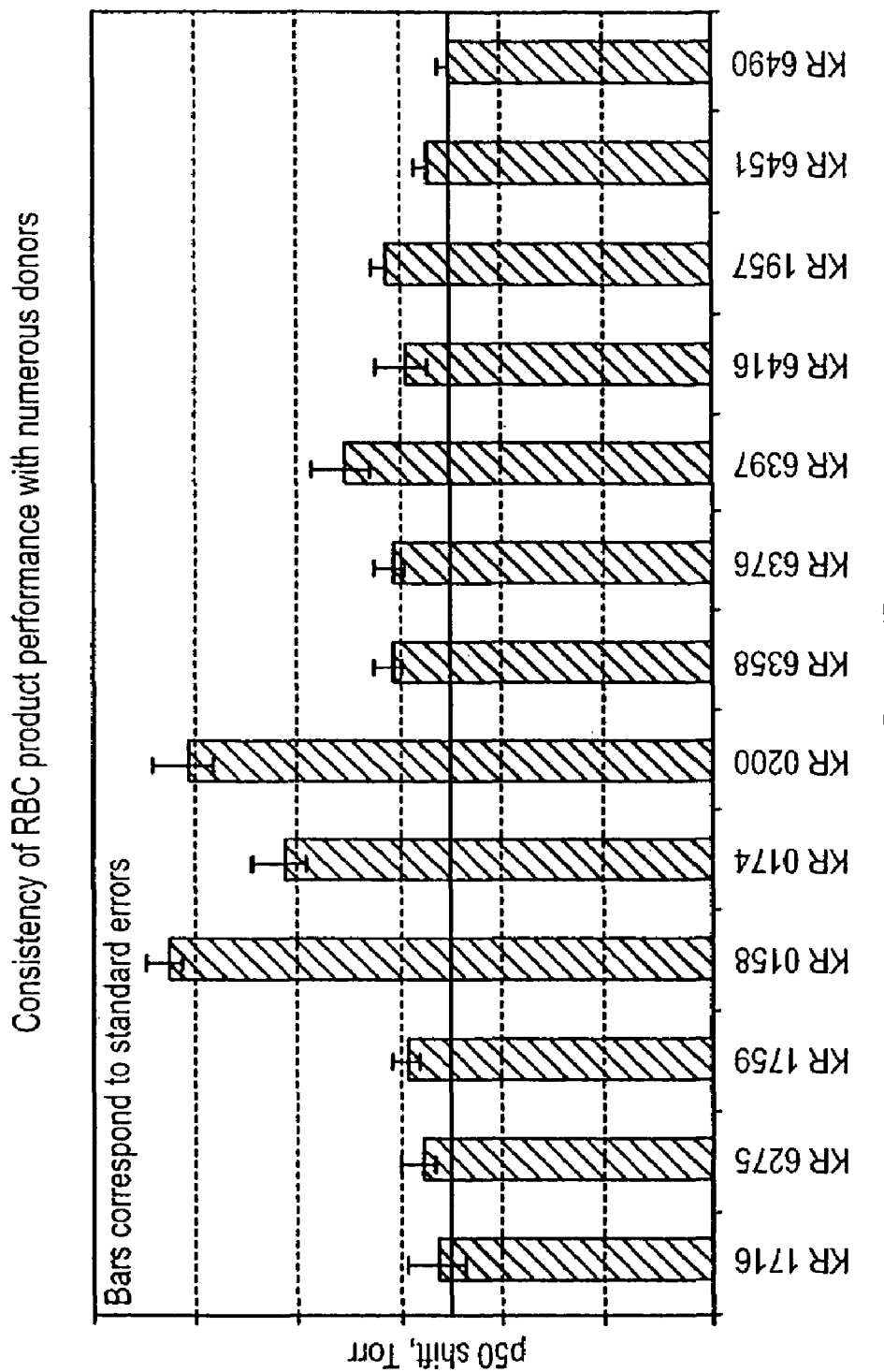
FIG. 18 is a graph showing the average right shift of the oxygen dissociation curve for several samples of red blood cells that have been electroporated in the presence of IHP.

When the bag containing the blood is empty, the pulsing is stopped by clicking the "off" button on the GUI. The bag with the treated blood is then placed into a sealable plastic overwrap (a ZIPLOC baggie) and put into a water bath at 37° C. for 45 minutes. The bag tubing is then aseptically cut and the sample is divided into two 50 ml centrifuge tubes. 7.5 mL of the cell suspension from each tube is transferred to a separate 50 ml tube for testing. The remaining cell suspension is centrifuged at 2000 g for 5 minutes. The cells are washed 3 times by centrifugation in sterile PBS with 60 mM mannitol. It has been found that mannitol is important in the wash buffer and stabilizes the cell membrane better than other compounds. Other polyhydroxyl hydrocarbons can be used in the present invention to stabilize the cell membrane. The concentration of mannitol is preferably between 30 mM and 90 mM, a more desirable concentration of between 40 and 80 mM with the most desirable concentration of between 50 and 7 mM. The red blood cell volume is estimated visually and 1.5 times the volume of the pellet of the stored plasma is added to each tube. The red blood cells are resuspended by inverting the tubes. The right shift of the oxygen hemoglobin curve is measured in the treated cells and the untreated cells using an Oximeter. Saturation of hemoglobin with oxygen ($sO_2$) was measured after the incubation step in both control and electroporated red blood cell samples with a CO-Oximeter™ Model 682 (Instrumentation Laboratory). Each sample was divided into three fractions, which were equilibrated for 20 minutes at 37° C. with three gas mixtures in an EQUILibrator tonometer (RNA Medical). The gas mixtures were obtained from RNA Medical and contained 9%, 6% and 3% oxygen, plus 5.6%, 2.8% and 1.4% $CO_2$, respectively, and were balanced with nitrogen. The partial pressure of oxygen (pO2) in each fraction and the buffer pH were measured by a model 1640 pH/BloodGas/Electrolytes device (Instrumentation Laboratory). Viability is measured by measuring free hemoglobin. The results of electroporation of several different samples of blood from different donors are shown in FIG. 18. The average red blood cell loss during the entire electroporation process was between 6% and 10%.

EXAMPLE 2

To Electroporate Non-stimulated Lymphocyte

Primary lymphocytes were suspended in B&K buffer (125 mM KCl, 15 mM NaCl, 1.2 mM $MgCl_2$, 3 mM glucose, 25 mM Hepes, pH 7.4) cell concentration was set from $1\times10^7$ cells/mL to $6\times10^8$ cells/mL together with DNA plasmid from 50 µg/mL to 1 mg/mL. DNA concentration was 50 ug/mL–1000 ug/mL. Electroporation was performed at 2.3 kV/cm, 400 µs, 4 pulses for small volume experiments (15 µl) or 2.2 kV/cm, 1.6 ms, 1 pulse for large volume experiments (0.5 ml–2 ml) was performed under static conditions at room temperature. Following electroporation, cells were incubated in B&K buffer for 20 minutes at 37° C. for small volume experiments, or diluted by 10×volume of culture medium (RPMI-1640+10% fetal bovine serum+1% Pen-strep+2 mM L-glutamine) for large volume experiments. Cells were not diluted for post pulse incubation. Cells were cultured in culture medium for various periods (up to 72 hours) and the transfection efficiency was analyzed.

Primary quiescence lymphocytes have been shown to be refractory to retrovirus based gene transfer. HIV based vectors can transduce primary lymphocytes, but the efficiency is extremely low in the absence of HIV accessory genes. Other non-viral transfection methods also gave very low transfection efficiency. This is the first demonstration of high efficiency of transfection of primary lymphocytes by a non-viral method.

EXAMPLE 3

Electroporation of Stimulated Lymphocytes

Primary lymphocytes ($5\times10^6$ cells/mL) were stimulated with PHA-P (up to 10 µg/mL) and 10 U/mL hr IL-2 for 48 hours in culture medium (RPMI-1640+10% Fetal bovine serum+1% Pen-strap+2 mM L-glutamine). Large cell aggregates were collected by incubating the cells in a 15 ml centrifuge tube for 10 min in the incubator and re-suspended in B&K buffer with 200 µg/mL of plasmid DNA. Following electroporation under static conditions at 1.8 kV/cm, 400 µs, 4 pulses, cells were incubated for 20 min in B&K buffer at 37° C. for small volume experiments or diluted with 10×volume of culture medium containing 20 U/mL hr IL-2. Cells were cultured with culture medium containing 20 U/mL IL-2 for various periods (up to 20 days) and the transfection efficiency was analyzed.

This is the first demonstration of gene transfer of large amount of (greater than $1\times10^8$ cells) stimulated-lymphocytes by a non-viral method.

EXAMPLE 4

Transfection Efficiency Analysis

Seven transgenes (Ds-Red, eGFP, βGal, hEndostatin, hEPO, hIFNα, hIL-2) were tested in these experiments. As used herein, a transgene is any gene that is transferred into a cell that codes for a protein. Ds-Red is under the control of CMV promoter, and is from ClonTech., eGFP is under the control of CMV early promoter with an intron, backbone is from Promega, βGal is under the control of CMV promoter, and is from Clontech. hEndostatin is under the control of CMV promoter, and the backbone is from Invitrogen (pcDNA3.1). hEPO, hIFNα and IL2 are under the control of CMV promoter and an intron. The backbone is from Promega. When pCMV-Ds-Red or pCMV-EGFP was used, the percentage of the fluorescent cells was counted, by FACS or by manual counting under phase contrast and fluorescence microscope, as the transfection efficiency. When pCMV-βGal was used, the percentage of stained cells (blue cells) by in-situ staining with X-gal was used as the transfection efficiency. When pCMV-Endostatin was used, the Endostatin concentration in the supernatant was analyzed by ELISA kit from Cytimmune Sciences, Inc. (College Park, Md.). For pCMV-EPO electroporation, the erythropoietin concentration in the supernatant was analyzed by R&D ELISA kit (Minneapolis, Minn.). The results of the transfection efficiency analysis are summarized in Table 7 below.

TABLE 7

Summary of Transgene Efficiencies

| Transgene | Cell Line | Viability | Flow or Static Electroporation | Efficiency (either by % of + cells or secretion level) |
|---|---|---|---|---|
| Ds-Red | resting Lymphocytes | 50% | Static | 30% |
| eGFP | resting Lymphocytes | 60% | Static | 50% |
|  | stimulated | 50% | Static | 40% |

TABLE 7-continued

Summary of Transgene Efficiencies

| Transgene | Cell Line | Viability | Flow or Static Electroporation | Efficiency (either by % of + cells or secretion level) |
|---|---|---|---|---|
| | Lymphocytes | | | |
| | CHO | 85% | Flow | 80% |
| | NIH 3T3 | 85% | Flow | 70% |
| | 10T1/2 fibroblast | 85% | Flow | 75% |
| | Huh-7 | 90% | Flow | 80% |
| | Jurkat cells | 85% | Flow | 70% |
| βGal | resting lymphocytes | 40% | Static | 15% |
| hEndostatin | resting lymphocytes | 50% | Static | 10 ng/million cells/24 hr |
| | Stimulated lymphocytes | 40% | Static | 30 ng/million cells/24 hr |
| hIFNα | stimulated lymphocytes | 40% | Static | 20 ng/million cells/24 hr |
| hIL-2 | Jurkat cells | 60% | Static | 2500 pg/million cells/24 hr |
| hEPO | stimulated lymphocytes | 45% | Static | 200 ng/million cells/24 hr |
| | NIH 3T3 cells | 80% | | 3000 ng/million cells/24 hr |

EXAMPLE 5

Application of the Present Invention in Ex Vivo Gene Therapy

Genes encoding therapeutic proteins can be incorporated into a patient's autologous cells by the flow electroporation system of the present invention. Human erythropoietin (hEPO) was used as a marker gene to demonstrate the concept of the ex vivo gene therapy process. Mouse NIH3T3 cells were used as gene delivery vehicles, but in real life setting, any human primary cells can be employed into the system, such as T lymphocytes, stem cells, fibroblast, myoblast, and pancreatic cells.

The human erythropoietin (hEPO) gene was RT-PCR amplified from polyA+ human kidney RNA (Clontech, Palo Alto, Calif.) using synthetic oligonucleotides upstream primer 5'-CTCGAGATGGGGGTGCACGAATGTCCT-GCC (SEQ ID NO: 1) and downstream primer 5'GTC-GACTCATCTGTCCCCTGTCCTGCAGGC (SEQ ID NO: 2) and cloned into pCR2.1-TOPO (Invitrogen, Carlsbad, Calif.). Then the coding region for hEPO was excised by EcoRI and cloned into the mammalian expression plasmid pTM4 to construct pTM7 (CM V-hEPO-IRES-eGFP).

Plasmid pTM7 was propagated and band purified twice by CsCl gradient. Endotoxin level was <3 EU/mg. Purified plasmid was re-suspended in endotoxin free $H_2O$ and stored at −20° C.

NIH3T3 mouse fibroblast was cultured according ATCC guidelines and re-suspended in B&K pulsing buffer (125 mM KCl, 15 mM NaCl, 1.2 mM $MgCl_2$, 25 mM Hepes, 3 mM Glucose, pH 7.4) and transfected with pTM7 (100 µg/mL) using the flow electroporation system of the present invention: 2.1 KV/cm, 400 µs, 4 pulses at 1.25 second intervals, and flowing at 0.1 mL/s. Then, the fibroblasts were incubated in the pulsing medium for 20 minutes before injected into SCID mouse. Flow analysis revealed that about 75% of cell population expressed eGFP.

Figure 19:
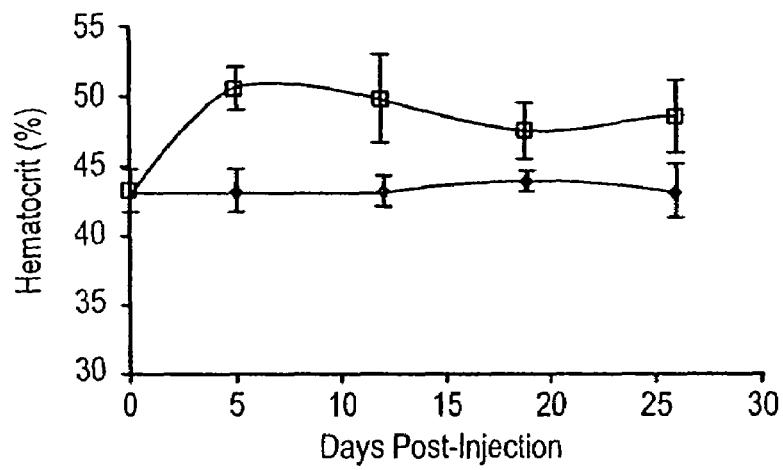
FIG. 19 is a graph showing the effects of large volume fibroblasts transfected with human erythropoietin (hEPO) gene on the hematocrit of mice.

Each SCID mouse was SQ injected with $2\times10^6$ hEPO transfected cells. Control group was injected with non-transfected cells. Mice were bled at 5 days, 12 days, 19 days, and 26 days post-injection. The blood was collected using a heparinized capillary tube. The hematocrit was measured using standard procedures. The results of this series of experiments are shown in FIG. 19.

EXAMPLE 6

Application of the Flow Electroporation System of the Present Invention in Drug Target Discovery Treatment of cells to effect the intracellular loading of short nucleic acid molecules, or oligonucleides, that are fluorescently labeled, such labeled oligonucleotides often referred to as molecular beacons (MB) can be used for new drug target screening. A typical molecular beacon contains a fluorescent moiety at one end and a moiety that can quench the fluorescence of the fluorescent moiety attached to the other end. When the molecular beacon oligonucleotide is unbound the quench moiety is in proximity to the fluorescent moiety and it quench fluorescence. When the oligonucleotide is bound to a nucleic acid having a complementary sequence the quenching moiety is held distant from the fluorescent moiety and cannot quench its fluorescence. When a molecular beacon enters a live cell that express this target, the molecular beacon may bind to mRNAs that are expressed in the cell which contain sequences complementary to those of the molecular beacon. Such bind will result in the molecular beacons being made fluorescent. Such intracellular fluorescence may be detected microscopically or by flow cytometry, thereby revealing cells that are transcribing a particular gene. This information can be used to identify candidate gene and proteins useful in the discovery of new drugs.

Figure 20:
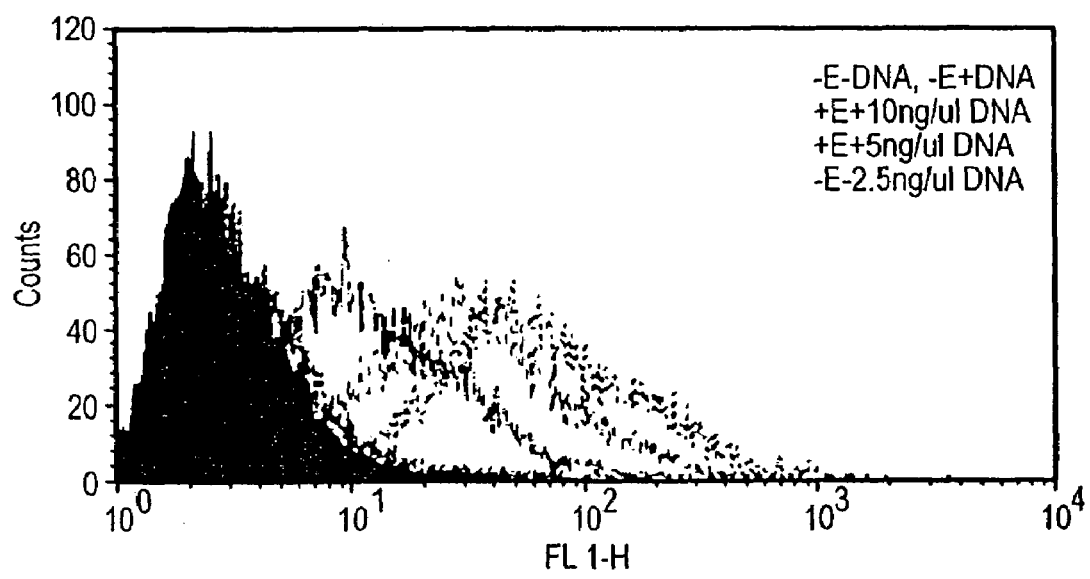
FIG. 20 is a graph showing electroporation mediated DNA oligo uptake by mammalian cells.
Figure 21:
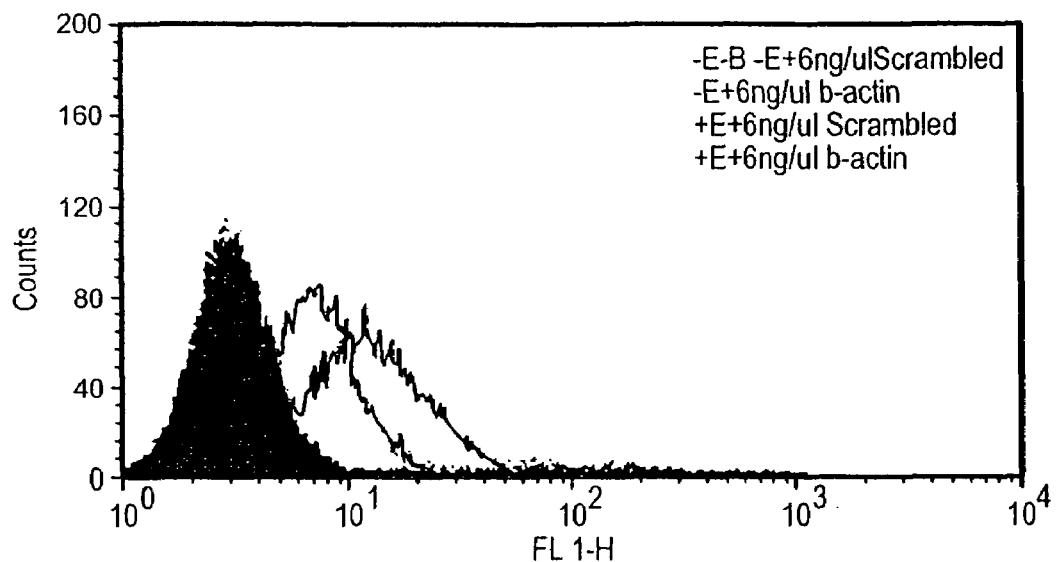
FIG. 21 is a graph showing fluorescence difference was observed when β-actin (blue) or scrambled DNA (orange) MBs were incorporated into Jurkat cells by electroporation.

A molecular beacon specific to the human β-actin mRNA is used as an example, and a molecular beacon having a random sequence is used as a negative control. Jurkat cells are re-suspended in B&K medium, pH 7.4, (125 mM KCl, 15 mM NaCl, 3 mM Glucose, 25 mM Hepes, 0.5 mM $MgCl_2$). The cells are electroporated four times with 1 kV/cm, 400 µsec/pulse with 1 second between pulses. Then, cells are incubation at 37° C. for 20 minutes. Before FACS, cells are washed twice in PBS. About 1 hour post-electroporation, cells are analyzed by flow cytometry. In FIG. 20, electroporation mediated uptake of the molecular beacon by mammalian cells is shown. Uptake of the molecular beacon is concentration dependent. Uptake efficiency is over 88%, while viability is approximately 90%. FIG. 21 shows a fluorescence difference when β-actin (blue) or scrambled DNA (orange) molecular beacons were incorporated into Jurkat cells by electroporation. This suggests that β-actin is expressed and positively recognized by the specific molecular beacon. Thus, an RNA expression profile of cells being treated with a known drug can be obtained and used as a template to screen for other unknown drugs. Using this method, many new drugs or compounds can be identified and replace current treatments.

EXAMPLE 7

Application of the Flow Electroporation System of the Present Invention in Viral Vector Production Retroviruses are widely used vectors in clinic trials for gene therapy. Retroviral vectors are generally produced using genetically packaging cell lines. All packaging cell lines used to date for this purpose grow as adherent cells. Recently, Chan et al., and Pizzato et al. reported stable suspension packaging cell lines derived from human lymphoblastic cells (Gene Ther 2001 May) providing proof-of-principle that cells grown in suspension can be used to produce retroviral vectors. Since cells grown in suspension can be grown in large quantity more easily and at lower cost than adherent cells, use of suspension cells as packing cells can reduce the cost of production of retroviral vectors. Additionally, while packaging cell lines have been used for retroviral vector production, it is possible to produce retroviral vectors without the use of packaging lines by co-transfection of cells with multiple plasmids each carrying different genes leader for assembly of an complete retroviral vector. Current protocols for transient co-transfection of cells are inefficient and not adapted to the transfection of large numbers of cells thereby severely limiting The concentration of retoroviral vector produced following co-transfection and the total amount of retroviral vector produced.

Figure 22:
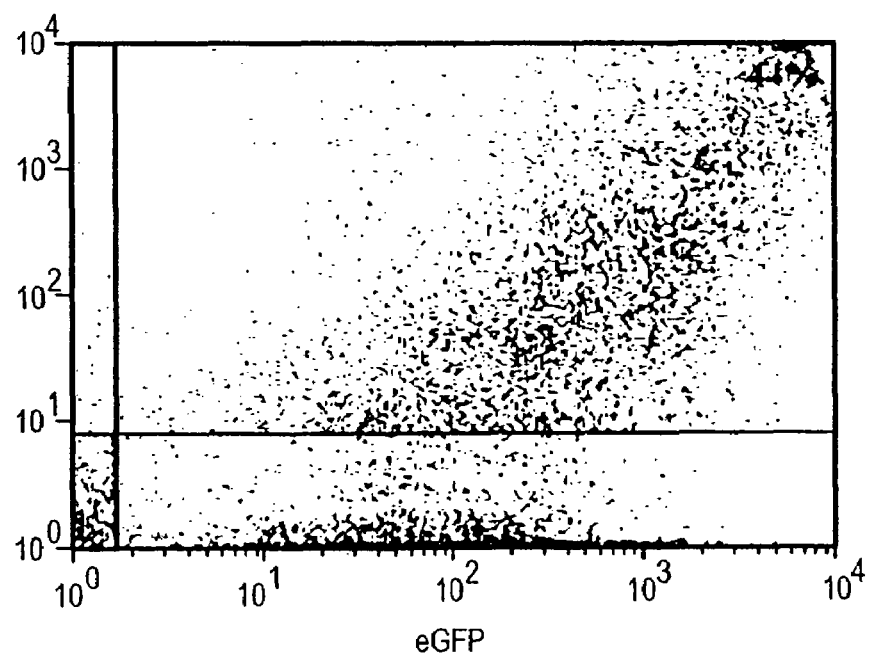
FIG. 22 is a graph showing the efficiency of co-transfected cells.

Cultured CHO cells were trypsinized and re-suspended in B&K buffer pH7.4, (125 mM KCl, 15 mM NaCl, 3 mM Glucose, 25 mM Hepes, 0.5 mM MgCl). Then plasmid 1 (pCMV-Ds-Red), and plasmid 2 (pCMV-intron-eGFP) were added in the cell suspension at 200 μg/mL. The cell-DNA mixture was introduced into the flow electroporation system. FACS was conducted 48 hours post electroporation. As shown in FIG. 22, more than 85% of the cell population expressed eGFP, while 44% of the cells expressed Ds-Red. Viability of the cells was >90%. The difference between these two transgene expressions may be due to the fact that green fluorescence is more sensitive than red fluorescence, and that eGFP was driven by CMV-intron, which has been shown more efficient than CMV alone.

Current lentiviral vector production involves transient co-transfecting cells with either 2 or 3 (preferably 3) different plasmids. $CaPO_4$ transfection can be used to co-transfect 2 or more plasmids, but the low efficiency of this method makes it impractical for clinical applications. The flow electroporation system of the present invention provides transfection efficiency sufficiently high and by allowing for the transfection of large volumes of cells provides a practical method for the production of retroviral vectors without use of packaging cell lines. More than 20 mL of cells at $200 \times 10^8$ cells/mL can be transfected with the flow electroporation system of the present invention (in all, $4 \times 10^9$ cells) in less than 1 hour.

EXAMPLE 8

Platelets migrate to disrupted vascular sites because their membrane contains receptors for proteins that are found there (e.g., fibrin and collagen). These proteins are also found at sites of infection and metastasis —if otherwise toxic drugs can be inserted into platelets, the platelet can be utilized as a drug delivery system (an "intelligent liposome").

Results are shown in Table 8 below. Efficacy is expressed as the percentage of cells that took up fluorescent markers (calcein or albumin+fluorescein). "Activity" was determined by measuring biologic functions, such as secretion or aggregation (for MaxCyte's application, any detectable level will probably suffice). "Survival" is the circulating half-life in an animal model.

TABLE 8

PLATELET: LABORATORY RESULTS

| | Efficacy (% of cells with marker) | Activity (% of control) | Survival (% of control) | Processing Rate (cells/min) |
|---|---|---|---|---|
| Human platelets CALCEIN | 80+ | 40–60 | 30–40 | 1 to 2 billion |

Platelets are primarily known as components of the haemostatic mechanisms and, in that role, traffic to sites of vascular injury to form an aggregate with coagulation factors and to stop vascular leakage. Targeting is accomplished via the biological properties of the platelets themselves. Specialized molecules on the platelet surface (receptors) specifically interact with proteins found not only at areas of vascular damage, but also at sites of infection, metastasis, and inflammation. The target proteins include fibrinogen, collagen, von Willebrand Factor (vWF), and adhesion proteins such as ICAM-1.

The concept that a biologically active agent can be inserted into platelets with electroporation and that the agent will then exert an effect at a target site has been demonstrated and is documented in peer-reviewed literature. In these cited studies, platelets were treated with static systems that accommodated a maximum of 0.5 ml of cell suspension. The MaxCyte system permits processing of tens or hundreds of milliliters of cell suspension with a rapid (minutes) throughput time.

Figure 23A:
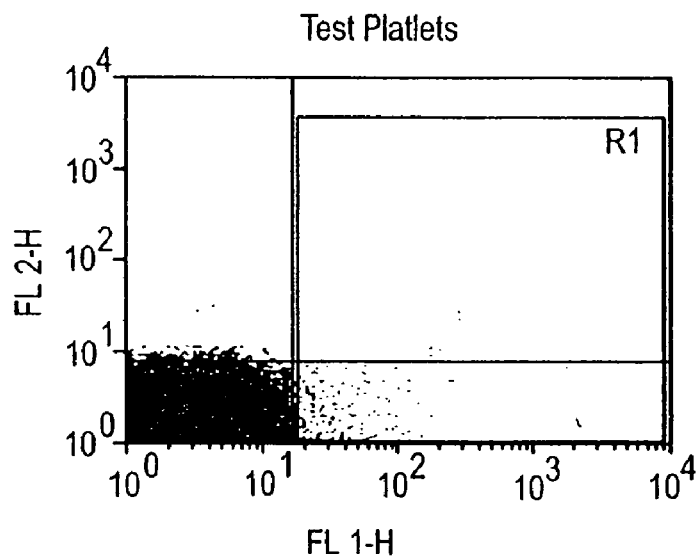
FIG. 23A is a scatter plot from a flow cytometry measurement of test platelets.
Figure 23B:
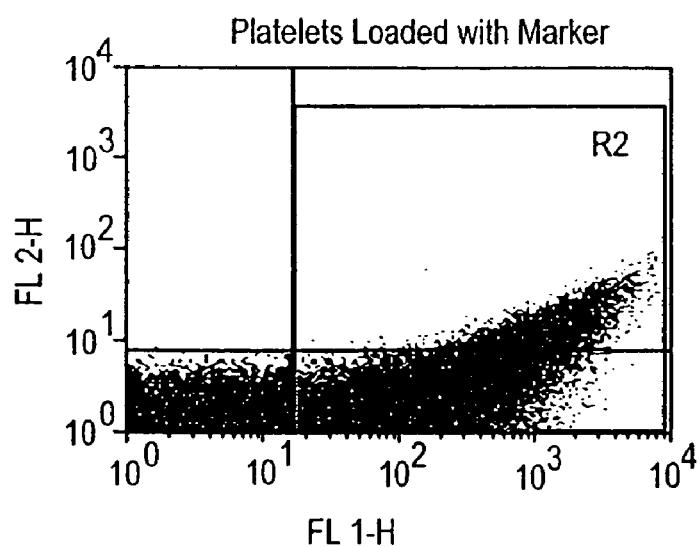
FIG. 23B is a scatter plot from a flow cytometry measurement of platelets loaded with a maker.

FIGS. 23A and 23B show scatter plots from a flow cytometer. Control (FIG. 23A) was incubated in a dilute solution of the fluorescent dye, calcein, for approximately 1 hour. The test sample (FIG. 23B) was suspended in the same dye solution, but was run through the electroporation device. Similar results were obtained using fluoresceinated albumin.

EXAMPLE 9

Platelets were treated in accordance with the present invention in the presence of a marker dye, calcein, then stimulated with increasing doses of collagen, a physiologic stimulant for platelets. This study demonstrated that the platelets retain biologic function, as demonstrated by the secretion of beta-thromboglobulin, a protein contained within platelets that is normally released upon activation. The detection of any level of activity indicates that the platelets are viable after the processing. On the other hand, the platelets do not release the molecular marker (calcein) that was loaded into them. This indicates that platelets loaded with a therapeutic agent would not prematurely release their "cargo", but would retain it until the loaded platelet adhered to a biologically active site and underwent degradation over a period of days (which is the expected behavior for platelets).

These experiments indicate that the loaded material is in the cell cytosol and not in the granules. Observation of platelets, loaded with the dye alexa, by confocal microscopy confirms that the dye is located diffusely within the platelet and is not simply adherent to the membrane.

Figure 24A:
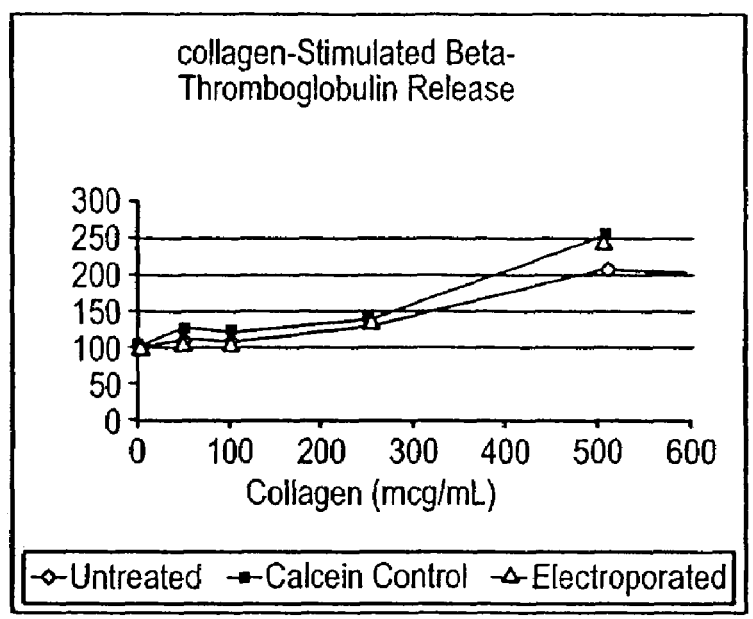
FIG. 24A is a graph showing collagen-stimulated beta-Thromboglobulin release of flow electroporated platelets as compared to controls.
Figure 24B:
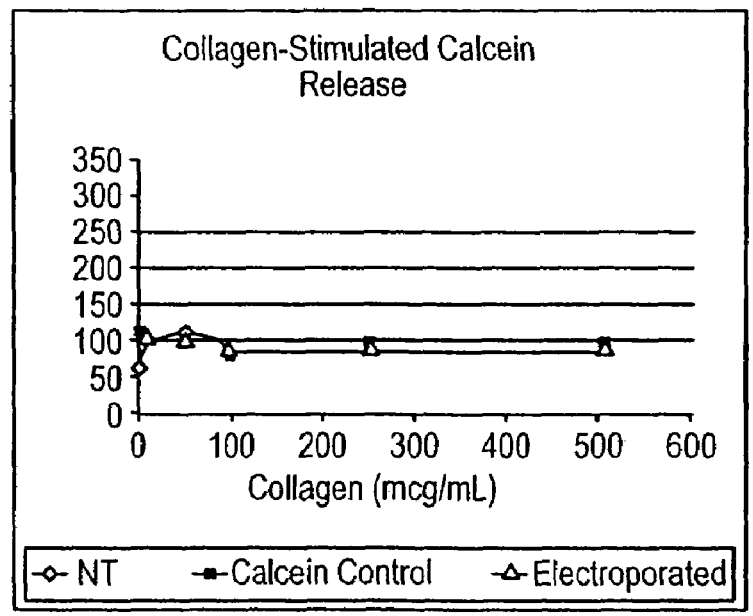
FIG. 24B is a graph showing collagen-stimulated Calcein release of flow electroporated platelets as compared to controls.

FIGS. 24A and 24B show platelets that had been washed but otherwise not treated (Untreated[N]}), platelets that were incubated with the fluorescent marker calcein (calcein control) and platelets electroporated with calcein (electroporated) were subsequently stimulated with the physiologic stimulus, collagen. As seen in FIG. 24A, samples responded similarly to a collagen stimulus by releasing beta-thromboglobulin, a natural constituent of platelets. As seen in FIG. 24B, platelets did not release the dye when stimulated.

EXAMPLE 10

Studies were performed with human platelets in a rabbit model, in which the animals were pre-treated with an agent that blocked macrophage activity. Platelets loaded with calcein or albumin circulate, but with a half-life less than that of untreated control platelets (Control 8 hours, test 2.5–3 hours). These studies show that platelets clearly have a finite circulation.

EXAMPLE 11

In another series of studies, platelets loaded with calcein were infused into the rabbits and major organs harvested within 1 half-life. Platelets were found in multiple organs—heart, intestine, muscle kidneys, liver and spleen. These studies demonstrate that platelets distribute to heart, kidneys, gut, etc., and are not simply sequestered in liver and spleen, as is the case with liposomes.

EXAMPLE 12

Figure 25:
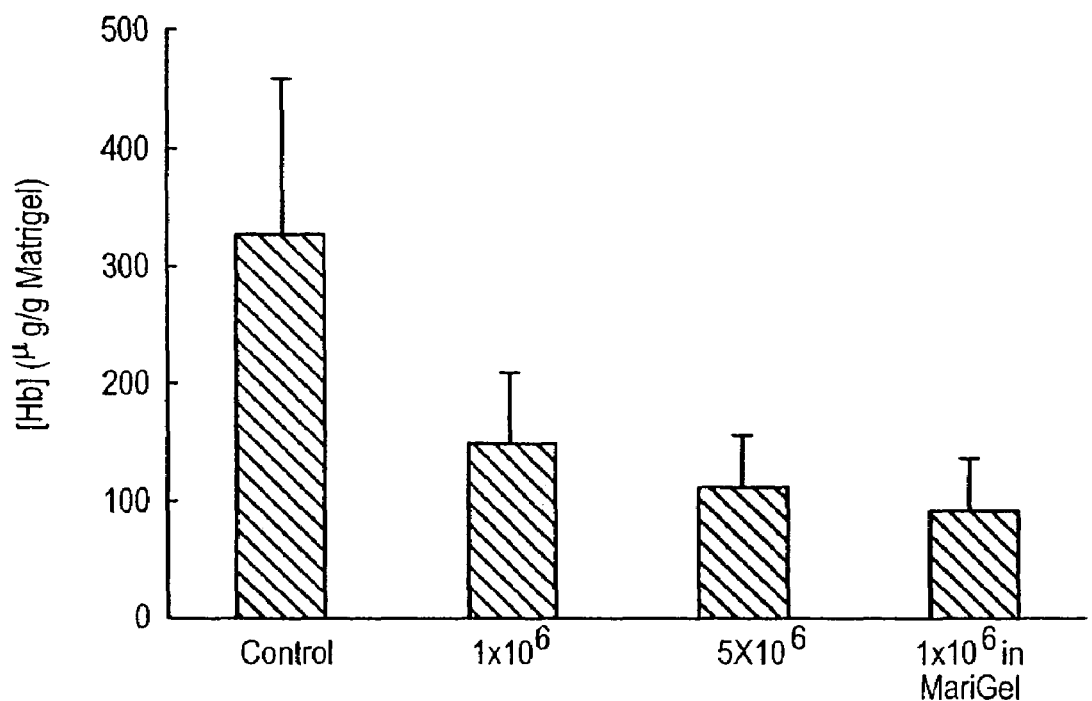
FIG. 25 is a graph showing in vivo delivery of mIL-12 by cells transfected with IL-12 gene.

Mouse cells transfected with an expression plasmid carrying the gene for the cytokine IL-12 were evaluated for the ability of these transfected cells to produce IL-12 after injection into a mouse. Since IL-12 is known to inhibit angiogenesis by up-regulating IFN alpha and IP-10 angiogenesis was measured using MatriGel. Mouse embryonic fibroblast 10T1/2 cells were transfected with a DNA plasmid encoding mIL-12 and injected subcutaneously into C3H mice. Human recombinant bFGF was mixed with MatriGel and subcutaneously injected at a remote site from the one of transfected cells injection. In one group of mice, the transfected cells were mixed together with bFGF and MatriGel. The amount of hemoglobin in MatriGel was measured 6 days post injection, as an indicator of angiogenesis. Data (FIG. 25) showed that mIL-12 transfected cells inhibited angiogenesis more than 70%. The transfected cells secreted about 72 ng of mIL-12 ($1 \times 10^6$ cells in 24 hrs). Systemic mIL-12 level was elevated among mice received mIL-12 transfected cells injection. No cytotoxic effect was observed. These results suggest that the MaxCyte system-mediated high-flow transfected cells are viable and express functional gene product in vitro & in vivo.

Figure 26:
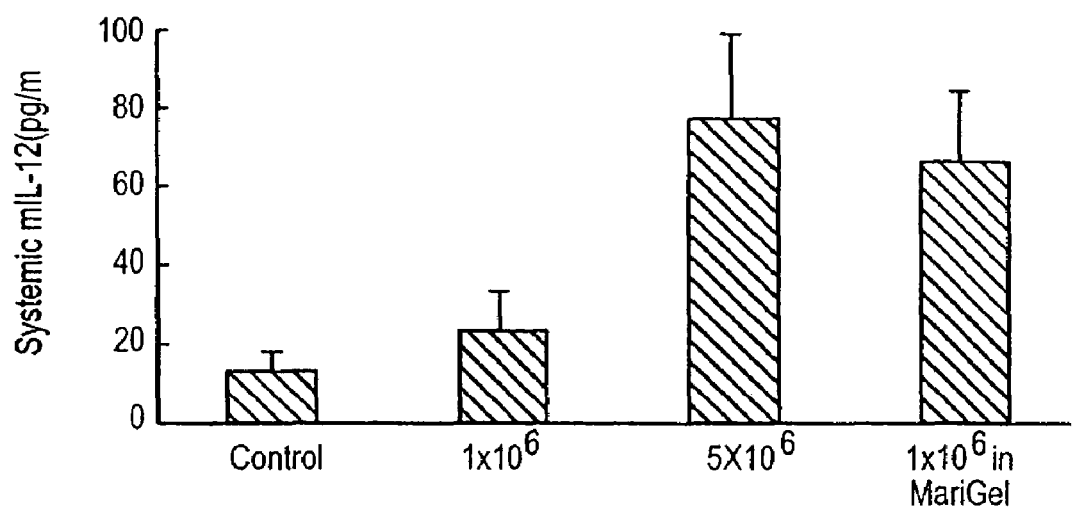
FIG. 26 is a graph showing inhibition of angiogenesis in implanted Matrigel by cells transfected with IL-12 gene.

Three hours post-transfection, mIL-12 modified mouse embryonic 10T1/2 cells were subcutaneously injected into C3H mice. Matrigel with 1 µg/mL bFGF was subcutaneously injected into dorsal thorax area, mixed or not mixed with cells. Control represents mice injected with non-transfected cells. Cells were injected on ventral side close to the thigh. ELISA analysis (R&D System) revealed up to 80–100 pg/mL of mIL-12 in treated mice plasma 2 days post-injection.

mIL-12 transfected mouse embryonic fibroblast blocked bFGF induced angiogenesis (FIG. 26). The MatriGel plugs were removed from the mice described in the previous figure, and homogenized in 1 ml of PBS. The hemoglobin amount was analyzed by absorption at 415 nm. Local delivery of mIL-12 transfected cells (in MatriGel) resulted in 70% of inhibition of angiogenesis.

EXAMPLE 13

Jurkat cells were resuspended in electroporation medium together with 0.5 mg/mL FITC-Dextran (500 kD MW). Then, the cells-Dextran mixture were flow electroporated in accordance with the present invention at 1.2 kV/cm, 400 µs pulse width at time intervals of 2.3 sec. The flow rate was 0.1 ml/sec. Three hours post-electroporation, FITC staining of cells was measured using flow cytometry to estimate the loading efficiency of cells by electroporation (Dex, +EP Propidium iodine exclusion was used to measure cell viability post electroporation). The reported results were the mean of three independent experiments. The results are shown in Table 9 below.

TABLE 9

| Flow Electroporation-Mediated Uptake of FITC-Dex (500 kD) | | | |
|---|---|---|---|
| | −EP, −Dex | −EP, Dex | EP + Dex |
| Viability (%) | 95 | 92 ± 2 | 92 ± 1.4 |
| Fluorescent cells (%) | 0.1 | 35 ± 20 | 90 ± 1.4 |
| Mean Fluorescence Intensity | 6 | 76 ± 53 | 185 ± 22 |

The results of this example show that electroporation significantly increased the percentage of cells that take up FITC labeled Dextran and electroporation did not significantly adversely effect the viability of these cells.

EXAMPLE 14

Figure 33:
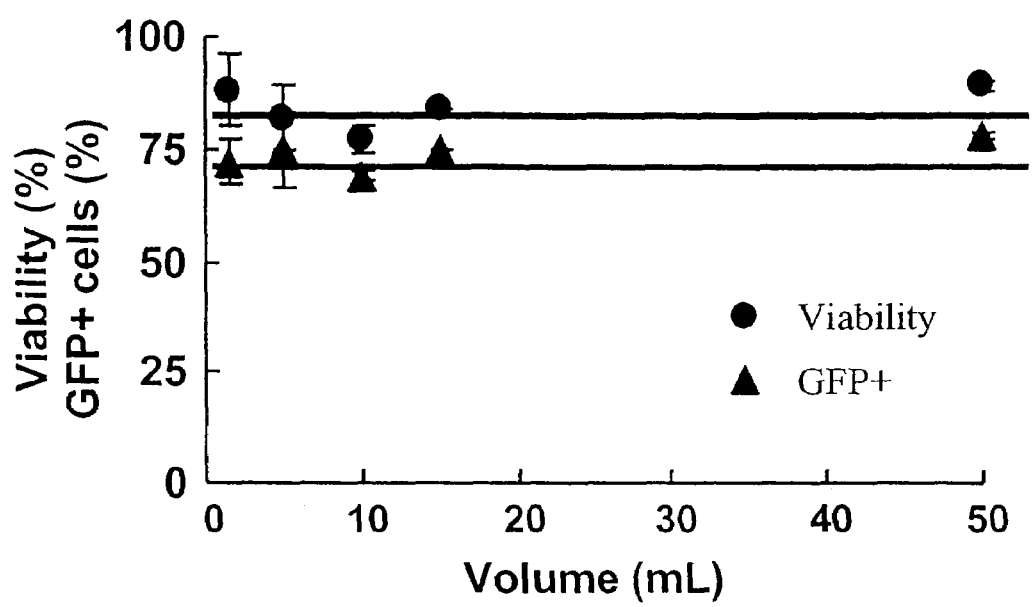
FIG. 33 is a graph showing estimated transfection efficiency and propidium iodine exclusion for cell viability.

Jurkat cells were electroporated with DNA plasmid encoding eGFP reporter under the transcriptional control of a CMV promoter at volumes of 1.5, 5, 10, 15, and 50 mL. Forty-eight hours post-electroporation, flow cytometric eGFP analysis was performed. Estimated transfection efficiency (solid triangle), and propidium iodine exclusion for cell viability (solid circle) are shown in FIG. 33. The results of this example show that the efficiency of transfection and viability did not significantly change during the flow electroporation process and that this process can be scaled up simply by passing more cells and DNA through the device and operating it for a longer time.

EXAMPLE 15

Figure 34:
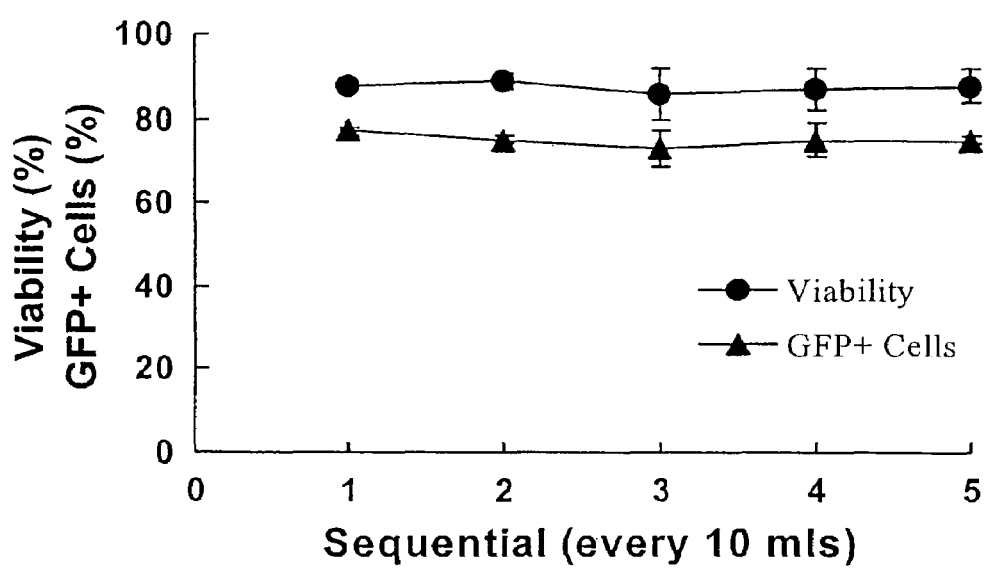
FIG. 34 is a graph showing efficiency of transfection and cell viability.

Jurkat cells ($1.2 \times 10^9$) were resuspended in 50 mL of B&K pulsing buffer with 80 µg/mL of DNA plasmid encoding eGFP reporter gene. The cells were electroporated using a flow cell in accordance with the present invention. The transfected samples were collected every 10 mL, and cultured in complete medium. Transfection efficiency and cell viability were analyzed at 40 hours post-electroporation. The results of this example are shown in FIG. 34. The results of this example show that the efficiency of transfection and the viability did not significantly change during the flow electroporation process and that this process can be scaled up simply by passing more cells and DNA thought the device and operating it for a longer time.

EXAMPLE 16

Figure 35:
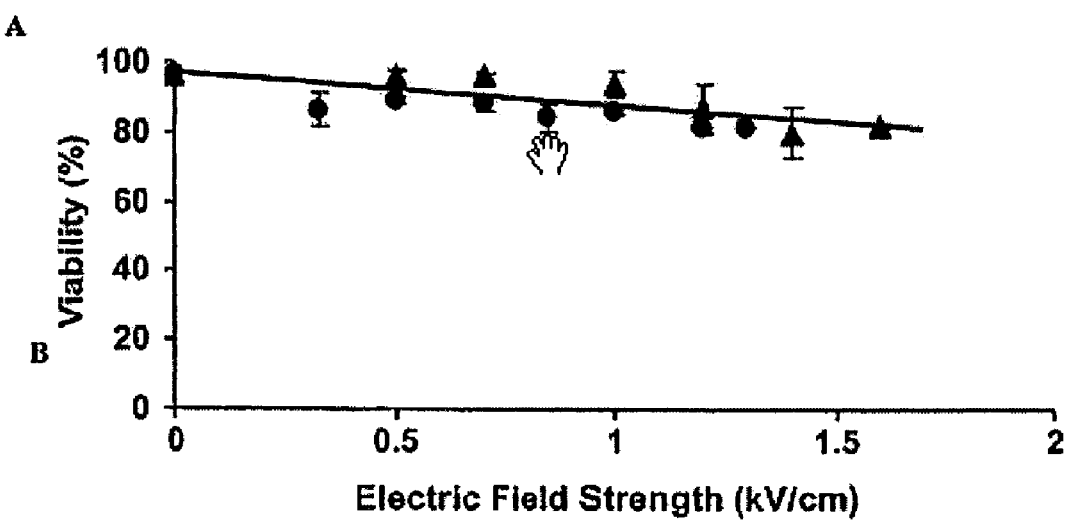
FIG. 35 is a graph showing cell viability versus electric field strength.
Figure 36:
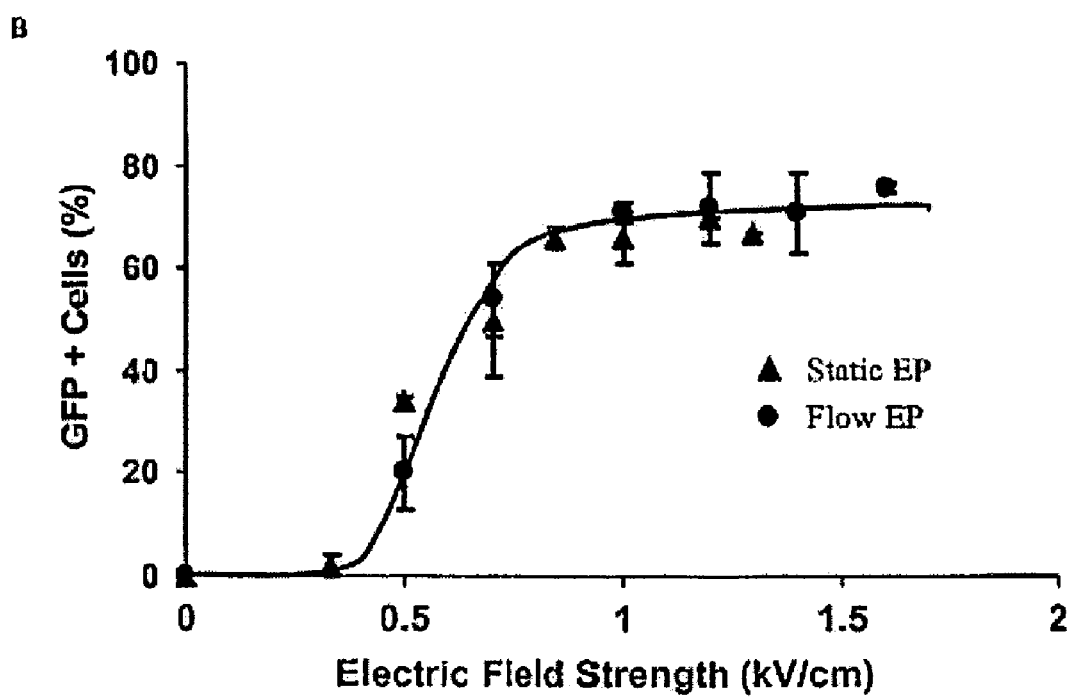
FIG. 36 is a graph showing propidium iodine exclusion for cell viability.

A comparison of transfection efficiency and cell viability between static and flow electroporation was performed. Jurkat cells were electroporated with DNA plasmid encoding eGFP either in a static (5) or flow (=) mode. Various electric field strengths were applied to the electrodes ranged from 0.4 to 1.7 kV/mL. Forty-eight hours post-electroporation, flow cytometric analysis for eGFP was performed. Estimated transfection efficiency is shown in FIG. 35, and propidium iodine exclusion for cell viability is shown in FIG. 36. The results of this example show that transfection efficiency increased and plateaued with higher electric field strength. Cell viability was maintained at greater than 80% even at high electric field strengths.

EXAMPLE 17

Figure 37:
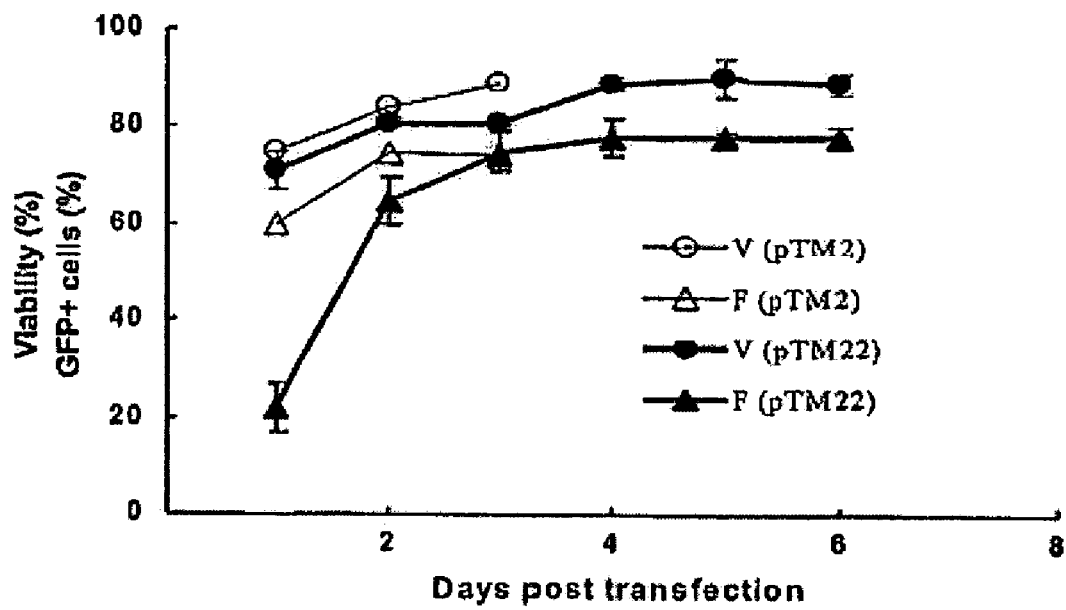
FIG. 37 is a graph showing efficiency of transfection and cell viability.
Figure 38:
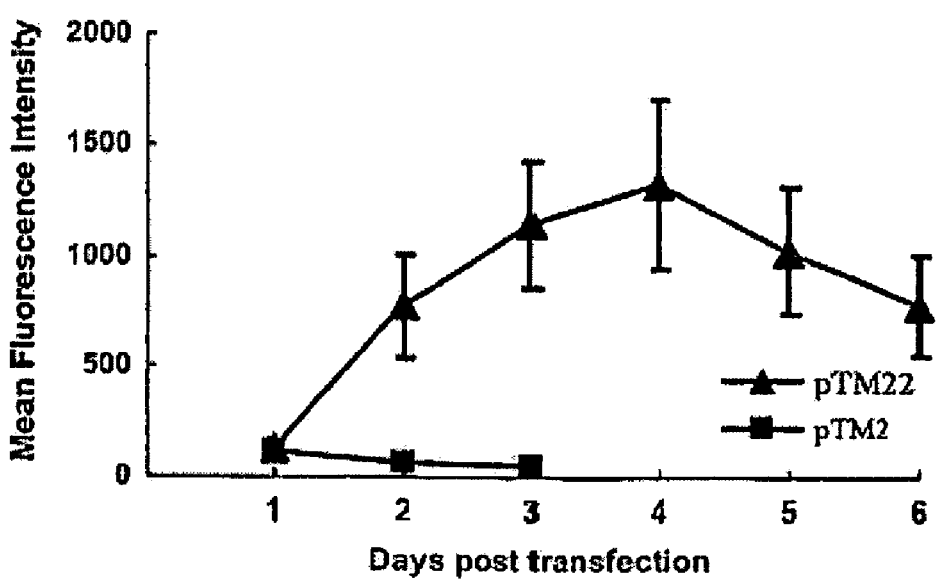
FIG. 38 is a graph showing mean fluorescence intensity versus days post-transfection.

Jurkat cells were flow electroporated in accordance with the present invention under the same condition with either a standard plasmid (pTM2, CMV-eGFP), or a plasmid containing EBNA1-OriP region (pTM22) from EBV virus. The transfected cells were analyzed by flow cytometry for transfection efficiency, viability and transgene expression level. Transfection efficiency and viability are shown in FIG. 37; mean fluorescence intensity is shown in FIG. 38. The results of this example show that DNA plasmid containing EBNA1 resulted in higher and longer term transgene expression. Expression level of the EBNA1 containing plasmid was over 500 fold higher than that of standard plasmid.

EXAMPLE 18

Various mammalian cells were flow electroporated under the same condition as described in Example 14 above, except 1.6 kV/cm and 1.2 kV/cm was used for 10T1/2 and Huh-7 cells, respectively. The results of this test are shown in Table 10 below.

TABLE 10

Flow Electroporation-mediated Transfection of Various Mammalian Cells

| Cell Type | Viability | Efficiency (eGFP+) | Mean Fluorescence Intensity |
|---|---|---|---|
| Jurkat (10 mls) | 77 ± 7 | 69 ± 1 | 163 ± 49 |
| Huh-7 (10 mls) | 94 ± 3 | 63 ± 15 | 930 ± 380 |
| 10T1/2 (1.5 mls) | 97 | 75 | 605 |

The result of this example show that a number of different cell lines can be efficiently electroporated using flow electroporation.

EXAMPLE 19

Figure 39:
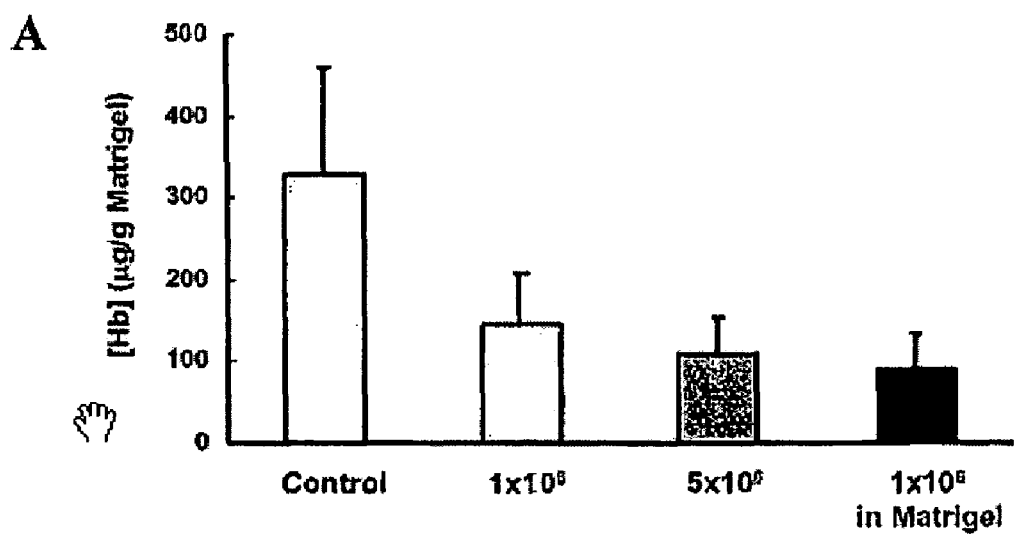
FIG. 39 is a graph showing levels of deoxygenated hemoglobin in various test samples.
Figure 40:
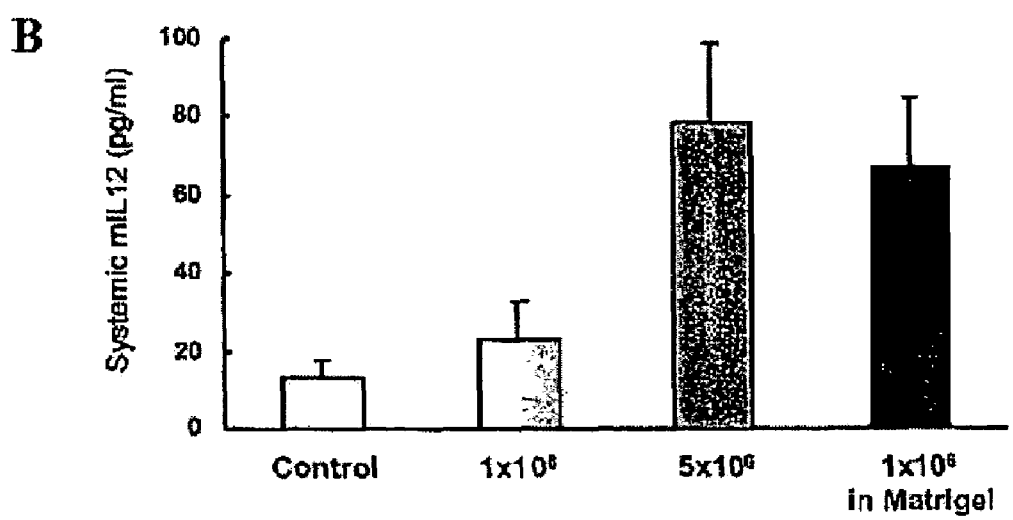
FIG. 40 is a graph showing levels of mIL12 in the plasma of various test mice.

Mouse embryonic 10T1/2 cells electroporated with a plasmid carrying the gene for mouse IL-12 were subcutaneously injected into C3H mice 3 hours post-transfection. Matrigel containing 1 mg/mL bFGF was subcutaneously injected into dorsal thorax area of mice that had been injected with the above-transfected cells and untransfected cells (negative control mice). Cells were injected on the ventral side close to the thigh. ELISA analysis (R&D System) revealed 80–100 pg/mL of mIL-12 in the plasma of the mice that received transfected cells 2 days post-injection (FIGS. 39 and 40). The MatriGel plugs were removed from the mice and homogenized in 1 mL of PBS. The hemoglobin present in the removed MatriGel was analyzed by absorption at 415 nm (FIG. 39). IL-12 level in plasma is shown in FIG. 40. Local delivery of mIL-12 transfected cells (in MatriGel) resulted in 70% of inhibition of angiogenesis compared to the mice that received untransfected cells.

EXAMPLE 20

Figure 41:
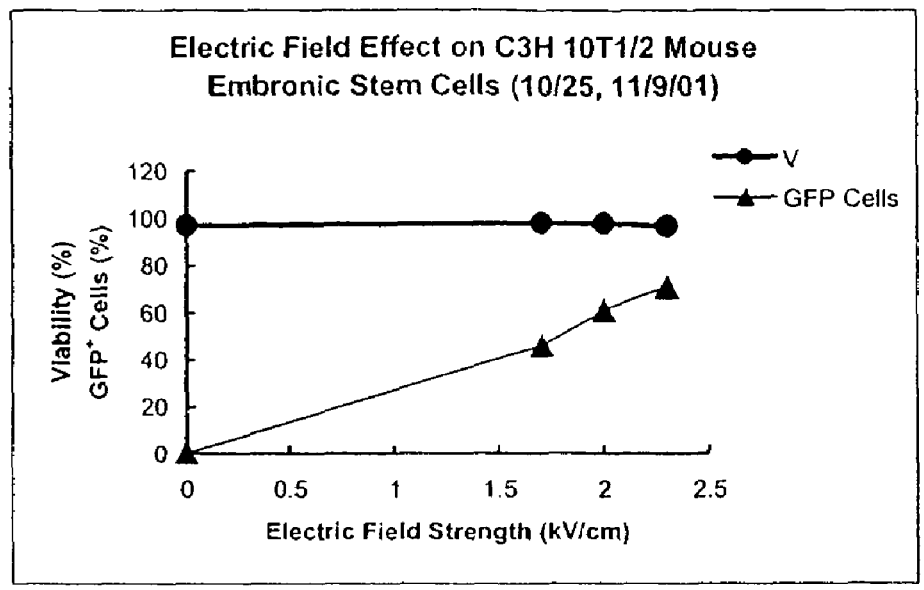
FIG. 41 is a graph showing the effect of electric field on electrotransfection of mouse embryonic stem cells.

The effect of electric field on electrotransfection of mouse embryonic stem cells was investigated in a static system. 10T1/2 cells were electroporated at various electric field strengths. Pulse width was 400 µs. Four pulses were provided to each sample in the presence of 60 µg/mL of DNA plasmid encoding for eGFP. The transfected cells were analyzed by flow cytometer for transfection efficiency and viability 1 day post-transfection. The results of this example are shown in FIG. 41. The results of this example show that efficient transfection of mouse embryonic stem cells occurs at field strengths greater than approximately 1.5 kV/cm.

EXAMPLE 21

Figure 42:
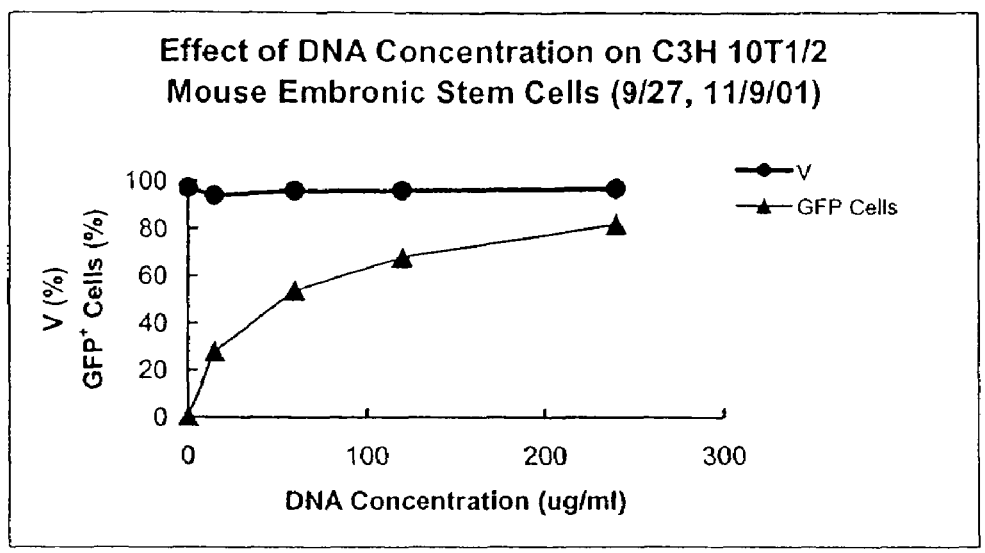
FIG. 42 is a graph showing the effect of DNA concentration on electrotransfection of mouse embryonic stem cell.

The effect of DNA concentration on electrotransfection of mouse embryonic stem cell under static conditions was investigated. 10T1/2 cells were electroporated at 2 kV/cm. Four pulses with 400 µs pulse width were provided to each sample in the presence of various concentrations of plasmid DNA encoding for eGFP. The transfected cells were analyzed by flow cytometer for transfection efficiency and viability 1 day post-transfection. The results of this example are shown in FIG. 42. The results of this example show that increasing the concentration of plasmid DNA increases the percentage of transfected cells, but that this effect diminishes with higher DNA concentrations.

EXAMPLE 22

Figure 43:
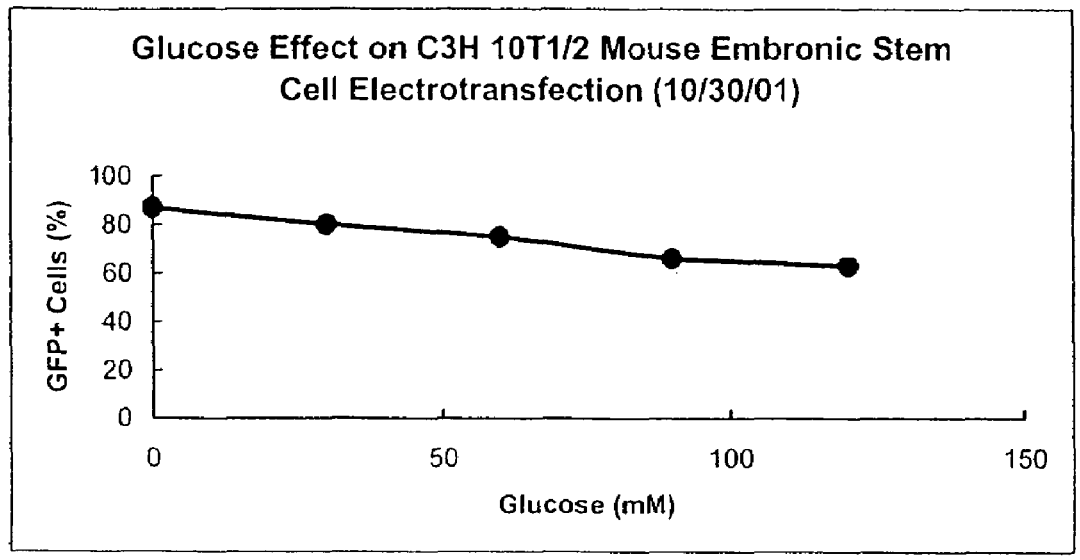
FIG. 43 is a graph showing the effect of glucose in the pulsing medium on electrotransfection of the 10T1/2 cells.
Figure 44:
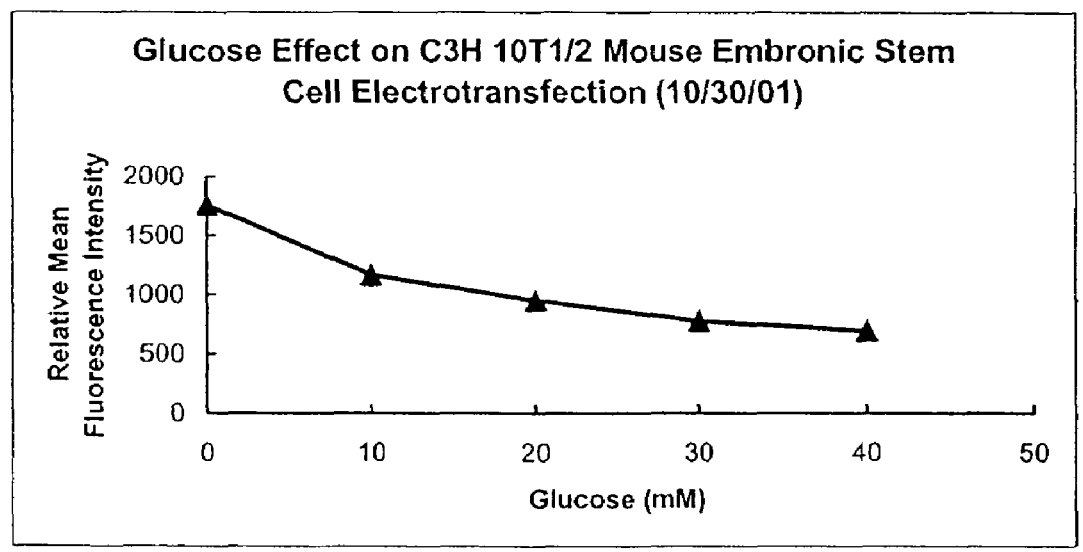
FIG. 44 is a graph showing the relative mean fluorescence intensity as a result of glucose in the pulsing medium used for electrotransfection of the 10T1/2 cells.

The effect of glucose in the pulsing medium on electrotransfection of the 10T1/2 cells was investigated. Pulsing buffer indicated was prepared by mixing B&K (125 mM KCl+15 mM NaCl+1.2 mM MgCl+25 mM Hepes, pH 7.4) and glucose medium (300 mM Glucose+1.2 mm Mg+15 mM NaCl+25 mM Hepes, pH 7.4). Cells were electroporated under static conditions at 2.3 kV/cm, with 400 µs pulse widths. Four pulses were provided to each sample in the presence of 60 µg/mL DNA plasmids coding for eGFP. Twenty-four hours post-transfection, the transfected cells were analyzed by flow cytometry. The results of this example show that higher glucose concentration decreased transfection efficiency (% of GFP cells (FIG. 43) and mean fluorescence of each GFP cell (FIG. 44).

EXAMPLE 23

Figure 45:
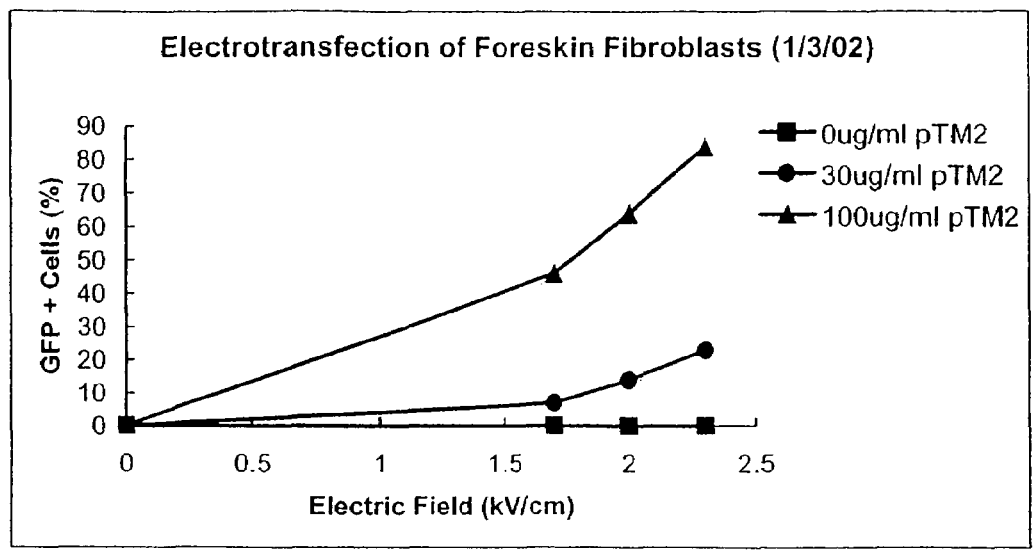
FIG. 45 is a graph showing the results of the electrotransfection of foreskin fibroblasts.

Electrotransfection of foreskin fibroblasts was investigated under static conditions. Foreskin fibroblasts were electroporated at various electric fields, as indicated in the graph (FIG. 45). Pulse widths of 400 µs were used. Four pulses were provided to each sample in the presence of two different DNA plasmid concentrations. Expression of reporter gene, eGFP, was analyzed at 15 hours post transfection. The results of this example are shown in FIG. 45. The results of this example show that efficient transfection of these cells occurs at field strengths greater than 1.5 kV/cm and that increasing concentration of plasmid DNA results in an increased percentage of transfected cells with no concomitant decrease in viability.

EXAMPLE 24

Figure 46:
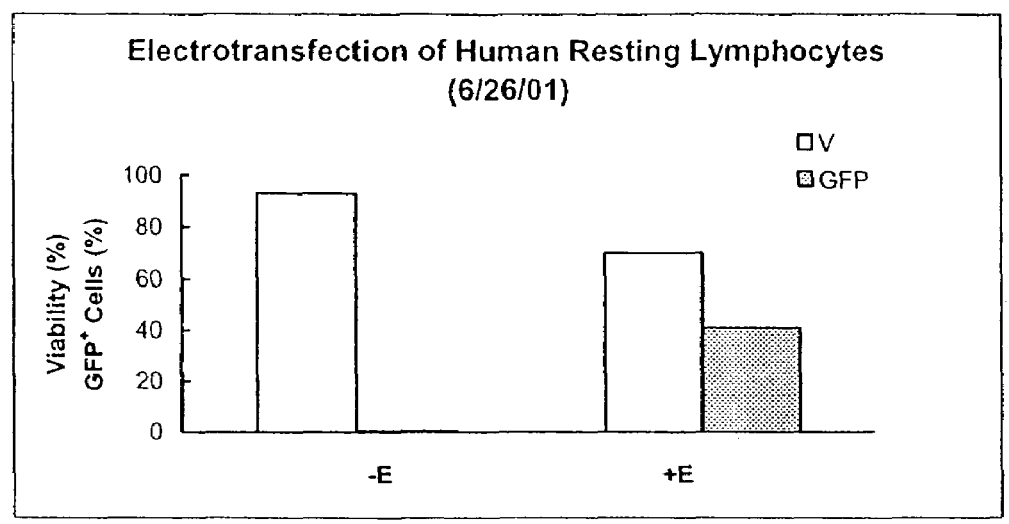
FIG. 46 is a graph showing efficiency of transfection and cell viability for human resting lymphocytes.

Resting human lymphocytes cells were transfected at 2.3 kV/cm with 400 µs pulse widths under static conditions. Four pulse were provided to each sample in the presence of 200 µg/mL DNA plasmid encoding for eGFP. Transfection efficiency was analyzed by flow cytometer 6 hours post-electroporation. The results of this example are shown in FIG. 46. Forty percent of the electroporated cells showed GFP positive; whereas, the cells without electroporation did not show any GFP fluorescence.

EXAMPLE 25

Figure 47:
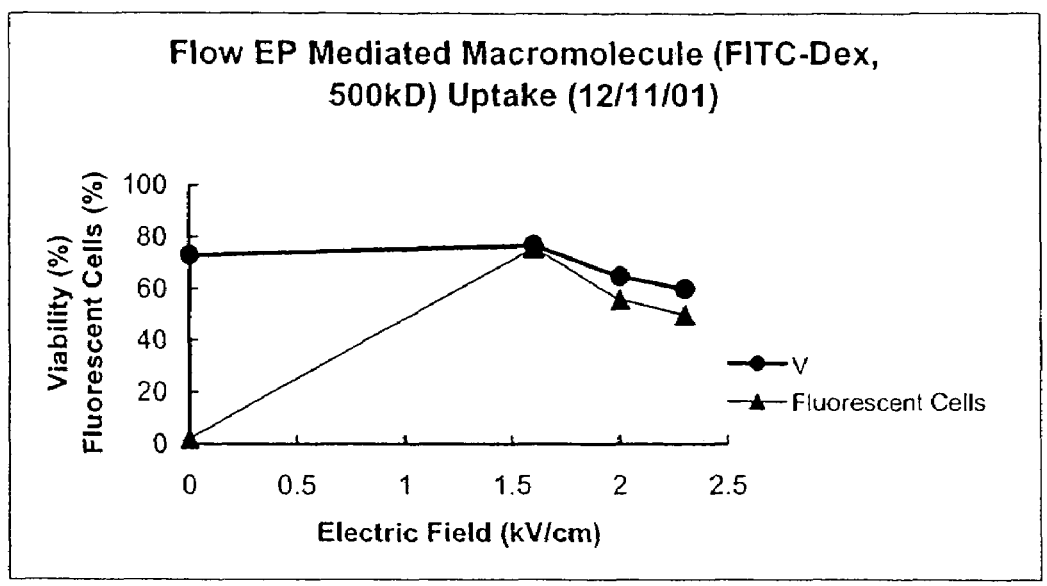
FIG. 47 is a graph showing the effect of electric field on flow electroporation mediated macromolecule uptake.

The effect of electric field on flow electroporation mediated macromolecule uptake was investigated. One na half mls of cells was flow electroporated at various field strengths using 1.6 ms pulse widths. Flow rate were set at 0.1 mL/sec and 5.5 sec. pulse intervals (1 pulse/cell during flow) with icy-water cooling were used. A mini-flow cell with an electrode gap of 4 mm was used. 100 µg/mL FITC-Dextran was presented during electroporation. Cells were analyzed 24 hours after electroporation. The results of this example are shown in FIG. 47. Use of an electric field strength of 1.5 kV/cm resulted in loading of a high percentage of cells and minimal loss of viability and using field strengths greater than 1.5 kV/cm reduced loading and viability but not substantially up to a field strength of 2.5 kV/cm.

EXAMPLE 26

Figure 48:
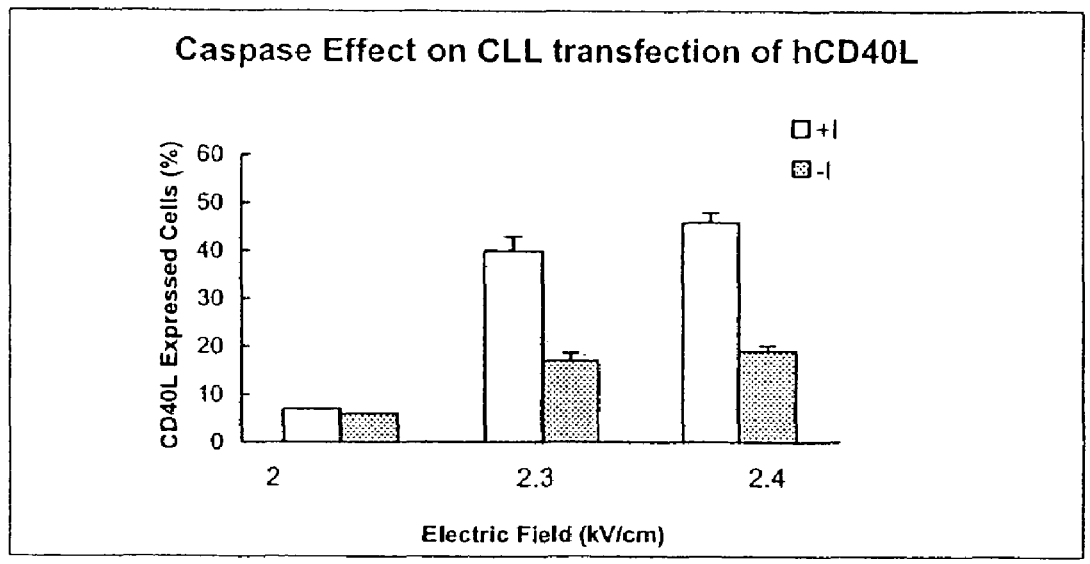
FIG. 48 is a graph showing hCD40L expression versus electric field strength.
Figure 49:
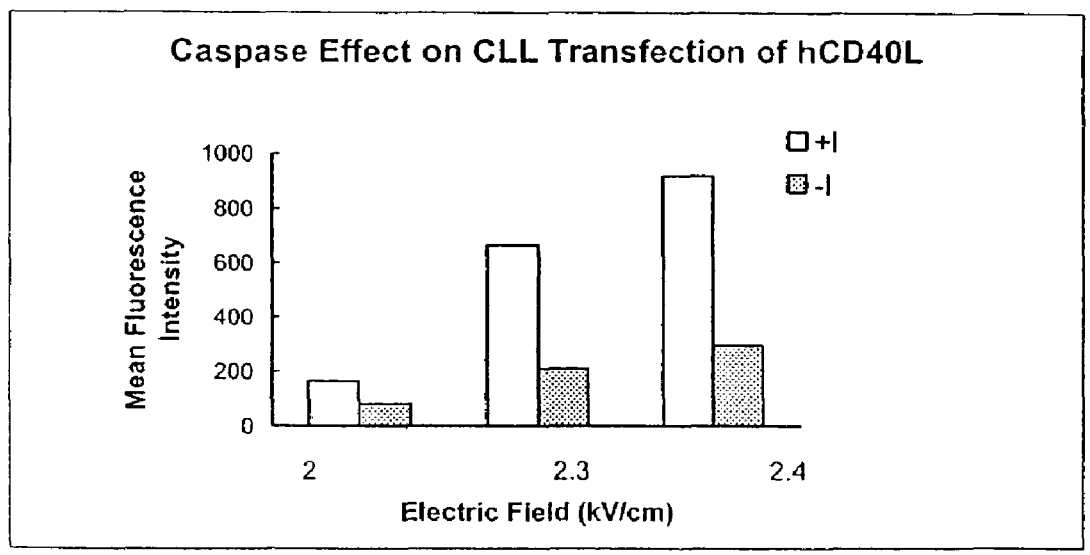
FIG. 49 is a graph showing mean fluorescence intensity versus electric field strength.

Caspase inhibitor effect on human CD40L transfection of CLL-B cells was investigated. CLL-B cells ($1.4 \times 10^8$ cells/mL) were electroporated by four 400 µs pulses at indicated electric fields in the present of DNA plasmid (200 µg/mL) coding for hCD40L. Following a 20 minute incubation at 37° C., cells were cultured in medium either with (+I) or without (−I) caspase inhibitor (Boc-Asp-FMK, 100 µM). hCD40L expression was analyzed 24 hour post transfection by flow cytometry with antibodies against hCD40L conjugate-labeled with Cychrome. The results of the example are shown in FIGS. 48 and 49. This example shows that caspase inhibitor improves hCD40L expression both the percentage of expressed cells (FIG. 48) and the expression level of hCD40L (FIG. 49).

EXAMPLE 27

Figure 50:
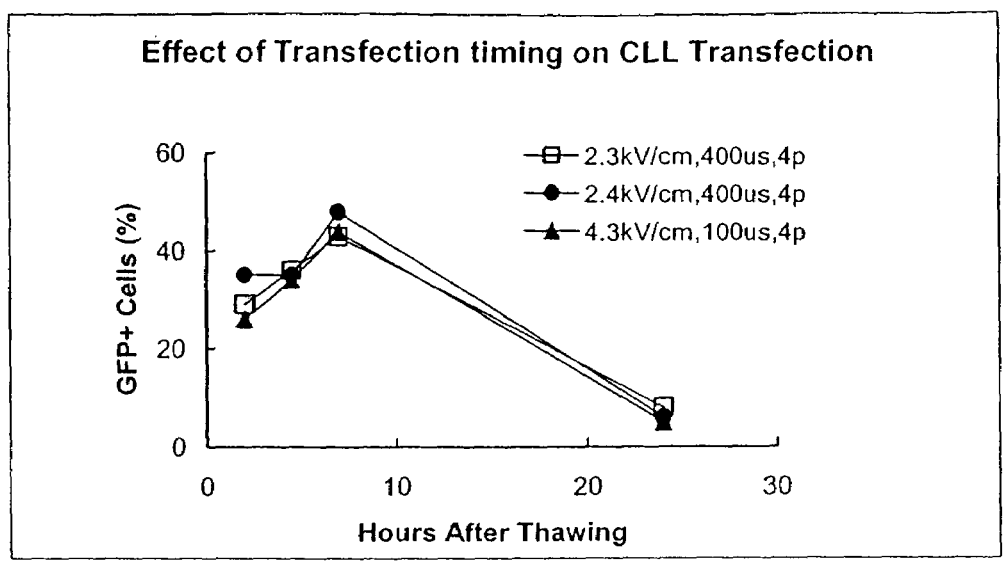
FIG. 50 is a graph showing the effect of electroporation timing on CLL cell transfection.

The effect of electroporation timing on CLL cell transfection was investigated. CLL cells ($2 \times 10^8$ cells/mL) were electroporated under static conditions with DNA plasmid encoding eGFP (200 µg/mL) at various times after thawing as indicated on the graph (FIG. 50). Transgene expression was analyzed with flow cytometer 24 hours post-transfection. The results of the example are shown in FIG. 50. The results of this example show that when cells were electroporated 24 hours after thawing, the transgene expression level dropped dramatically comparing to cells electroporated 6 h after thawing.

EXAMPLE 28

Figure 51:
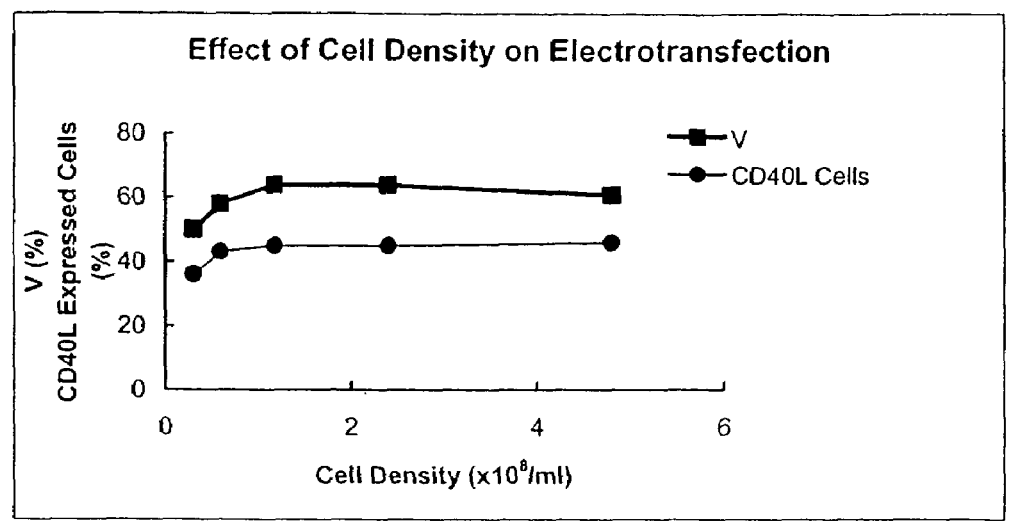
FIG. 51 is a graph showing the efficiency of transfection and cell viability.

The effect of cell density on electrotransfection under static conditions was investigated. CLL cells were pulsed at indicated cell density by four 400 µs pulses with 200 µg/mL plasmids coding for human CD40L. Cells were analyzed by flow cytometry with antibody against hCD40L conjugated with FITC 24 hours post-transfection. The results of the example are shown in FIG. 51. Cell density greater than $6 \times 10^7$ cells/mL up to $5 \times 10^8$ cells/mL resulted in the same level of hCD40L expression. However, cell viability and hCD40L expression levels were lower when the cell density was lower than $3 \times 10^7$ cells/mL.

EXAMPLE 29

Figure 52:
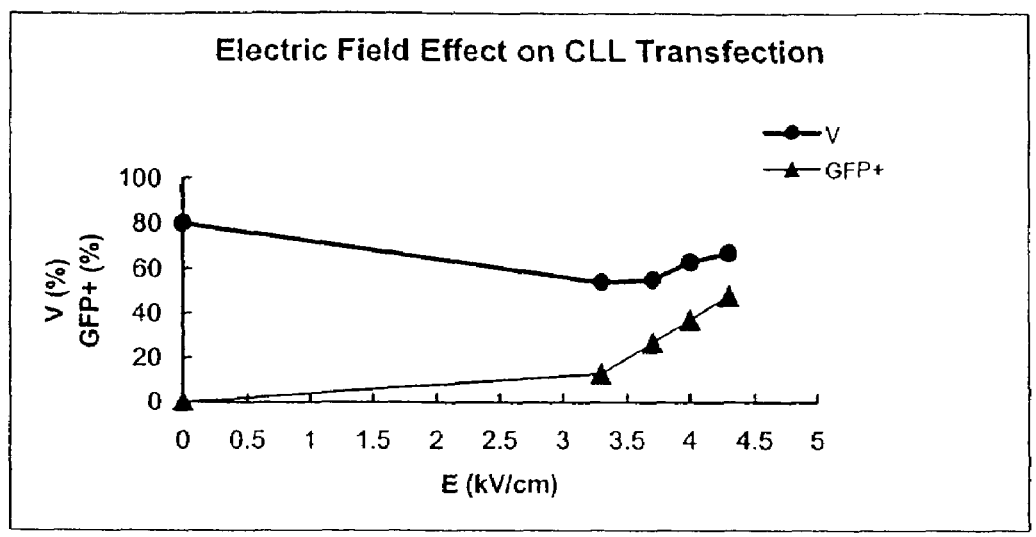
FIG. 52 is a graph showing the effect of electric field strength on CLL-B cell transfection.

The effect of electric field strength on CLL-B cell transfection under static conditions was investigated. CLL-B cells ($2 \times 10^8$ cells/mL) were pulsed at indicated electric field (FIG. 52) with four 100 µs pulses. Cells were analyzed with flow cytometry 14 hrs post transfection. The results of the example are shown in FIG. 52. In the electric field range of 3.3–4.3 kV/cm, cell viability does not change greatly (64%–75%). But the transfection efficiency in this electric field range increased from 10% to 45%.

EXAMPLE 30

Figure 53:
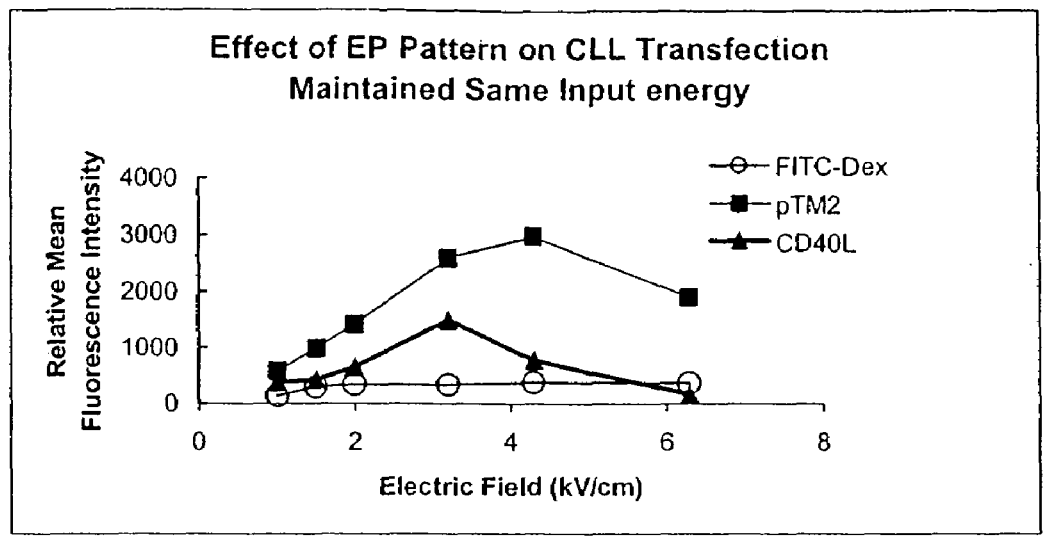
FIG. 53 is a graph showing relative mean fluorescence intensity versus electric field strength.
Figure 54:
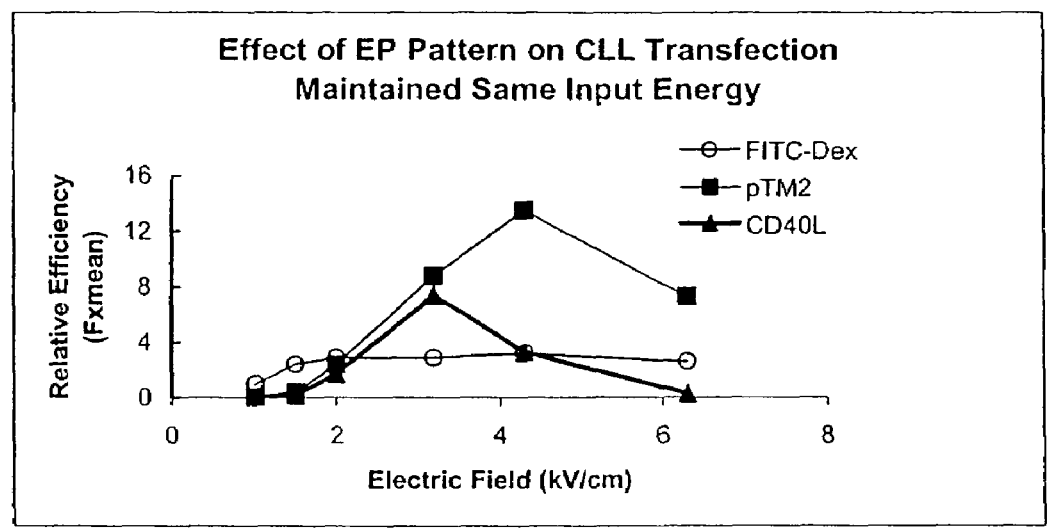
FIG. 54 is a graph showing cell loading efficiency.

The pulsing pattern effect on transfection of CLL-B cells under static conditions was investigated. CLL-B cells ($3 \times 10^8$ cells/mL) were pulsed at the same electric energy (1.3 J) with different electric field strengths and pulse durations in a MaxCyte cuvette with a 1.5 mm electrode gap. Following 17 hours of culture, cells were analyzed by flow cytometry. Pulsing conditions were four pulses with 1 kV/cm×1.6 ms, 1.5 kV/cm×800 µs, 2 kV/cm×400 µs, 3 kV/cm×200 µs, 4.3 kV/cm×100 µs and 6.3 kV/cm×50 µs, respectively with 200 µg/mL of DNA coding for eGFP and hCD40L for transgene expression or FITC-Dextran (500 kDalton) for macromolecule loading. The results of the example are shown in FIG. 53 and 54. The results of this example show that viability (FIG. 53) and FITC-Dextran loading (FIG. 54) does not depend greatly on pulsing conditions in all ranges indicated. However, the transgene expression peaked at around 3 kV/cm×200 µs and 4.3 kV/cm×100 µs as shown in FIG. 54 at this DNA concentration level.

EXAMPLE 31

Figure 55:
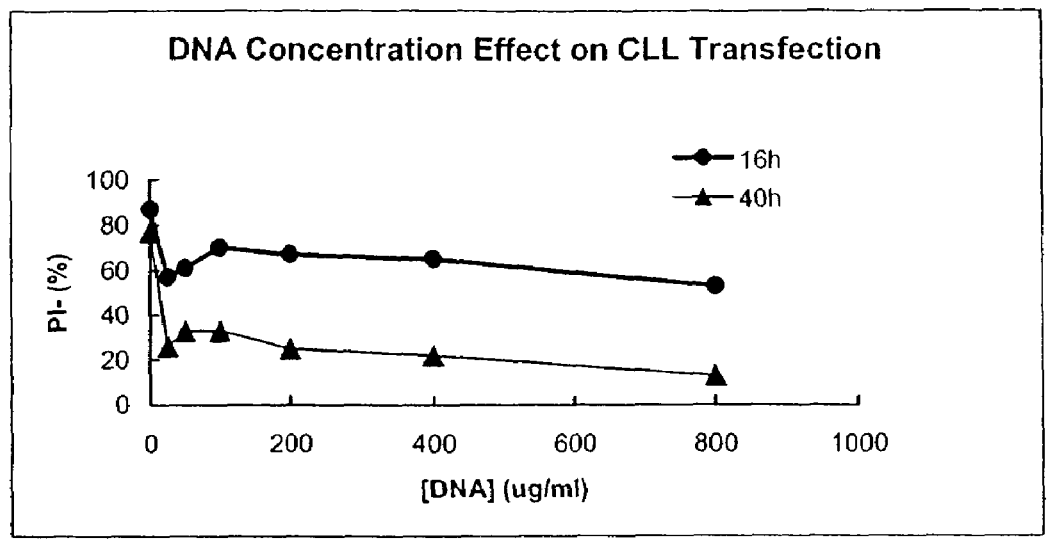
FIG. 55 is a graph showing cell DNA concentration effect on cell viability.
Figure 56:
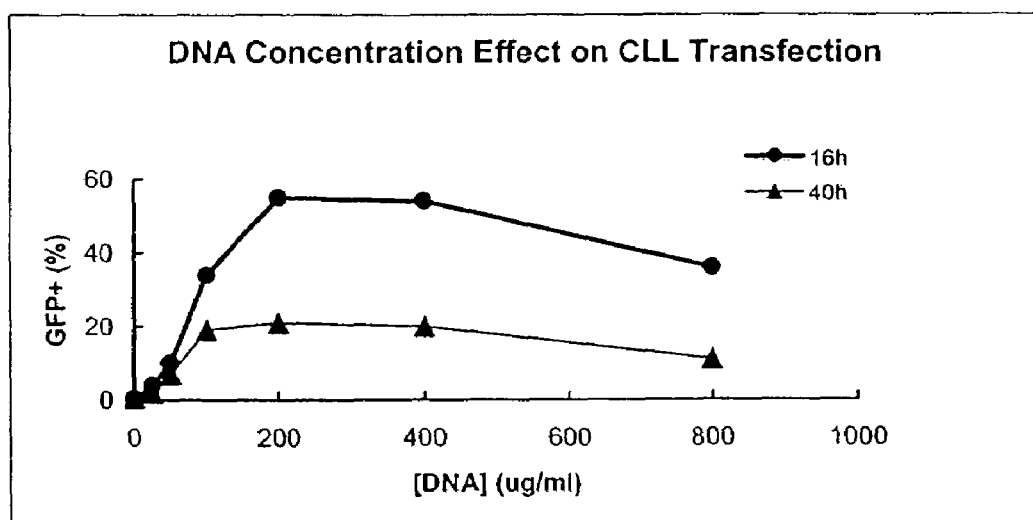
FIG. 56 is a graph showing DNA concentration effect on transfection efficiency.

The DNA concentration effect on transgene expression was investigated under static conditions. The CLL cells were analyzed by flow cytometry 16 hours and 40 hours post-pulsing. The results of this example are shown in FIG. 55 and 56. The results of this example show that cell viability did not significantly depend on DNA concentration when DNA concentration was >25 µg/mL. Cell viability decreased greatly with time. There was a >2 fold decrease in viability when analyzed at 40 hours comparing to at 16 hours (FIG. 55). Transfection efficiency increased from 0% to 56% when DNA concentration changes from 25 µg/mL to 200 µg/mL. DNA concentration higher than 200 µg/mL resulted in lower transfection efficiency.

EXAMPLE 32

Figure 57:
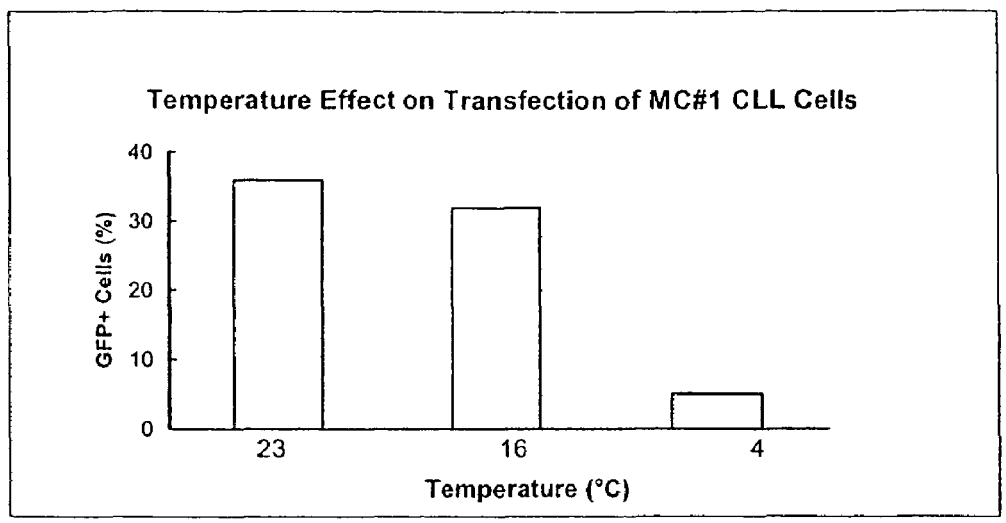
FIG. 57 is a graph showing the effect of temperature on transfection of CLL-B cells.

The effect of temperature on transfection of CLL-B cells was investigated under static conditions. CLL-B cells were electroporated with DNA plasmid (200 µg/mL) encoding for eGFP at the indicated temperatures (FIG. 57). Transfected cells were analyzed by flow cytometry 15 hours after pulsing. The results of this example are shown in FIG. 56. The results of this example show that transfection efficiency highly depended on pulsing temperature. Greater than seven-fold higher transfection efficiency was observed at 23° C. compared to 4° C. There was no significant difference on cell viability based on temperature (FIG. 57).

The terms and expressions which have been employed herein are used as terms of description and not of limitation, and there is no intention, in the use of such terms and expressions, of excluding any equivalents of the features shown and described or portions thereof. Having thus described the invention in detail, it should be apparent that various modifications may be made in the present invention without departing from the spirit and scope of the following claims.

We claim:

1. A flow electroporation device comprising:
   a chamber for containing a suspension of cells to be electroporated;
   the chamber being at least partially defined by opposing oppositely chargeable electrodes; and
   wherein the thermal resistance of the chamber is less than approximately 10° C. per Watt.

2. The flow electroporation device of claim 1, wherein the thermal resistance of the chamber is less than approximately 9.5° C. per Watt.

3. The flow electroporation device of claim 1, wherein the thermal resistance of the chamber is less than approximately 9° C. per Watt.

4. The flow electroporation device of claim 1, wherein the thermal resistance of the chamber is less than approximately 8.5° C. per Watt.

5. The flow electroporation device of claim 1, wherein the thermal resistance of the chamber is less than approximately 8° C. per Watt.

6. The flow electroporation device of claim 1, wherein the thermal resistance of the chamber is less than approximately 7.5° C. per Watt.

7. The flow electroporation device of claim 1, wherein the thermal resistance of the chamber is less than approximately 7° C. per Watt.

8. The flow electroporation device of claim 1, wherein the thermal resistance of the chamber is less than approximately 6.5° C. per Watt.

9. The flow electroporation device of claim 1, wherein the thermal resistance of the chamber is less than approximately 6° C. per Watt.

10. The flow electroporation device of claim 1, wherein the thermal resistance of the chamber is less than approximately 5.5° C. per Watt.

11. The flow electroporation device of claim 1, wherein the thermal resistance of the chamber is less than approximately 5° C. per Watt.

12. The flow electroporation device of claim 1, wherein the thermal resistance of the chamber is less than approximately 4.5° C. per Watt.

13. The flow electroporation device of claim 1, wherein the thermal resistance of the chamber is less than approximately 4° C. per Watt.

14. The flow electroporation device of claim 1, wherein the thermal resistance of the chamber is less than approximately 3.5° C. per Watt.

15. The flow electroporation device of claim 1, wherein the thermal resistance of the chamber is less than approximately 3° C. per Watt.

16. The flow electroporation device of claim 1, wherein the thermal resistance of the chamber is less than approximately 2.5° C. per Watt.

17. The flow electroporation device of claim 1, wherein the thermal resistance of the chamber is less than approximately 2° C. per Watt.

18. The flow electroporation device of claim 1, wherein the thermal resistance of the chamber is less than approximately 1.5° C. per Watt.

19. The flow electroporation device of claim 1, wherein the thermal resistance of the chamber is approximately 0.1° C. per Watt to 4° C. per Watt.

20. The flow electroporation device of claim 1, wherein the thermal resistance of the chamber is approximately 1.5° C. per Watt to 2.5° C. per Watt.

21. A method of electroporating a cell comprising flowing a suspension of cells to be electroporated through an electric field in a flow chamber, the electric field being produced by opposing oppositely charged electrodes at least partially defining the flow chamber, wherein the thermal resistance of the flow chamber is less than approximately 10° C. per Watt.

22. The method of claim 21, wherein the thermal resistance of the flow chamber is less than approximately 9.5° C. per Watt.

23. The method of claim 21, wherein the thermal resistance of the flow chamber is less than approximately 9° C. per Watt.

24. The method of claim 21, wherein the thermal resistance of the flow chamber is less than approximately 8.5° C. per Watt.

25. The method of claim 21, wherein the thermal resistance of the flow chamber is less than approximately 8° C. per Watt.

26. The method of claim 21, wherein the thermal resistance of the flow chamber is less than approximately 7.5° C. per Watt.

27. The method of claim 21, wherein the thermal resistance of the flow chamber is less than approximately 7° C. per Watt.

28. The method of claim 21, wherein the thermal resistance of the flow chamber is less than approximately 6.5° C. per Watt.

29. The method of claim 21, wherein the thermal resistance of the flow chamber is less than approximately 6° C. per Watt.

30. The method of claim 21, wherein the thermal resistance of the flow chamber is less than approximately 5.5° C. per Watt.

31. The method of claim 21, wherein the thermal resistance of the flow chamber is less than approximately 5° C. per Watt.

32. The method of claim 21, wherein the thermal resistance of the flow chamber is less than approximately 4.5° C. per Watt.

33. The method of claim 21, wherein the thermal resistance of the flow chamber is less than approximately 4° C. per Watt.

34. The method of claim 21, wherein the thermal resistance of the flow chamber is less than approximately 3.5° C. per Watt.

35. The method of claim 21, wherein the thermal resistance of the flow chamber is less than approximately 3° C. per Watt.

36. The method of claim 21, wherein the thermal resistance of the flow chamber is less than approximately 2.5° C. per Watt.

37. The method of claim 21, wherein the thermal resistance of the flow chamber is less than approximately 2° C. per Watt.

38. The method of claim 21, wherein the thermal resistance of the flow chamber is less than approximately 1.5° C. per Watt.

39. The method of claim 21, wherein the thermal resistance of the flow chamber is approximately 0.1° C. per Watt to 4° C. per Watt.

40. The method of claim 21, wherein the thermal resistance of the flow chamber is approximately 1.5° C. per Watt to 2.5° C. per Watt.

41. A flow electroporation device comprising:
walls defining a flow channel having an electroporation zone configured to receive and to transiently contain a continuous flow of a suspension of cells to be electroporated;
an inlet flow portal in fluid communication with the flow channel, whereby the suspension can be introduced into the flow channel through the inlet flow portal;
an outlet flow portal in fluid conmiunication with the flow channel, whereby the suspension can be withdrawn from the flow channel through the outlet portal;
the walls defining the flow channel within the electroporation zone comprising a first electrode forming a substantial portion of a first wall of the flow channel and a second electrode forming a substantial portion of a second wall of the flow channel opposite the first wall, the first and second electrodes being such that when placed in electrical communication with a source of electrical energy an electric field is formed therebetween through which the suspension can flow; and
wherein the thermal resistance of the flow channel is less than approximately 10° C. per Watt.

42. The device of claim 41, wherein the thermal resistance of the flow channel is less than approximately 4° C. per Watt.

43. The device of claim 41, wherein the thermal resistance of the flow chamber is approximately 0.1° C. per Watt to 4° C. per Watt.

44. The device of claim 41, wherein the thermal resistance of the flow chamber is approximately 1.5° C. per Watt to 2.5° C. per Watt.

45. The device of claim 41, wherein the first and second electrodes are spaced from each other at least 1 mm.

46. The device of claim 41, wherein the flow chamber has a ratio of combined electrode surface in contact with buffer to the distance between the electrodes of approximately 1 to 100 cm.

47. The device of claim 41, wherein the cells electroporated in the flow channel are not substantially thermally degraded thereby.

48. A flow electroporation device comprising:
a flow chamber for containing a suspension of cells to be electroporated;
the flow chamber being at least partially defined by opposing oppositely chargeable electrodes; and
wherein the flow chamber has a ratio of combined electrode surface in contact with buffer to the distance between the electrodes of approximately 1 to 100 cm.

49. The device of claim 48, wherein the ratio is approximately 1 to 90 cm.

50. The device of claim 48, wherein the ratio is approximately 1 to 80 cm.

51. The device of claim 48, wherein the ratio is approximately 1 to 70 cm.

52. The device of claim 48, wherein the ratio is approximately 1 to 60 cm.

53. The device of claim 48, wherein the ratio is approximately 1 to 50 cm.

54. A flow electroporation device comprising:
walls defining a flow channel configured to receive and to transiently contain a continuous flow of a suspension of cells to be electroporated;
an inlet flow portal in fluid communication with the flow channel, whereby the suspension can be introduced into the flow channel through the inlet flow portal;
an outlet flow portal in fluid communication with the flow channel, whereby the suspension can be withdrawn from the flow channel through the outlet portal;
the walls defining the flow channel comprising a first electrode forming at least a portion of a first wall of the flow channel and a second electrode forming at least a portion of a second wall of the flow channel opposite the first wall, the first and second electrodes being such that when placed in electrical communication with a source of electrical energy an electric field is formed therebetween through which the suspension can flow; and wherein the thermal resistance of the flow channel is less than approximately 10° C. per Watt.

55. The device of claim 54, wherein the thermal resistance of the flow channel is less than approximately 4° C. per Watt.

56. The device of claim 54, wherein the thermal resistance of the flow channel is approximately 0.1° C. per Watt to 10° C. per Watt.

57. The device of claim 54, wherein the thermal resistance of the flow channel is approximately 1.5° C. per Watt to 2.5° C. per Watt.

58. The device of claim 54, wherein the first and second electrodes are spaced from each other at least 1 mm.

59. The device of claim 54, wherein the first and second electrodes are spaced from each other at least 3 mm.

60. The device of claim 54, wherein the flow chamber has a ratio of combined electrode surface in contact with buffer to the distance between the electrodes of approximately 1 to 100 cm.

61. The device of claim 54, wherein the flow chamber has a ratio of combined electrode surface in contact with buffer to the distance between the electrodes of approximately 1 to 100 cm and wherein the first and second electrodes are spaced from each other at least 1 mm.

62. The device of claim 54, wherein the flow chamber has a ratio of combined electrode surface in contact with buffer to the distance between the electrodes of approximately 1 to 100 cm and wherein the first and second electrodes are spaced from each other at least 3 mm.

63. The device of claim 54, wherein the flow chamber has a ratio of combined electrode surface in contact with buffer to the distance between the electrodes of approximately 1 to 100 cm and wherein the first and second electrodes are spaced from each other approximately 3 mm to approximately 2 cm.

64. The device of claim 54, wherein the cells electroporated in the flow channel are not substantially thermally degraded thereby.

65. A flow electroporation device, comprising:
walls defining a flow channel configured to receive and to transiently contain a continuous flow of a suspension comprising particles;
an inlet flow portal in fluid communication with the flow channel, whereby the suspension can be introduced into the flow channel through the inlet flow portal;
an outlet flow portal in fluid communication with the flow channel, whereby the suspension can be withdrawn from the flow channel through the outlet flow portal;
the walls defining the flow channel comprising a first electrode plate forming a first wall of the flow channel and a second electrode plate forming a second wall of the flow channel opposite the first wall; wherein the area of the electrodes contact with the suspension, and the distance between the electrodes is chosen so that the thermal resistance of the flow channel is less than approximately 4° C. per Watt;
the paired electrodes placed in electrical communication with a source of electrical energy, whereby an electrical field is formed between the electrodes;
whereby the suspension of the particles flowing through the flow channel can be subjected to an electrical field formed between the electrodes.

66. The flow electroporation device of claim 65, wherein the electrode plates defining the flow channel further comprises: a gasket formed from an electrically non-conductive material and disposed between the first and second electrode plates to maintain the electrode plates in spaced-apart relation, the gasket defining a channel therein forming opposed side walls of the flow channel.

67. The flow electroporation device of claim 65, wherein the gasket forms a seal with each of the first and second electrode plates.

68. The flow electroporation device of claim 65, wherein the device comprises a plurality of flow channels, and wherein the gasket comprises a plurality of channels forming opposed side walls of each of the plurality of channels.

69. The flow electroporation device of claim 65, wherein one of the inlet flow portal and the outlet flow portal comprises a bore formed in one of the electrode plates and in fluid communication with the flow channel.

70. The flow electroporation device of claim 65, wherein the other of the inlet flow portal and the outlet flow portal comprises a bore formed in the one of the electrode plates and in fluid communication with the flow channel.

71. The flow electroporation device of claim 65, wherein the other of the inlet flow portal and the outlet flow portal comprises a bore formed in the other of the electrode plates and in fluid communication with the flow channel.

72. The flow electroporation device of claim 65, further comprising a cooling element operatively associated with the flow channel to dissipate heat.

73. The flow electroporation device of claim 65, wherein the cooling element comprises a thermoelectric cooling element.

74. The flow electroporation device of claim 65, wherein the cooling element comprises a cooling fluid flowing in contact with the electrode.

75. The flow electroporation device of claim 65, wherein the cooling element comprises a heat sink operatively associated with the electrode.

76. The flow electroporation device of claim 65, wherein the heat resistance of the flow channel is less than approximately 3° C. per watt.

77. The flow electroporation device of claim 65, wherein the heat resistance of the flow channel is less than approximately 2° C. per watt.

78. The flow electroporation device of claim 65, wherein the heat resistance of the flow channel is between approximately 0.5° C. per Watt and 4° C. per Watt.

79. The flow electroporation device of claim 65, wherein the heat resistance of the flow channel is between approximately 1° C. per Watt and 3° C. per Watt.

80. The flow electroporation device of claim 65, wherein the heat resistance of the flow channel is between approximately 1.5° C. and 2.5° C.

81. The flow electroporation device of claim 65, wherein the first electrode comprises an elongated, electrically conductive structure,
wherein the second electrode comprises a tubular, electrically conductive structure;
wherein the electrodes are concentrically arranged such that the second, tubular electrode surrounds the first electrode in spaced-apart relation thereto; and
wherein the flow channel is disposed within an annular space defined between the first and second electrodes.

82. The flow electroporation device of claim 81, wherein the electrodes form at least a portion of the walls defining the flow channel.

83. The flow electroporation device of claim 81, further comprising concentric annular spacers for maintaining the first and second electrodes in spaced-apart, concentric relation.

84. The flow electroporation device of claim 81, wherein the device is arranged in series with a second, like device.

85. The flow electroporation device of claim 81, wherein the device is arranged in parallel with a second, like device.

86. A method of transfecting a cell comprising providing a nucleic acid or an expression vector coding for a desired protein or peptide and introducing the expression vector into the cell by flow electroporation using a flow channel having a thermal resistance of less than approximately 10° C. per Watt.

87. The method of claim 86, wherein the thermal resistance of the flow channel is less than approximately 4° C. per Watt.

88. The method of claim 86, wherein the thermal resistance of the flow channel is approximately 0.1° C. per Watt to 4° C. per Watt.

89. The method of claim 86, wherein the thermal resistance of the flow channel is approximately 1.5° C. per Watt to 2.5° C per Watt.

90. The method of claim 86 wherein greater than 50% of the cells transfected by electroporation express the desired protein or peptide.

91. The method of claim 86 wherein approximately 50% to 95% of the cells transfected by electroporation express the desired protein or peptide.

92. The method of claim 86, wherein approximately 60% to 90% of the cells transfected by electroporation express the desired protein or peptide.

93. The method of claim 86, wherein approximately 70% to 80% of the cells transfected by flow electroporation express the desired protein or peptide.

94. The method of claim 86, wherein the cells transfected by flow electroporation are greater than approximately 50% viable.

95. The method of claim 86, wherein the cells transfected by flow electroporation are greater than approximately 60% viable.

96. The method of claim 86, wherein the cells transfected by flow electroporation are greater than approximately 70% viable.

97. The method of claim 86, wherein the cells transfected by flow electroporation are greater than approximately 80% viable.

98. The method of claim 86, wherein the cells transfected by flow electroporation are greater than approximately 90% viable.

99. The method of claim 86, wherein the cells transfected by flow electroporation are approximately 50% to 90% viable.

100. The method of claim 86, wherein the cells transfected by flow electroporation are approximately 60% to 90% viable.

101. The method of claim 86, wherein the cells transfected by flow electroporation are approximately 70% to 80% viable.

102. The method of claim 86, where the nucleic acid or desired protein is b-cell differentiation factor, b-cell growth factor, mitogenic cytokine, chemotactic cytokine, colony stimulating factor, angiogenesis factor, cadherin, selectin, inteegrin, NCAM, ICAM, L1, t-cell replacing factors, differentiation factor, transcription factor, mRNA, heat shock protein, nuclear protein complexe, RNA/DNA oligomer, IFN-alpha, IFN-beta, IFN-omega, IL1, IL2, IL3, IL4, IL5, IL6, IL7, IL8, IL9, IL10, IL11, IL12, IL13, IL14, IL15, IL16, IL17, IL18, leptin, myostatin, macrophage stimulating protein, platelet-derived growth factor, TNF-alpha, TNF-beta, NGF, CD40L, CD137L/4-1BBL, human lymphotoxin-beta, TNF-related apoptosis-inducing ligand, monoclonal antibody, fragments of monoclonal antibody, G-CSF, M-CSF, GM-CSF, PDGF, IL1-alpha, IL1-beta, FGF IFN-gamma, IP-10, PF4, GRO, 9E3, erythropoietin, endostatin, angiostatin, fibroblast growth factor, VEGF, soluble receptor, or any fragments or combinations thereof.

103. The method of claim 86, wherein the nucleic acid or desired protein is erythropoietin or fragments thereof.

104. The method of claim 86, wherein the nucleic acid or desired protein is endostatin or fragments thereof.

105. The method of claim 86, wherein the nucleic acid or desired protein is angiostatin or fragments thereof.

106. The method of claim 86, wherein the nucleic acid or desired protein is IL12 or fragments thereof.

107. The method of claim 86, wherein the nucleic acid or desired protein is IL2 or fragments thereof.

108. The method of claim 86, comprising the further step of administering the transfected cells to a patient.

109. A method of delivering a therapeutic agent to patient comprising:
incorporating the therapeutic agent into platelets by electroporation using a flow electroporation channel having a thermal resistance of less than approximately 10° C. per Watt; and
administering the platelets to the patient.

110. The method of claim 109, wherein the thermal resistance of the flow channel is less than approximately 4° C. per Watt.

111. The method of claim 109, wherein the thermal resistance of the flow channel is approximately 0.1° C. per Watt to 4° C. per Watt.

112. The method of claim 109, wherein the thermal resistance of the flow channel is approximately 1.5° C. per Watt to 2.5° C. per Watt.

113. The method of claim 109, wherein the platelets are administered to the patient intravenously.

114. The method of claim 109, wherein the therapeutic agent is AGM-1470 (TNP-470), MetAP-2; growth factor antagonists; antibodies to growth factors; growth factor receptor antagonists; TIMP; batimastat; marimastat; genistein; SU5416; alphaVbeta3/5; retinoic acid fenretinide; 11α-epihydrocortisol; corteloxone; tetrahydrocortisone; 17α-hydroxyprogesterone; staurosporine; MDL 27032; 22-oxa-1 alpha; 25-dihydroxyvitamin D3; indomethacin; sulindac; minocycline; thalidomide and thalidomide analogs and derivatives; 2-methoxyestradiol; tumor necrosis factor-alpha; interferon-gamma-inducible protein 10 (IP-10); interleukin 1; interleukin 12; interferon alpha, beta or gamma; angiostatin protein; plasminogen fragments; endostatin protein; collagen 18 fragments; proliferin-related protein; group B streptococcus toxin; CM101; CAI; troponin I; squalamine; L-NAME; thrombospondin; wortmannin; amiloride; spironolactone; ursodeoxycholic acid; bufalin; suramin; tecogalan sodium; linoleic acid; captopril; irsogladine; FR-118487; triterpene acids; castanospermine; leukemia inhibitory factor; lavendustin A; platelet factor-4; herbimycin A; diaminoantraquinone; taxol; aurintricarboxylic acid; DS-4152; pentosan polysulphite; radicicol; fragments of human prolactin; erbstatin; eponemycin; shark cartilage; protamine; Louisianin A, C and D; PAF antagonist WEB 2086; auranofin; ascorbic ethers; or sulfated polysaccharide D 4152.

115. A method comprising:
flowing a suspension of CLL-B cells to be electroporated through a flow channel; and
exposing said suspension of CLL-B cells to an electric field while flowing through said flow channel, said electric field having a strength of greater than 0.5 kV/cm.

116. The method of claim 115, wherein said electric field has a strength of greater than approximately 3.5 kV/cm.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ctcgagatgg gggtgcacga atgtcctgcc                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gtcgactcat ctgtcccctg tcctgcaggc                                    30
```